United States Patent
Stahl et al.

(10) Patent No.: US 10,385,358 B2
(45) Date of Patent: Aug. 20, 2019

(54) PLANT-DERIVED CIS-REGULATORY ELEMENTS FOR THE DEVELOPMENT OF PATHOGEN-RESPONSIVE CHIMERIC PROMOTORS

(71) Applicant: KWS SAAT SE, Einbeck (DE)

(72) Inventors: Dietmar Stahl, Einbeck (DE); Fridtjof Weltmeier, Einbeck (DE); Reinhard Hehl, Braunscheig (DE); Jeannette Koschmann, Konigslutter (DE); Julia Niemeyer, Aerzen (DE)

(73) Assignee: KWS SAAT SE, Einbeck (DE)

( * ) Notice: Subject to any disclaimer, the term of this patent is extended or adjusted under 35 U.S.C. 154(b) by 1123 days.

(21) Appl. No.: 14/367,521

(22) PCT Filed: Dec. 21, 2012

(86) PCT No.: PCT/DE2012/001223
§ 371 (c)(1),
(2) Date: Jun. 20, 2014

(87) PCT Pub. No.: WO2013/091612
PCT Pub. Date: Jun. 27, 2013

(65) Prior Publication Data
US 2015/0040269 A1    Feb. 5, 2015

(30) Foreign Application Priority Data
Dec. 23, 2011    (DE) .......................... 10 2011 122 267

(51) Int. Cl.
C12N 15/82    (2006.01)

(52) U.S. Cl.
CPC ................................ *C12N 15/8279* (2013.01)

(58) Field of Classification Search
CPC ............ C12N 15/8239; C12N 15/8279; C12N 15/8281; C12N 15/8282; C12N 15/11; C12N 15/8216; A01H 5/00; C12Q 1/6897
See application file for complete search history.

(56) References Cited

U.S. PATENT DOCUMENTS

| | | | | |
|---|---|---|---|---|
| 6,100,451 A * | 8/2000 | Chappell | .............. | C07K 14/195 435/320.1 |
| 8,013,138 B1 * | 9/2011 | Kirsch | ............... | C12N 15/8239 435/410 |

(Continued)

FOREIGN PATENT DOCUMENTS

| WO | WO 00/29592 | 5/2000 |
|---|---|---|
| WO | WO 02/50293 | 6/2002 |

(Continued)

OTHER PUBLICATIONS

Rushton, P J. et al. (2002). Synthetic plant promoters containing defined regulatory elements provide novel insights into pathogen- and wound-induced signaling. Plant Cell 14, 749-762.*

(Continued)

*Primary Examiner* — Weihua Fan
(74) *Attorney, Agent, or Firm* — Troutman Sanders LLP

(57) ABSTRACT

The invention relates to an isolated cis-regulatory element imparting pathogen inducibility or elicitor inducibility, which comprises a nucleic acid molecule, the nucleotide sequence of which corresponds to one of the core sequence motifs comprising a) vaaagtm, b) aaacca, c) scaaam, d) acrcg, e) sktgkact, f) mrtsack, g) ccaccaa, h) tcgtctcttc (SEQ ID NO: 35), i) wwkgwc or a core sequence motif complementary to a) to i).

24 Claims, 48 Drawing Sheets

Figure 1:
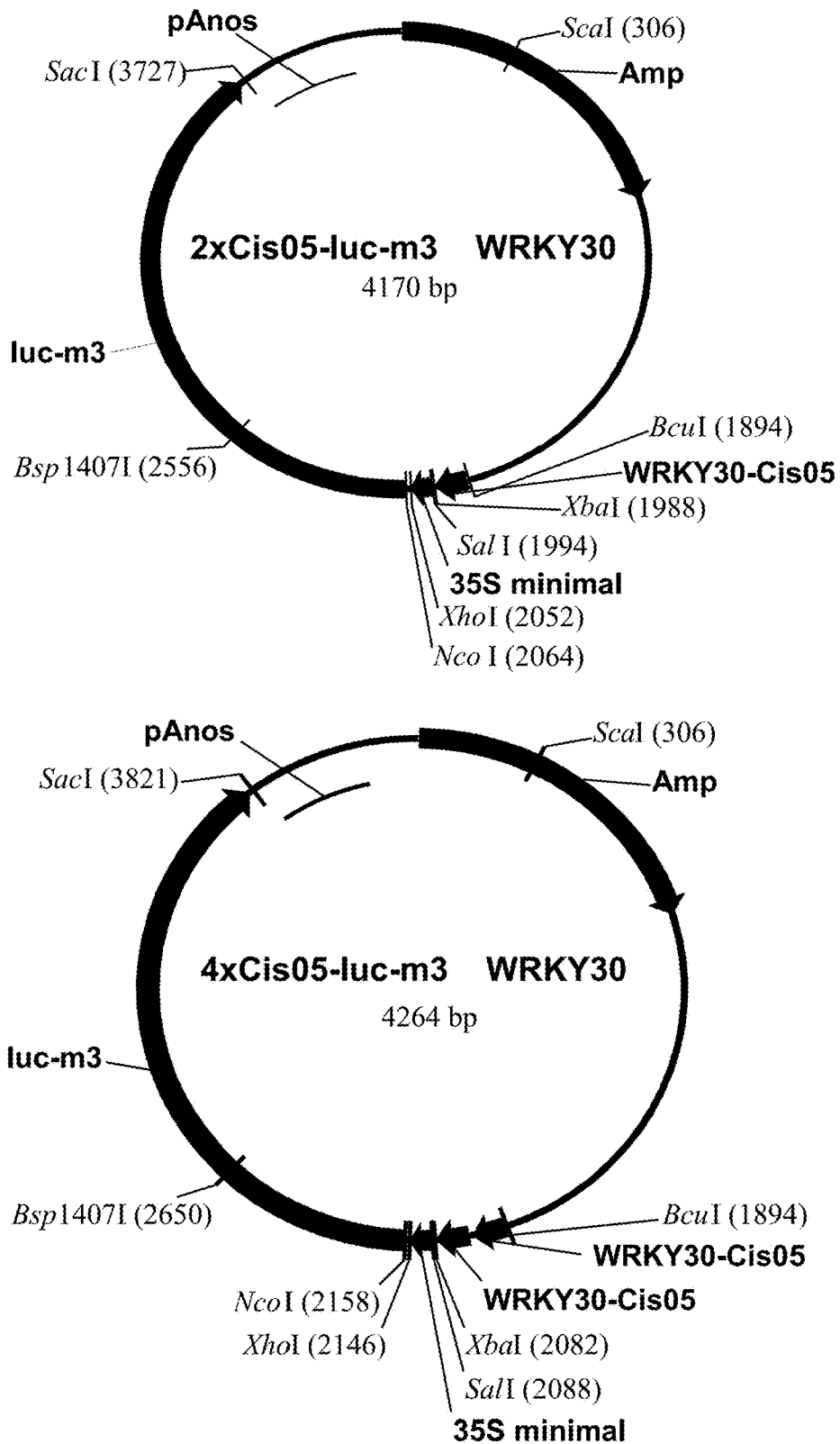

Specification includes a Sequence Listing.

(56) References Cited

U.S. PATENT DOCUMENTS

| | | | |
|---|---|---|---|
| 2009/0151015 A1* | 6/2009 | Adam | C12N 15/8239<br>800/265 |
| 2009/0188006 A1* | 7/2009 | Schmidt | C07K 14/415<br>800/279 |
| 2011/0145940 A1 | 6/2011 | Voytas et al. | |
| 2012/0064620 A1 | 3/2012 | Bonas et al. | |
| 2012/0122205 A1 | 5/2012 | Bonas et al. | |
| 2012/0178131 A1 | 7/2012 | Voytas et al. | |
| 2012/0178169 A1 | 7/2012 | Voytas et al. | |
| 2012/0214228 A1 | 8/2012 | Voytas et al. | |
| 2013/0122581 A1 | 5/2013 | Voytas et al. | |

FOREIGN PATENT DOCUMENTS

| | | |
|---|---|---|
| WO | WO 03/000898 | 1/2003 |
| WO | WO 2007/147395 | 12/2007 |
| WO | WO 2010/079430 | 7/2010 |
| WO | WO 2011/072246 | 6/2011 |

OTHER PUBLICATIONS

Bernard, Virginie, Véronique Brunaud, and Alain Lecharny. "TC-motifs at the TATA-box expected position in plant genes: a novel class of motifs involved in the transcription regulation." BMC genomics 11.1 (2010): 166.*
Spencer, T. Michael, et al. "Segregation of transgenes in maize." Plant Molecular Biology 18.2 (1992): 201-210.*
Rushton, Paul J., et al. "Synthetic plant promoters containing defined regulatory elements provide novel insights into pathogen- and wound-induced signaling." The Plant Cell 14.4 (2002): 749-762. (Year: 2002).*
Yamamoto, Yoshiharu Y., and Junichi Obokata. "PPDB: A plant promoter database." Nucleic acids research 36.suppl_1 (2007): D977-D981. (Year: 2007).*
Bailey, Timothy L., et al. "Fitting a Mixture Model by Expectation Maximization to Discover Motifs in Biopolymers" Proc Int Conf Intell Syst Mol Biol. 1994, 2:28-36.
Bülow, Lorenz , et al. "PathoPlant®: a platform for microarray expression data to analyze co-regulated genes involved in plant defense responses" Nucleic Acids Research 2007, 35:D841-845.
Che , Dongsheng, et al. "BEST: Binding-site Estimation Suite of Tools" Bioinformatics Applications Note 2005, 21(12):2909-2911.
Clough, Steven J., et al. "Floral dip: a simplified method for Agrobacterium-mediated transformation of Arabidopsis thaliana" The Plant Journal 1998, 16(6):735-743.
Eulgem, Thomas, et al. "The WRKY superfamily of plant transcription factors" Trends in Plant Science Reviews 2000, 5(5): 199-206.
Görlich, Dirk, et al. "Nucleocytoplasmic Transport" Science 1996, 271(5255):1513-1518.
Gurr, Sarah J., et al. "Engineering plants with increased disease resistance: how are we going to express it?" Trends in Biotechnology 2005, 23(6): 283-290.
Hahlbrock, Klaus, et al. "Oligopeptide elicitor-mediated defense gene activation in cultured parsley cells" Proc. Natl. Acad. Sci. 1995, 92:4150-4157.
Hicks, Glenn R., et al. "Three Classes of Nuclear Import Signals Bind to Plant Nuclei[1]" Plant Physiol. 1995, 107(4):1055-1058.
Himmelbach, Axel, et al. "Promoters of the Barley Germin-Like GER4 Gene Cluster Enable Strong Transgene Expression in Response to Pathogen Attack" The Plant Cell 2010, 22(3):937-952.
Howles, Paul, et al. "Autoactive Alleles of the Flax L6 Rust Resistance Gene Induce Non-Race-Specific Rust Resistance Associated with the Hypersensitive Response" Molecular Plant-Microbe Interactions 2005, 18(6):570-582.
Humphry, Matt, et al. "A regulon conserved in monocot and dicot plants defines a functional module in antifungal plant immunity" Proc Natl Acad Sci 2010, 107(50):21896-21901.
Jefferson, Richard A., et al. "GUS fusions: β-glucuronidase as a sensitive and versatile gene fusion marker in higher plants" The EMBO Journal 1987, 6(13):3901-3907.
Kirsch, Christoph, et al. "A highly specific pathogen-responsive promoter element from the immediate-early activated CMPG1 gene in Petroselinum crispum" The Plant Journal 2001, 26(2):217-227.
Kirsch, Christoph, et al. "A novel regulatory element involved in rapid activation of parsley ELI7 gene family members by fungal elicitor or pathogen infection" Molecular Plant Pathology 2000, 1(4):243-251.
Kovalchuk, Nataliya, et al. "Defensin promoters as potential tools for engineering disease resistance in cereal grains" Plant Biotechnology Journal 2010, 8(1):47-64.
Lebel, Edouard, et al. "Functional analysis of regulatory sequences controlling PR-1 gene expression in Arabidopsis" The Plant Journal 1998, 16(2):223-233.
Liu, X., et al. "Bioprospector: Discovering Conserved DNA Motifs in Upstream Regulatory Regions of Co-Expressed Genes" Pacific Symposium on Biocomputing 2001, 6:127-138.
Morris, Karl, et al. "Salicylic acid has a role in regulating gene expression during leaf senescence" The Plant Journal 2000, 23(5):677-685.
Rushton, Paul J., et al. "Synthetic Plant Promoters Containing Defined Regulatory Elements Provide Novel Insights into Pathogen- and Wound-Induced Signaling" The Plant Cell 2002, 14(4):749-762.
Rushton, Paul J., et al. "Interaction of elicitor-induced DNA-binding proteins with elicitor response elements in the promoters of parsley PR1 genes" The EMBO Journal 1996, 15(20):5690-5700.
Schatz, Gottfried, et al. "Common Principles of Protein Translocation Across Membranes" Science 1996, 271(5255):1519-1526.
Schumacher, Sylvie Briand, et al. "Development of a dual luciferase reporter screening assay for the detection of synthetic glucocorticoids in animal tissues" Analyst 2003, 128(12):1406-1412.
Shokouhifar, F., et al. "Construction and functional analysis of pathogen-inducible synthetic promoters in Brassica napus" Biologia Plantarum 2011, 55(4):689-695.
Strittmatter, Günter, et al. "Infections with Various Types of Organisms Stimulate Transcription from a Short Promoter Fragment of the Potato gstl Gene" Molecular Plant-Microbe Interactions 1996, 9(1):68-73.
Venter, Mauritz. "Synthetic promoters: genetic control through cis engineering" TRENDS in Plant Science 2007, 12(3):118-124.
Verner, Keith, et al. "Protein Translocation Across Membranes" Science 2007, 241(4871):1307-1313.
Wan, Jinrong, et al. "Chitin signaling and plant disease resistance" Plant Signaling & Behavior 2008, 3(10):831-833.
Wan, Jinrong, et al. "A LysM Receptor-Like Kinase Plays a Critical Role in Chitin Signaling and Fungal Resistance in Arabidopsis" The Plant Cell 2008, 20(2):471-481.
Wingender ,Ruth, et al. "cis-Regulatory Elements Involved in Ultraviolet Light Regulation and Plant Defense" The Plant Cell 1990, 2:1019-1026.
XP-002698295 Sequence 2372 from EP1502950.
XP-002698296 Sequence 2058 from U.S. Pat. No. 5,837,542.
Zipfel, Cyril, et al. "Perception of the Bacterial PAMP EF-Tu by the Receptor EFR Restricts Agrobacterium-Mediated Transformation" Cell 2006, 125(4):749-760.
Zipfel, Cyril, et al. "Bacterial disease resistance in Arabidopsis through flagellin perception" Nature 2004, 428(6984):764-767.
International Search Report dated Aug. 26, 2013, which issued during prosecution of International Application No. PCT/DE2012/001223, which corresponds to the present application.
Written Opinion of the International Searching Authority dated Aug. 26, 2013, which issued during prosecution of International Application No. PCT/DE2012/001223, which corresponds to the present application.

* cited by examiner

| Identifier | Group | Individual Sequence |
|---|---|---|
| 12i_M1_S1 | 1 | TCTCATCTCTCGACACGCAACTTCC |

| DE | 12I | M1 | | | |
|---|---|---|---|---|---|
| 0 | 0 | 1 | 0 | 5 | T |
| 1 | 0 | 0 | 6 | 0 | G |
| 2 | 0 | 2 | 0 | 4 | t |
| 3 | 0 | 0 | 6 | 0 | G |
| 4 | 2 | 0 | 0 | 4 | t |
| 5 | 3 | 1 | 2 | 0 | a |
| 6 | 0 | 1 | 3 | 2 | g |
| 7 | 6 | 0 | 0 | 0 | A |
| 8 | 6 | 0 | 0 | 0 | A |
| 9 | 6 | 0 | 0 | 0 | A |
| 10 | 6 | 0 | 0 | 0 | A |
| 11 | 0 | 1 | 5 | 0 | G |
| 12 | 0 | 0 | 0 | 6 | T |
| 13 | 0 | 6 | 0 | 0 | C |

| Identifier | Group | Individual Sequence |
|---|---|---|
| Cis12 | 1 | CAAAAAGTCAACACATACGACGCGTTTCCATTGACTAAATA |
| M004-Cismodule | | DE M004-Cismodule<br>1  54.7  32.8  12.5  0     A<br>2  0     100   0     0     C<br>3  35.9  0     64.1  0     G<br>4  1.6   78.1  0     20.3  C<br>5  0     0     100   0     G<br>6  0     1.6   3.1   95.3  T |

FIG 2 E

| Identifier | Group | Individual Sequence |
|---|---|---|
| 28M-1_M1_S1 | 5 | TTACGTGTCAAGAAGTGATTGGAGAGGACACTCTAC |

28M-1 sequence logo (bits vs position 1-15)

| DE | 28M-1 | | M1 | | |
|---|---|---|---|---|---|
| 0 | 0 | 1 | 2 | 6 | t |
| 1 | 0 | 6 | 3 | 0 | c |
| 2 | 0 | 0 | 1 | 8 | T |
| 3 | 0 | 9 | 0 | 0 | C |
| 4 | 0 | 1 | 0 | 8 | T |
| 5 | 2 | 7 | 0 | 0 | C |
| 6 | 3 | 2 | 4 | 0 | g |
| 7 | 0 | 0 | 0 | 9 | T |
| 8 | 0 | 5 | 0 | 4 | c |
| 9 | 6 | 0 | 1 | 2 | a |
| 10 | 0 | 9 | 0 | 0 | C |
| 11 | 0 | 0 | 0 | 9 | T |
| 12 | 0 | 2 | 0 | 7 | T |
| 13 | 0 | 4 | 0 | 5 | t |
| 14 | 0 | 1 | 0 | 8 | T |

FIG 2 F

| Identifier | Group | Individual Sequence |
|---|---|---|
| GG6_M1_S1 | 11 | GACTTTTGACCTAAACCATTTCCAT |

| DE | GG6 | M1 | | | |
|---|---|---|---|---|---|
| 0 | 8 | 1 | 2 | 0 | a |
| 1 | 11 | 0 | 0 | 0 | A |
| 2 | 0 | 11 | 0 | 0 | C |
| 3 | 0 | 9 | 2 | 0 | C |
| 4 | 0 | 0 | 6 | 5 | g |
| 5 | 7 | 4 | 0 | 0 | a |
| 6 | 9 | 2 | 0 | 0 | A |
| 7 | 11 | 0 | 0 | 0 | A |
| 8 | 0 | 11 | 0 | 0 | C |
| 9 | 0 | 7 | 4 | 0 | c |
| 10 | 8 | 0 | 2 | 1 | a |

| Identifier | Group | Individual Sequence |
|---|---|---|
| 18H_M2_S1 | 12 | CAACACAAAACGCAAACGCAGACCTC |
| 18H_M2_S3 | 12 | AATTGACAAAAGACACGCAAACGATTCCAACGACC |

| DE | 18H | M2 | | | |
|---|---|---|---|---|---|
| 0 | 0 | 0 | 16 | 0 | G |
| 1 | 0 | 0 | 1 | 15 | T |
| 2 | 0 | 0 | 2 | 14 | T |
| 3 | 0 | 0 | 1 | 15 | T |
| 4 | 0 | 1 | 15 | 0 | G |
| 5 | 0 | 8 | 8 | 0 | c |
| 6 | 0 | 0 | 16 | 0 | G |
| 7 | 0 | 3 | 7 | 6 | g |
| 8 | 1 | 7 | 4 | 4 | c |

FIG 2 K

| Identifier | Group | Individual Sequence |
|---|---|---|
| 38M_M1_S1 | 12 | AAATAATTATTTATGGTTTGGTCATTTG GTCAAAT |
| (sequence logo: positions 1-9, 5' to 3', showing GAGT TTGGT / A G consensus) | | DE  38M  M1<br>0   23   5   11   39   t<br>1   0    0   78   0    G<br>2   45   0   33   0    a<br>3   0    20  17   41   t<br>4   0    0   0    78   T<br>5   0    0   0    78   T<br>6   0    0   78   0    G<br>7   0    0   78   0    G<br>8   0    0   19   59   T |

| Identifier | Group | Individual Sequence |
|---|---|---|
| 26LLL_M1_S2 | 12 | AGTCAAAACGTAGACCAAAACAAAAACATGTAACT |

| DE | 26LLL | M1 | | | |
|---|---|---|---|---|---|
| 0 | 0 | 40 | 0 | 0 | C |
| 1 | 0 | 40 | 0 | 0 | C |
| 2 | 40 | 0 | 0 | 0 | A |
| 3 | 40 | 0 | 0 | 0 | A |
| 4 | 40 | 0 | 0 | 0 | A |
| 5 | 30 | 10 | 0 | 0 | A |
| 6 | 0 | 40 | 0 | 0 | C |

| Identifier | Group | Individual Sequence |
|---|---|---|
| GG13_M1_S2 | 27 | TGTTCACTTTGAAAAGTATTCTTTGAG |

| DE | GG13 | M1 | | | |
|---|---|---|---|---|---|
| 0 | 0 | 2 | 7 | 1 | g |
| 1 | 0 | 1 | 0 | 9 | T |
| 2 | 0 | 0 | 0 | 10 | T |
| 3 | 0 | 0 | 0 | 10 | T |
| 4 | 1 | 0 | 9 | 0 | G |
| 5 | 10 | 0 | 0 | 0 | A |
| 6 | 8 | 0 | 1 | 1 | A |
| 7 | 9 | 0 | 1 | 0 | A |
| 8 | 8 | 2 | 0 | 0 | A |
| 9 | 1 | 0 | 9 | 0 | G |
| 10 | 0 | 0 | 0 | 10 | T |
| 11 | 5 | 0 | 3 | 2 | a |
| 12 | 0 | 1 | 1 | 8 | T |
| 13 | 1 | 0 | 0 | 9 | T |
| 14 | 0 | 10 | 0 | 0 | C |

| Identifier | Group | Individual Sequence | | | | |
|---|---|---|---|---|---|---|
| 21S_M3_S1 | 27 | TAATTTCTCTTGCGTAGAAAAGTCT GATCGGGAAG | | | | |
| | | DE | 21S | M3 | | |
| | | 0 | 0 | 0 | 6 | 0 | G |
| | | 1 | 0 | 2 | 1 | 3 | t |
| | | 2 | 0 | 1 | 5 | 0 | G |
| | | 3 | 1 | 0 | 0 | 5 | T |
| | | 4 | 1 | 1 | 3 | 1 | g |
| | | 5 | 0 | 0 | 4 | 2 | g |
| | | 6 | 6 | 0 | 0 | 0 | A |
| | | 7 | 6 | 0 | 0 | 0 | A |
| | | 8 | 6 | 0 | 0 | 0 | A |
| | | 9 | 5 | 0 | 1 | 0 | A |
| | | 10 | 0 | 0 | 6 | 0 | G |
| | | 11 | 0 | 0 | 0 | 6 | T |
| | | 12 | 0 | 6 | 0 | 0 | C |

| Identifier | Group | Individual Sequence |
|---|---|---|
| Cis02 | 27 | GAGCGTGAATTGACTTTGACCAAAACCAAA |
| Cis05 | 27 | GGTCAGCATGTTGGACTTTCCAAATTCATTGACCAAAG |
|  | | DE   M027-BioProspector<br>1   0.0   54.7   45.3   0.0   C<br>2   58.5  26.4   0.0    15.1  A<br>3   99.9  0.0    0.0    0.0   A<br>4   79.2  0.0    20.8   0.0   A<br>5   0.0   0.0    99.9   0.0   G<br>6   0.0   0.0    0.0    99.9  T<br>7   0.0   99.9   0.0    0.0   C |

| Identifier | Group | Individual Sequence |
|---|---|---|
| Cis13 | 27 | AAAATAAACAGCTACTTGACGAAAA GTCAAACCAAATTC |

```
DE  M143-MEME
1   21  22  0   0   C
2   37  6   0   0   A
3   39  0   0   4   A
4   40  0   0   3   A
5   0   0   43  0   G
6   0   1   0   42  T
7   0   43  0   0   C
8   40  3   0   0   A
9   41  0   2   0   A
10  18  15  4   6   A
```

Motif group 1

```
12i_M1_S1      CTCGACACGCAAC
Cis09          ACACACACGTGTA
Cis12          TACGACGCGTTC
```

Core sequence motif:   ACRCG

Family motif:

Motif group 5

```
20u_M1_S1          GTTTACGTCACGTCG
20u_M1_S2          TAATACGTGACGAAA
28M-1_M1_S1(inv)   TCTCCAATCACTTCT
```

Core sequence motif:    MRTSACK

Family motif:

Motif group 11

GG6_M1_S1      TGACCT<u>AAACCA</u>TTTC
GG11_M1_S1     TGACCT<u>AAACCA</u>TTTC
22DDD_M1_S1    TTACCG<u>AAACCA</u>AAGT
21G-2_M1_S2 *(inv)*  CAAACC<u>AAACCA</u>AACC Core sequence motif:     AAACCA Family motif:

Motif group 12

```
18H_M2_S1        AAAC GCAAAC GCA
18H_M2_S3        ACAC GCAAAC GAT
26LLL_M1_S2      TAGA CCAAAA CAA
38M_M1_S1(inv)   ATGA CCAAAC CAT
```

Core sequence motif:    SCAAAM

Family motif:

Motif group 21

```
GG8_M1_S1      ACGTGTACTAGGTC
27G-8_M1_S1    AGTTGGACTTTGAA
```

Core sequence motif:    SKTGKACT

Family motif:

Motif group 27

```
30I-8_M1_S1(inv)   AATTATG AAAAGTC GTCT
30I-8_M1_S2        ATATGAC AAAAGTC AAAC
14S_M1_S1(inv)     TGCGTAG AAAAGTC TGAT
GG13_M1_S2         CACTTTG AAAAGTA TTCT
30I-8_M1_S3        TCAGTCA AAAAGTC AAAC
21S_M3_S1          TGCGTAG AAAAGTC TGAT
Cis13              CTTGACG AAAAGTC AAAC
Cis02(inv)         TTTTGGT CAAAGTC AATT
Cis05(inv)         GAATTTG GAAAGTC CAAC
```

Core sequence motif: VAAAGTM

Family motif:

Motif group 21n

GG8_M1_S1         CACGTGTACTAGGTCAAACCA
27G-8_M1_S1       TTTCACCAGTTGGACTTGAA
26WW_M2_S1        AAGGCCAGAATTGACGCAGCC
27B-10_M1_S3      GCCCAGTCCTTGGTCGTCGTA

Core sequence motif:      WWKGWC

Family motif:

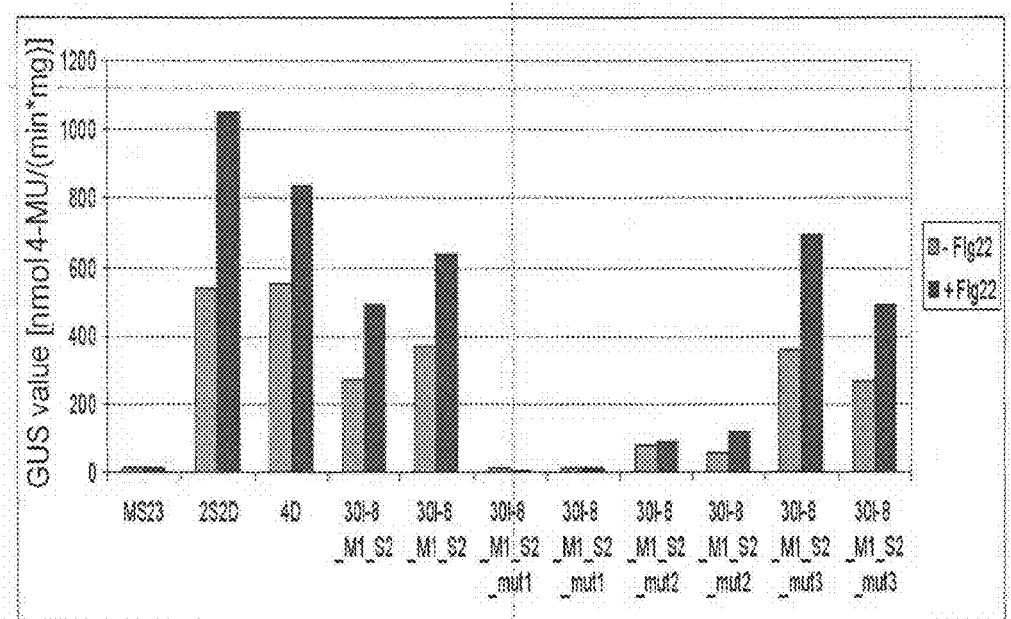
FIG 6 A
CTATATGACAAAAGTCAAACATAAA     30I-8_M1_S2
CTATATGACAAAAGAGAAACATAAA     30I-8_M1_S2_mut1
CTATATGACATTAGTCAAACATAAA     30I-8_M1_S2_mut2
CTATATCTCAAAAGTCAAACATAAA     30I-8_M1_S2_mut3
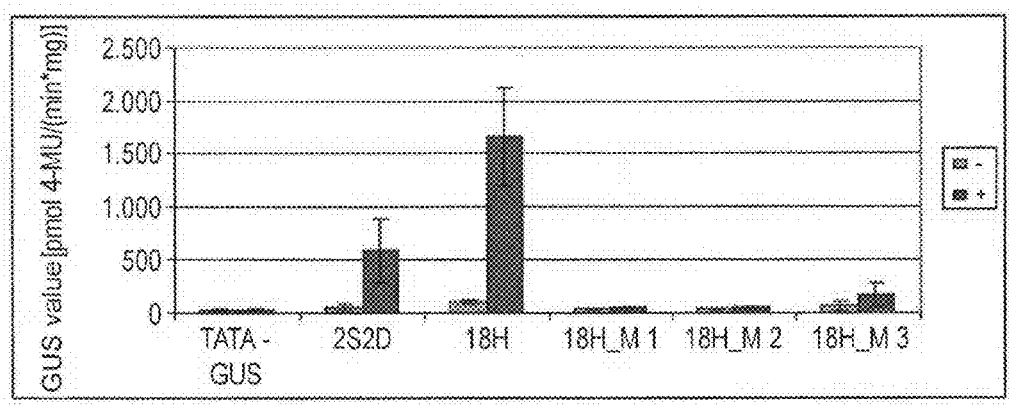
CAACACAAAACGCAAACGCAGACCTC     18H_M2_S1
CAACACAAAACGCTTTCGCAGACCTC     18H_M2_S1mut1
CAACACAAATGCCAAACGCAGACCTC     18H_M2_S1mut2
CAACACAAAACGCAAACGTGACCTC     18H_M2_S1mut3

FIG 6 B
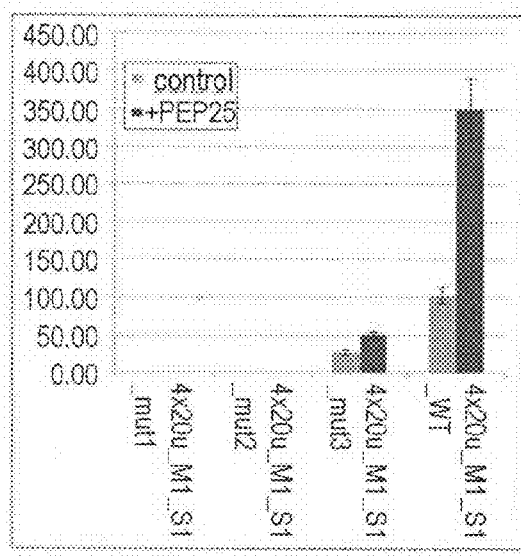
TGAGTCGTTTACGTCACGTCGAGAATTTT     20u_M1_S1_WT
TGAGTCGTTTACGCTGTGTCGAGAATTTT     20u_M1_S1_mut1
TGAGTCGTTGCCGTCACGTCGAGAATTTT     20u_M1_S1_mut2
TGAGTCGTTTACGTCACGGTGAGAATTTT     20u_M1_S1_mut3
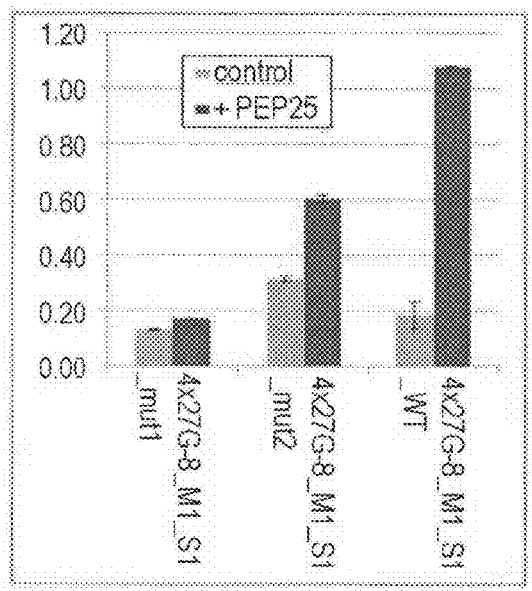
ACTTTTCACCAGTTGGACTTTGAAGCCAC     27G-8_M1_S1_WT
ACTTTTCACCAGTCAGGTCTTGAAGCCAC     27G-8_M1_S1_mut1
ACTTTTCACCGGTTGGACTTTAAAGCCAC     27G-8_M1_S1_mut2

FIG 11

PLANT-DERIVED CIS-REGULATORY ELEMENTS FOR THE DEVELOPMENT OF PATHOGEN-RESPONSIVE CHIMERIC PROMOTORS

CROSS-REFERENCE TO RELATED APPLICATIONS

This is a U.S. national phase application under 35 U.S.C. § 371 of International Patent Application No. PCT/DE2012/001223 filed Dec. 21, 2012, and claims benefit of priority to German Application No. DE 10 2011 122 267.0 filed on Dec. 23, 2011. The International Application was published on Jun. 27, 2013, as International Publication No. WO 2013/091612 under PCT Article 21(2). The entire contents of these applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Oct. 10, 2014, is named 245761.000002_SL.txt, and is 29,892 bytes in size.

The present invention relates to cis-regulatory elements and chimeric promoters, which include pathogen- or elicitor-induced activity in plants, created from said cis regulatory elements. The present invention furthermore relates to a host cell, a transgenic plant cell, a transgenic plant tissue, and a transgenic plant and its seeds. The present invention moreover relates to a method for producing a transgenic plant that in particular is resistant to a pathogen.

Plant diseases caused by fungi, viruses, nematodes, and bacteria cause considerable crop losses worldwide, negatively affect the quality of crops, and necessitate an expensive use of chemical pesticides because the natural defense mechanisms of plants, with which they can defend themselves against the majority of potential pathogens or delay and limit their spread, are often insufficient. Genetic engineering approaches can be used for generating plants that are resistant to such above-mentioned pathogens. Such plants have increased resistance by generating an expression of proteins (effectors) specifically at the infection location (location of contact between pathogen and plant), which proteins trigger a strong resistance reaction of the plant or of molecules that are themselves toxic to pathogens or inhibit their growth or virulence.

Effectors that trigger a strong resistance reaction of the plant are, e.g. proteins of auto-activated resistance genes (R-genes) or avirulence genes that lead to the activation of endogenous resistance genes of the plant. The hypersensitive reaction (HR), the controlled cell death of the host tissue at the infection location, the strengthening of the plant cell wall via lignification and callose form mation, the formation of phytoalexines, and the production of PR- (pathogenesis-related) proteins are counted among the stronger resistance reactions.

Since said resistance reactions present a high energy requirement and can lead to the death of plant cells (necrosis), their triggering must be subject to stringent monitoring. The same also applies for the expression of proteins or peptides toxic to pathogens inasmuch as a constitutive expression of these proteins or peptides has a disadvantageous effect on the plant or its agronomic traits such as yield, for example. In a transgenic approach, such control is possible by using promoters having the desired specificity.

A pathogen-induced expression of transgenes such as effectors can thus be achieved by using various known, natural pathogen-inducible promoters such as of the PR1-promoter, for example (Rushton et al., 1996). The development of the microarray technology in particular has led to the identification of a multitude of pathogen-inducible promoters (WO 03/00898, WO 02/50293 or JP 2003284566).

Such natural pathogen-inducible promoters can, however, display very unspecific activities since they can be activated by a large number of different stimuli. Such activities are attributed to a modular construction of the promoter from a plurality of different cis-regulatory elements that integrate diverse-as-possible different signals into a complex expression profile. Natural pathogen-inducible promoters are accordingly also characterized by undesired activities in certain tissues, for example, or by a high degree of background activity.

Thus, for example, pathogen-inducible promoters of defensin genes from wheat are also active during the seed development and seed germination (Kovalchuk et al., 2010). The already-mentioned PR1 promoter is induced not only by pathogens, but also by senescence (Morris et al. 2000)

Other research has shown that the natural, rust-inducible Fis1 promoter from flax was not suited after transformation to specifically regulate the expression of auto-active forms of the L6 rust-resistance gene in *Linum usitatissimum* such that in addition to the rust resistance, no negative agronomic traits such as restricted growth arose (Howles et al., 2005).

The identification of the cis-regulatory elements responsible for the desired induction and the construction of chimeric promoters from said cis-regulatory elements is a possibility for increasing the desired specificity of a promoter (Venter, 2007). Sequence motifs for other stimuli are, on the other hand, removed.

The promoters of many pathogen-induced genes have been more closely examined, wherein a plurality of cis-regulatory elements that can impart a pathogen-specific induction were identified (Strittmatter et al., 1996; Eulgem et al., 2000; Kirsch et al., 2000, 2001; Himmelbach et al., 2010). The cis-regulatory elements D-box, S-box or W-box identified by the incremental mutation of natural pathogen-inducible promoters (WO 00/29592) or the left-hand scanning regions LS10 or LS7 (Lebel et al., 1998) are also additional examples. The W-box in particular has been well investigated and its core sequence TTGAC(C/T) can be used to find additional variants of the W-box in natural pathogen-inducible promoters.

New cis-regulatory elements can furthermore be identified bioinformatically using programs such as MEME (Bailey and Elkan, 1994; Humphry et al., 2010) or BEST (Che et al., 2005). An advantage of this is that a cis-regulatory element is identified not as a short single sequence, but rather as a precisely defined sequence motif via which even more variants of a cis-regulatory element, that is to say many variants of a binding site of transcription factor, are detected. Such bioinformatic approaches are, however, also highly susceptible to yielding false-positive sequences such that these approaches merely lead to a screening of potential sequences or sequence motifs. Proof and verification of the functionality as a cis-regulatory element in general, and specifically as a cis-regulatory element that imparts pathogen-inducibility, remain essential and obligatory. Such experimental analyses are furthermore associated with considerable expense.

An additional increase in the specificity of a promoter is possible by using combinations of different cis-regulatory elements (Rushton et al., 2002). It is not the combination itself that leads to an increase of the activity (synergism), but rather such a synergism occurs only with specific individual, non-predictable combinations and must in any case be determined empirically. Chimeric promoters having combinations from the cis-regulatory elements D-box and S-box, for example, are known (WO 00/29592). The number of the element repetitions modulates the promoter strength and the background activity.

A further problem in the development of pathogen-inducible chimeric promoters is their functionality in different plant species. Although generally pathogen inducibility via the known pathogen-inducible chimeric promoters can be determined in nearly all plant varieties analyzed thus far, they still exhibit background activity even when not under attack by a pathogen. Such background activity varies depending on the plant species in which the chimeric promoters are used. The same is true with the induction rate (ratio of the promoter activity in the infected tissue and promoter activity in uninfected tissue) and the absolute activity of the promoters (promoter strength). Thus, for example, when background activity is too strong in non-infected tissue, only a slight pathogen inducibility in the infected tissue is detected.

According to the current state of knowledge, the used cis-regulatory elements of a promoter are responsible for the described variations in background activity, induction rate, promoter strength, induction kinetics, and the scope of the promoter activation (Rushton et al., 2002, Venter, 2007). Even if the known chimeric promoters are superior to the natural promoters, there is still an optimization need for these chimeric promoters, especially in regard to the cis-regulatory elements and/or to the combinations of cis-regulatory elements. There is still a lack of well-characterized cis-regulatory elements and of suitable combinations of such cis-regulatory elements with which chimeric promoters can be constructed, which ensure a highly specific and controlled, appropriate pathogen-induced expression of transgenes themselves and also in various plant species, wherein the expression should occur only as a result of pathogen attack and almost exclusively at the site of infection (Gurr & Rushton, 2005). The object of the present invention is therefore to provide such novel cis-regulatory elements, and combinations thereof, imparted by pathogen inducibility.

Some of the terms used in this application will be first be explained below:

An "elicitor" in the sense of the present invention is an inductor or messenger that induces defenses against plant pathogens such as the synthesis of phytoalexines. Elicitors can be either endogenous or exogenous in origin. An elicitor (exogenous) preferably comes from a pathogen and is recognized by the plant. The PAMPs (pathogen associated molecular pattern) such as flagelin, PEP25, and chitin are also counted among to these elicitors. Elicitors can be used to imitate a pathogen infection or a contact with a pathogen by artificially applying the elicitor in the absence of the pathogen. In the context of the present invention, elicitors should be used in particular to monitor the inducibility of promoters.

A "single sequence" is a sequence of nucleotides or bases (pairs), wherein each position in the single sequence is determined by only one single predefined base (a, c, g or t). A single sequence is isolated from a natural promoter and represents the result of a bioinformatics analysis. A single sequence is composed of a core sequence and flanking sequence regions. The term "single sequence" also means a nucleic acid molecule the nucleotide- or base (pair)-sequences of which correspond to the single sequence.

A "core sequence" is the sequence of nucleotides or bases (base pairs) in a certain section of a cis-regulatory element, wherein said section is essential for the functionality of the cis-regulatory element. The core sequence represents a part of the single sequence. The term "core sequence" also means a nucleic acid molecule the nucleotide- or base-(pair)-sequences of which correspond to the core sequence.

A "promoter" means a non-translated DNA sequence, typically upstream from a coded region, which contains the binding site for the RNA polymerase and initiates the transcription of the DNA. A promoter additionally often contains other elements that act as regulators of the gene expression (e.g. cis-regulatory elements).

A "minimal promoter" is a promoter that has only the basic elements that are used for the transcription initiation (e.g. TATA-box and/or initiator).

A "chimeric promoter" is a promoter composed of a plurality of elements and that does not occur as such nature. It contains a minimal promoter and includes, upstream from the minimal promoter, at least one cis-regulatory element which serves as a binding site for specific trans-acting factors (e.g. transcription factors). A chimeric promoter is designed according to the desired requirements and is induced or repressed by different factors. The selection of the cis-regulatory element or a combination of cis-regulatory elements is critical for the specificity or the activity level of a promoter. A cis-regulatory element in a chimeric promoter is either heterologous to the minimal promoter used, i.e. the cis-regulatory element is derived from a different organism or from a different species to that of the minimal promoter used (exemplarily represented in FIG. 15A-C), or a cis-regulatory element in a chimeric promoter is homologous to the minimal promoter used, i.e. the cis-regulatory element and the minimal promoter also occur combined in a natural promoter, however the cis-regulatory element is localized itself or as an additional element within the chimeric promoter in a genetic environment that is different from the natural promoter. A chimeric promoter thus also means a (natural) promoter that was altered by multimerization of at least one cis-regulatory element (exemplarily represented in FIG. 15D).

A "complementary" nucleotide sequence in relation to a double-stranded DNA means that the second DNA strand complementary to the first DNA strand includes the nucleotide bases that correspond to the bases of the first strand in accordance with base-pairing rules and considering the orientation (e.g.: 5'-gcat-3' is complementary to 5'-atgc-3').

A "pathogen" means an organism that in interactions with a plant leads to illness symptoms in one or more organs of the plant. Animal, fungal, bacterial or viral organisms or oomycetes, for example, are among these pathogens.

"Pathogen infection" is to be understood as the earliest point in time at which the metabolism of a pathogen is prepared for a penetration of the plant host tissue. Included thereamong in, e.g., fungi or in oomycetes, is the maturation of hyphae or the formation of specific infection structures such as penetration hyphae and appressoria.

A "pathogen-/elicitor-inducibility" or "pathogen-/elicitor-inducible" in the sense of the present invention means the specific property of a promoter that causes, subsequent to pathogen infection or elicitor application, an at least two-fold stronger transcription of an operatively linked gene. "Pathogen-/elicitor-inducibility" or "pathogen-/elicitor-inducible" in the sense of the present invention furthermore means the property of genes to be transcribed at least two-fold stronger subsequent to pathogen infection or elicitor application.

The solution of the invention to the object posed is inventively effected by novel cis-regulatory elements imparting pathogen- and/or elicitor-inducibility. Said cis-regulatory elements distinguish themselves in particular within the core sequence significantly from already-known elements and thus do not represent a variation of the known elements. The inventive cis-regulatory elements should accordingly serve as recognition sites and/or binding sites for new transcription factors with the consequence that the imparted pathogen and/or elicitor inducibility has a novel specificity. The cis-regulatory elements according to the invention were identified in promoters of pathogen or PAMP (elicitor)-induced genes from *Arabidopsis thaliana* via bioinformatics approaches. The isolated single sequences of the cis-regulatory elements could be associated with eight motif groups (motif group 1, 5, 11, 12, 18, 21, 27 and 32) pursuant to various analysis steps. A plurality of isolated single sequences could moreover also be associated with a 21n motif group. Grouped in one motif group are those single sequences that demonstrate a high degree of conservation compared to the identified motifs. Single sequences of a motif group all correspond in a characteristic core sequence motif. The object posed is thus achieved by an isolated cis-regulatory element comprising a nucleic acid molecule, the nucleotide sequence of which corresponds to one of the core sequence motifs from a) vaaagtm,
b) aaacca,
c) scaaam,
d) acrcg,
e) sktgkact,
f) mrtsack,
g) ccaccaa,
h) tcgtctcttc (SEQ ID NO: 35) or
i) wwkgwc.

Less strongly conserved base positions within the characteristic core sequence motifs a) to i) are given as follows: 'r' stands for guanine (g) or adenine (a), thus a purine base, 'k' stands for guanine (g) or thymine (t)/uracil (u), 's' stands for guanine (g) or cytosine (c), 'm' stands for adenine (a) or cytosine (c) and 'w' stands for adenine (a) or thymine (t)/uracil (u). A certain core sequence motif reflects at least one partial sequence of the core sequence of one of each of the single sequences of the motif group belonging to the core sequence motif, wherein the partial sequence can constitute at least 30% of the entire core sequence of a single sequence. For those motif groups having core sequence motifs g) and h), the core sequence motif corresponds to the entire core sequence of the single sequences. The invention furthermore also includes an isolated cis-regulatory element comprising a nucleic acid molecule the nucleotide sequence of which corresponds to a core sequence motif complementary to a) to i). A characteristic core sequence motif of a certain motif group can moreover also repeatedly arise in the core sequence of a single sequence, wherein the core sequence motifs can also appear overlapping in the core sequence and/or respectively demonstrate a different orientation. For example, the core sequence of the Cis09 from motif group 1 demonstrates, on the one hand, a partial sequence that corresponds to the core sequence motif acrcg and, on the other hand, a partial sequence overlapping by two bases, which partial sequence corresponds to the complementary core sequence motif of acrcg, namely cgygt. A further example is found in the core sequence of the 21G-2_M1_S2 from motif group 11 where the core sequence has two partial sequences that overlap by one base and each corresponds to the complementary core sequence motif of aaacca, namely tggttt.

A family motif, in which the characteristic core sequence motif is embedded, could be defined for motif groups 1, 5, 11, 12, 21, 21n, and 27 based on the experimental data regarding functionality. The family motif represents a derived distinguishing feature for a transcription factor or a transcription factor family. The advantage of a family motif is that it subsumes possible variants of a recognition-/binding area. A family motif of a motif group advantageously comprises all core sequences of the single sequences grouped in the motif group. To achieve this, the complementary strand of the cis-regulatory element was considered for a part of the single sequences; such complementary sequences are from identified cis-regulatory sequences according to the invention, and are characterized with '(inv)' in the following inasmuch as needed for understanding. A family motif defined in such a manner has a length of at least 15 nucleotides, preferably of at least 13 nucleotides, especially preferred of at least 11 nucleotides. In addition to the corresponding core sequence motif, the family motif has motif flanking sites, wherein when a cis-regulatory element according to the invention is used in a chimeric promoter said motif flanking sites have a substantially quantitative influence on the properties thereof such as background activity and expression strength. The quantitative influence of said motif flanking site reduces with increasing distance from a certain base of the flanking site to the core sequence in a single sequence. Further highly conserved single bases from the flanking sites, which highly conserved single bases go beyond the core sequences of the single sequences and thus expand the family motif, can also be considered in defining the family motif. The family motifs for the motif groups 1, 5, 11, 12, 21, 21n, and 27 are shown in column 2 of Table 1. According to the invention, an isolated cis-regulatory element is also included that comprises a nucleic acid molecule, the nucleotide sequence of which corresponds to a) a family motif according to SEQ ID NO: 1, including the core sequence motif vaaagtm
b) a family motif according to SEQ ID NO: 2, including the core sequence motif aaacca,
c) a family motif according to SEQ ID NO: 3, including the core sequence motif scaaam,
d) a family motif according to SEQ ID NO: 4, including the core sequence motif acrcg,
e) a family motif according to SEQ ID NO: 5, including the core sequence motif sktgkact,
f) a family motif according to SEQ ID NO: 6, including the core sequence motif mrtsack,
g) a family motif according to SEQ ID NO: 41, including the core sequence motif wwkgwc,
or the nucleotide sequence of which corresponds to one of the family motifs complementary to a) to g).

It is also possible for a family motif to be shorter. In its shortest form, it is defined as a minimal family motif that based on the direction of the single sequences corresponding to the shared core sequence motif groups represents in itself only those base positions that are identified in the core sequences of all single sequences of a motif group. In some cases, the minimal family motif corresponds to the core sequence motif. Column 2, titled Family Motif, of Table 1 shows underlined the minimal family motifs of the motif groups 1, 5, 11, 12, 21, 21n, and 27.

TABLE 1

Representation of the motif groups 1, 5, 11, 12, 18, 21, 21n, 27, and 32, the core sequence motifs (1) and family motifs (2) underlying the groups, and the single sequences (3) associated with the motif groups; the minimal family motif is underlined, the core sequence motif is in bold typeface within family motif. ('n' stands for an arbitrary base; 'h' stands for a, c or t/u; 'd' stands for a, g or t/u; 'v' stands for a, g or c; 'r' stands for g or a, 'k' stands for g or t/u, 's' stands for g or c and 'm' stands for a or c; 'y' stands for t/u or c; 'w' stands for a or t/u)

| 1 Core sequence-motif | 2 Family motif | | 3 Single sequence identifier | |
|---|---|---|---|---|
| *Motif group 27* | | | | |
| vaaagtm | nnhkdnnvaaagtmndhy | (SEQ ID NO: 1) | 30I-8_M1_S1 | (SEQ ID NO: 7) |
| | | | 30I-8_M1_S2 | (SEQ ID NO: 8) |
| | | | GG13_M1_S2 | (SEQ ID NO: 9) |
| | | | 14S_M1_S1 | (SEQ ID NO: 10) |
| | | | 21S_M3_S1 | (SEQ ID NO: 11) |
| | | | 30I-8_M1_S3 | (SEQ ID NO: 12) |
| | | | Cis02 | (SEQ ID NO: 13) |
| | | | Cis05 | (SEQ ID NO: 14) |
| | | | sCis05 | (SEQ ID NO: 44) |
| | | | Cis13 | (SEQ ID NO: 15) |
| *Motif group 11* | | | | |
| aaacca | ynamcnaaaccawwny | (SEQ ID NO: 2) | GG11_M1_S1 | (SEQ ID NO: 16) |
| | | | 22DDD_M1_S1 | (SEQ ID NO: 17) |
| | | | 21G-2_M1_S2 | (SEQ ID NO: 18) |
| | | | GG6_M1_S1 | (SEQ ID NO: 19) |
| *Motif group 12* | | | | |
| scaaam | wnrmscaaamsmw | (SEQ ID NO: 3) | 18H_M2_S1 | (SEQ ID NO: 20) |
| | | | 18H_M2_S3 | (SEQ ID NO: 21) |
| | | | 38M_M1_S1 | (SEQ ID NO: 22) |
| | | | 26LLL_M1_S2 | (SEQ ID NO: 23) |
| *Motif group 1* | | | | |
| acrcg | nnmsacrcgynwm | (SEQ ID NO: 4) | Cis09 | (SEQ ID NO: 24) |
| | | | Cis12 | (SEQ ID NO: 25) |
| | | | 12i_M1_S1 | (SEQ ID NO: 26) |
| *Motif group 21* | | | | |
| sktgkact | asktgkactwkgwm | (SEQ ID NO: 5) | GG8_M1_S1 | (SEQ ID NO: 27) |
| | | | 27G-8_M1_S1 | (SEQ ID NO: 28) |
| *Motif group 21n* | | | | |
| wwkgwc | snsnnnwwkgwcnnnsnm | (SEQ ID NO: 41) | GG8_M1_S1 | (SEQ ID NO: 27) |
| | | | 27G-8_M1_S1 | (SEQ ID NO: 28) |
| | | | 26WW_M2_S1 | (SEQ ID NO: 42) |
| | | | 27B-10_M1_S3 | (SEQ ID NO: 43) |
| *Motif group 5* | | | | |
| mrtsack | knwymmrtsackwmn | (SEQ ID NO: 6) | 20u_M1_S1 | (SEQ ID NO: 30) |
| | | | 20u_M1_S2 | (SEQ ID NO: 31) |
| | | | 28M-1_M1_S1 | (SEQ ID NO: 32) |
| *Motif group 18* | | | | |
| ccaccaa | | | 12G_M2_S1 | (SEQ ID NO: 33) |
| *Motif group 32* | | | | |
| tcgtctcttc (SEQ ID NO: 35) | | | 12r_M1_S1 | (SEQ ID NO: 34) |

The invention furthermore also relates to all identified and isolated single sequences of cis-regulatory elements according to the invention and the core sequences thereof (Tables 1 and 2). The object posed is thus also achieved by an isolated cis-regulatory element, including nucleic acid molecule a) a nucleic acid molecule having a nucleotide sequence according to SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 42, SEQ ID NO: 43 or SEQ ID NO: 44, b) a nucleic acid molecule having a nucleotide sequence according to the core sequence from SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 42, SEQ ID NO: 43 or SEQ ID NO: 44, or c) a nucleic acid molecule having a nucleotide sequence complementary to one of the nucleotide sequences from a) or b).

A cis-regulatory element including a nucleic acid molecule with a nucleotide sequence according to SEQ ID NO: 24, SEQ ID NO: 25 or SEQ ID NO: 26 is associated with the motif group 1, cis-regulatory element with a nucleotide sequence according to SEQ ID NO: 30, SEQ ID NO: 31 or SEQ ID NO: 32 is associated with the motif group 5, a cis-regulatory element with a nucleotide sequence according to SEQ ID NO: 16, SEQ ID NO: 17, SEQ ID NO: 18 or SEQ ID NO: 19 is associated with the motif group 11, a cis-regulatory element with a nucleotide sequence according to SEQ ID NO: 20, SEQ ID NO: 21, SEQ ID NO: 22 or SEQ ID NO: 23 is associated with the motif group 12, a cis-regulatory element with a nucleotide sequence according to SEQ ID NO: 33 is associated with the motif group 18, a cis-regulatory element with a nucleotide sequence according to SEQ ID NO: 27 or SEQ ID NO: 28 is associated with the motif group 21, a cis-regulatory element with a nucleotide sequence according to SEQ ID NO: 27, SEQ ID NO: 28, SEQ ID NO: 42 or SEQ ID NO: 43 is associated with the motif group 21n, a cis-regulatory element with a nucleotide sequence according to SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 44 or SEQ ID NO: 15 is associated with the motif group 27, and a cis-regulatory element with the nucleotide sequence according to SEQ ID NO: 34 is associated with the motif group 32.

A cis-regulatory element according to the invention can have a length of fewer than 50 nucleotides, preferably of fewer than 40 nucleotides, and especially preferred of fewer than 30 nucleotides. The core sequence of a cis-regulatory element according to the invention can have a length of fewer than 20 nucleotides, preferably of fewer than 15 nucleotides, and especially preferably of fewer than 10 nucleotides, while the core sequence should not be shorter than 6 nucleotides.

In addition to having the identified novel core sequence, some single sequences of the cis-regulatory elements according to the invention can also have the core sequence of a known cis-regulatory element imparting pathogen-/elicitor-inducibility, which cis-regulatory element can also possibly influence the specificity of the novel identified core sequence and/or of the identified single sequence. An example is the cis-regulatory element Cis05 (SEQ ID NO: 14) that also has a W-box core sequence between the nucleotide positions 29 and 35 in addition to the identified core sequence between the nucleotide positions 14 and 20. Extensive mutation analyses were conducted pertaining hereto (see FIGS. 5A, 5B and 11).

A cis-regulatory element according to the invention can be used in a chimeric promoter, wherein the cis-regulatory element imparts a specific pathogenand/or elicitor inducibility to the chimeric promoter. The present invention thus also includes a chimeric promoter that, when induced by a pathogen infection or a treatment with a pathogenic elicitor, is suitable for effecting an expression of an operatively linked nucleic acid molecule of interest, e.g. of a heterologous DNA sequence, in a plant cell, and which chimeric promoter also includes a minimal promoter and at least one cis-regulatory element according to the invention. A single cis-regulatory element according to the invention in such a chimeric promoter by itself is in the position to impart a significant pathogen- and/or elicitor inducibility. Thus this single cis-regulatory element is itself sufficient for constructing a pathogen-/elicitor-responsive chimeric promoter in combination with a minimal promoter.

Such a chimeric promoter, containing only one or more inventive cis-regulatory elements as cis-regulatory elements, is preferably only pathogenand/or elicitor-responsive, i.e. this promoter is not or only minimally inducible by other stimuli such as abiotic stress. After pathogen/elicitor contact, the induction of such a chimeric promoter comprising one or more inventive cis-regulatory elements is at least 2-fold, preferably at least 10-fold, or particularly preferably at least 25-fold greater than the induction without pathogen/elicitor contact (background activity).

In a preferred embodiment, the induced expression is limited only locally to the infection site, i.e. comparably or to a lesser extent than occurs in the controlled expression of natural PR genes. Especially preferably the transcription activation occurs controlled by a chimeric promoter of the present invention just in the cells that come into contact with the pathogen or the pathogenic elicitor. However, owing to cell-cell interactions, a transcription activation can occur in cells surrounding the infection site(s).

Chimeric promoters of the present invention, however, are not limited to those that are exclusively pathogen responsive. The induced expression can be further specified by combination with additional regulatory elements, e.g. by combination with a cis-regulatory element that, for example tissue specificity, storage inducibility, cold- or heat inducibility or a specific activity in certain stages of development. Chimeric promoters of the invention can also comprise at least one combination of at least two cis-regulatory elements, wherein said cis-regulatory elements comprise at least one combination of at least one inventive cis-regulatory element. Known cis-regulatory elements imparting pathogen-/elicitor-inducibility, such as W-box, S-box or D-box (see WO 00/29592), can also be used as further cis-regulatory elements in the combination to construct a chimeric promoter.

The invention moreover also includes a chimeric promoter that comprises one or more monomers and/or one or more multimers of the inventive cis-regulatory elements. Dimers and tetramers are preferred multimeric forms. Monomers separately or individual monomers within a multimer can have different orientations, i.e. they can have a complementary arrangement, for example. Inventive cis-regulatory elements of a multimeric form can be functionally linked to one another, i.e. they show in multimeric form a synergistic or antagonistic effect on, for example, the binding capacity of the transcription factor that distinguishes the characteristic core sequence motif of a certain motif group, among other things. The invention thus likewise includes a chimeric promoter that, when induced by a pathogen infection or treatment with a pathogenic elicitor, is suitable for effecting an expression of an operatively linked nucleic acid molecule of interest in a plant cell and which chimeric promoter furthermore comprises a minimal promoter and at least two inventive cis-regulatory elements, wherein the at least two cis-regulatory elements can be present functionally linked in homo- and/or heteromeric form.

Subsequent to pathogen/elicitor contact, the induction of a chimeric promoter comprising at least one multimer of the inventive cis-regulatory elements is at least 2-fold, preferably at least 10-fold or particularly preferably at least 25-fold greater than the induction without pathogen/elicitor contact (background activity).

In a preferred exemplary embodiment of the chimeric promoters of the present invention, the distance from minimal promoter and to the first upstream inventive cis-regulatory element is between 0 and 300 base pairs, preferably between 0 and 70 base pairs and particularly preferably less than 10 base pairs. Additionally or alternatively, the distance between two identical monomers of the inventive cis-regulatory elements in a multimeric form is preferably 0 to 10 base pairs. Preferably two separate multimers in a chimeric promoter of the invention are separated by approximately 0 to 50 base pairs.

In experimental analyses, specific combinations of inventive cis-regulatory elements with other inventive cis-regulatory elements or with other known regulatory elements or fragments such as S-box, D-box or Gst1 showed an advantageous and surprising effect with regard to promoter properties such as a low background activity or an especially specific or an especially strong inducibility (up to 183-fold 2×Cis13-2×Cis05). In this case some combinations showed a synergistic effect with regard to a certain promoter property such as, for example, with regard to the induction factor (compare e.g. 2×Cis13-2×Cis05 in parsley, FIGS. 12 and 13), while although some combinations had an antagonistic effect with regard to the induction factor, for example, in this case an especially low background activity nevertheless developed (e.g. 4×Cis05-2×D in sugar beet). The invention furthermore includes all combinations and combination possibilities of the inventive cis-regulatory elements with themselves and with known cis-regulatory elements that have an advantageous synergistic or antagonistic effect on the inducibility of the promoter. Advantageous combinations are those that can be selected from the following group: 4×sCis05, 4×20u_M1_S1, 4×27G-8_M1_S1, 4×38M_M1_S1, 4×18H_M2_S3, 4×18H_M2_S1, 4×GG13_M1_S2, 4×21S_M3_S1, 4×30l-8_M1_S2, 2×Cis02-2×Cis02, 2×Cis02-2×Cis05, 2×Cis02-2×Cis12, 2×Cis02-2×Cis13, 2×Cis02-2×D, 2×Cis02-2×S, 2×Cis02-Gst1, 2×Cis02-2×30l-8_M1_S2, 2×Cis05-2×Cis02, 2×Cis05-2×Cis05, 2×Cis05-2×Cis12, 2×Cis05-2×Cis13, 2×Cis05-2×D, 2×Cis05-2×S, 2×Cis05-Gst1, 2×Cis05-2×30l-8_M1_S2, 2×Cis12-2×Cis02, 2×Cis12-2×Cis05, 2×Cis12-2×Cis12, 2×Cis12-2×Cis13, 2×Cis12-2×D, 2×Cis12-2×S, 2×Cis12-Gst1, 2×Cis12-2×30l-8_M1_S2, 2×Cis13-2×Cis02, 2×Cis13-2×Cis05, 2×Cis13-2×Cis12, 2×Cis13-2×Cis13, 2×Cis13-2×D, 2×Cis13-2×S, 2×Cis13-Gst1, 2×Cis13-2×30l-8_M1_S2, 2×D-2×Cis02, 2×D-2×Cis05, 2×D-2×Cis12, 2×D-2×Cis13, 2×D-2×30l-8_M1_S2, 2×S-2×Cis02, 2×S-2×Cis05, 2×S-2×Cis12, 2×S-2×Cis13, 2×S-2×30l-8_M1_S2, Gst1-2×Cis02, Gst1-2×Cis05, Gst1-2×Cis12, Gst1-2×Cis13, Gst1-2×30l-8_M1_S2, 2×30l-8_M1_S2-2×Cis02, 2×30l-8_M1_S2-2×Cis05, 2×30l-8_M1_S2-2×Cis12, 2×30l-8_M1_S2-2×Cis13, 2×30l-8_M1_S2-2×D, 2×30l-8_M1_S2-2×S, 2×30l-8_M1_S2-Gst1 and 2×30l-8_M1_S2-2×30l-8_M1_S2.

Particularly advantageous combinations having surprising effect with regard to induction factor and activity are listed in Table 3.

The present invention additionally also relates to chimeric promoters that comprise at least one of the above-mentioned combinations of cis-regulatory elements.

In a preferred embodiment of the chimeric promoters of the present invention, the minimal promoter originates, for example, from a CaMV35S promoter, for monocotyledonous plants from, for example, the wheat TaPal promoter (SEQ ID NO: 39), the corn ZmUbiquitin promoter (SEQ ID NO: 40) or the rice OsGns1 promoter (SEQ ID NO: 38), or for dicotyledonous plants from known minimal prow moters (WO 07/147,395). Minimal promoters from other sources can furthermore also be used to construct a chimeric promoter in the sense of the present invention.

A chimeric promoter of the present invention regardless fulfills the essential requirements placed on the stringent expression regulation of a transgene in a genetic engineering approach, e.g. for producing a pathogen-/diseaseresistant plant. The transgene is a nucleic acid molecule of interest, e.g. a heterologous DNA sequence, operatively linked with the chimeric promoter, which transgene codes, for example, for a resistance gene (R gene), an auto-activated resistance gene, an avirulence gene, a different effector, a protein that is toxic to at least one pathogen, signal transduction components, or a protein which when synthesizing phytoalexins codes a double-stranded RNA for forming siRNAs directed against a pathogen or an antimicrobial peptide. Moreover, numerous experiments on parsley (*Petroselinum erispum*), *Arabidopsis thaliana*, wheat (*Triticum* sp.) and sugar beet (*Beta vulgaris*) demonstrated that a chimeric promoter of the present invention functions across species and can be used across species (see, for example 4×Cis05 in parsley, sugar beet, and wheat).

The definition of a family motif for each motif group 1, 5, 11, 12, 21, 21n, and 27 creates possibilities for a person skilled in the art in the construction of chimeric promoters of the present invention. The observed activities of the different members of the motif groups 27 and 12 (FIG. 8) demonstrate that the flanking sequence regions can be used for customized fine-tuning of the desired expression level. This also applies to a species-dependent coordination of the expression level. The family motif reproduces the variation possibilities of individual bases in said flanking regions and thus teaches a person skilled in the art the extent to which the flanking regions can be modified. A person skilled in the art moreover obtains information from the family motif about how strongly conserved individual base positions are within the family motif. Here it can be assumed that the modification of a strongly conserved base has a more marked effect on the resulting properties of the chimeric promoter than a weakly conserved base.

The invention moreover also relates to a recombinant gene comprising a chimeric promoter of the present invention. The recombinant gene is preferably formed such that the chimeric promoter is operatively linked to a nucleic acid molecule, e.g. a heterologous DNA sequence. Such a heterologous DNA sequence codes in particular for a (poly)peptide, a cytotoxic protein (such as Bt toxin, avirulence protein or enzymes such as glucose oxidase that generate reactive α-ygen species), an antibody, an antisense RNA, a sense RNA, a transcription factor, a protease, a nuclease, a lipase, an enzyme inhibitor or a measurable marker (such as luciferase, GFP or β-galactosidase). The last-mentioned marker and other markers known from the prior art can be used in test systems to determine the pathogen specificity of a chimeric promoter of the present invention or to identify effectors that promote or inhibit an induction of the chimeric promoter. Chimeric promoters of the invention can also be used in RNAi-based processes for "gene silencing", wherein the operatively linked nucleic acid molecule of interest such as an anti-sense RNA, for example, codes a sense-RNA or a double-stranded RNA (dsRNA). The RNA molecule can then represent a short nucleotide sequence (generally at least 10 nucleotides, preferably at least 14 nucleotides and optionally up to 100 or more nucleotides long), which short nucleotide sequence is essentially complementary to a specific mRNA sequence and/or to a DNA sequence of a gene of interest. Standard methods of RNAi technology are described in the prior art.

In principle, it is possible to modify the operatively linked coding sequence such that the product of the translation is localized in a desired cell compartment such as nucleus, endoplasmic reticulum, mitochondrium, cytoplasm or vacuole or also extracellularly (apoplastic). Suitable methods for such modification are known to a person skilled in the art from the prior art (Gorlich, Science 271 (1996), 1513-1518; Hicks, Plant Physiol. 107 (1995), 1055-1058; Rachubinski, Cell 83 (1995), 525-528; Schatz, Science 271 (1996), 1519-1526; Schnell, Cell 83 (1995), 521-524; Verner, Science 241 (1988), 1307-1313; Vitale, BioEssays 14 (1992), 151-160).

A recombinant gene of the present invention can be used both alone and as part of a vector. The present invention thus also relates to a vector that comprises the chimeric promoter of this invention or the recombinant gene of the invention. The preferred vector is a plant expression vector that furthermore also preferably comprises a selection marker for plants. Examples of suitable markers have already been specified above. Methods for constructing such vectors are known from the prior art to a person skilled in the art, e.g. described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.V. (1989).

The present invention additionally relates to a prokaryotic or a eukaryotic host cell that comprises a chimeric promoter, an recombinant gene or an inventive vector, wherein the chimeric promoter itself or as part of the recombinant gene or as part of the vector or respectively as part of the chimeric promoter such as a cis-regulatory element is heterologous to the prokaryotic or eukaryotic host cell, thus for example originates from a cell or from an organism having a different genetic background, or is homologous to the prokaryotic or eukaryotic host cell but is localized in a different genetic environment and thus differs from the naturally occurring chimeric promoter or its part.

The chimeric promoter, the recombinant gene or the inventive vector can either be integrated in the genome of the prokaryotic or eukaryotic host cell, preferably stably integrated, or can remain in an extrachromosomal form such as a plasmid in the cell.

The invention moreover provides a method for producing a transgenic plant, which method includes introducing a chimeric promoter, a recombinant gene or a vector according to the present invention into at least one cell of the plant or said method includes introducing a chimeric promoter, a recombinant gene or a vector according to the present invention into at least one plant cell in a cell culture from which the transformed or transgenic plant is subsequently regenerated. The chimeric promoter, the recombinant gene or the vector is preferably integrated, especially preferred stably integrated, into the genome of the plant. The nucleic acid molecule can be connected to additional regulatory sequences like the 3' end to a poly-A tail for the expression of the nucleic acid molecule of interest in plant cells under the control of a chimeric promoter according to the present invention. Methods for introducing genes or genetic material into a plant or into a plant cell as well as methods for regenerating transformed plant cells are known from the prior art, for example *Agrobacterium tumefaciens-* or *Agrobacterium rhizogenes*-conveyed transformation of plant cells or tissues with T-DNA, die protoplast fusion, injection, electroporation, vacuum infiltration or biolistic methods. Methods for preparing suitable vectors for introducing genes or genetic material into a plant or into a plant cell are likewise routine for a person skilled in the art (Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.V. (1989)).

In an alternative embodiment, a plant cell can be modified such that said plant cell expresses an endogenous gene under the control of an inventive chimeric promoter or under the control a native promoter of the endogenous gene, which native promoter was modified by inventive cis-regulatory elements. Introducing such a chimeric promoter, which naturally does not regulate the expression of a certain gene or of a certain genomic sequence, at the desired location in the plant genome or the introduction of inventive cis-regulatory elements into a native promoter can be effected using known standard methods such as targeted integration ('gene targeting') via zinc finger-nucleases (Urnov et al., Nature Reviews 2010_Genome editing with engineered zinc finger nucleases; Townsend et al., Nature 2009_High-frequency modification of plant genes using engineered zinc-finger nucleases) or TAL effector nucleases (WO 2010/079430; WO 2011/072246). The modification of a native promoter of an endogenous gene also means the additional introduction of an inventive cis-regulatory element into the native promoter, which already naturally has an inventive cis-regulatory element, and thus a multimerization of present cis-regulatory elements. Such a modified promoter can, compared to the native version, have changed properties with regard to specificity, expression level or background activity, for example.

Using known methods, modified plants can be regenerated from the modified plant cells.

The invention thus relates again to transgenic (transformed) plants dew scribed below, which plants were transformed with a chimeric promoter, a recombinant gene, a vector according to the present invention, and described plants modified by introducing at least one inventive cis-regulatory element or an inventive chimeric promoter. Transgenic or modified plants can come from any desired plant species. They can be monocotyledonous, dicotyledonous or angiosperm plants, preferably belonging to plant species of agricultural or horticultural interest, for example corn, rice, wheat, rye, barley, oats, sorghum, potatoes, oilseed rape, sunflower, soybean, cotton or sugar beet.

In a preferred embodiment of the invention, a transgenic or modified plant is resistant or demonstrates an increased resistance to one or more pathogens in comparison to a non-transgenic or non-modified plant of the same species (wild type).

Included in the present invention are furthermore a plant part, a plant tissue, a plant cell or a seed of the transgenic and of the modified plant of the present invention, wherein said plant part, plant tissue, plant cell or seed likewise has the transgene introduced into the plant or the introduced modification.

Embodiments of the present invention are described by way of example with reference to the accompanying figures and sequences:

FIG. 1: The plasmids including 2×Cis05 element and the multimerized 4×Cis05 element are shown as an example of cloning the single sequences as chimeric promoters. The plasmids are derived from pBT10-GUS (Sprenger and Weisshaar (2000): The Plant Journal 22, 1-8). The structure of the other plasmids is in accordance therewith. Amp: ampicillin resistance; WRKY30-Cis05: doubled single sequence Cis05. 35S-minimal: 35S-minimal promoter; Luc-m3: luciferase reporter gene; pAnos: NOS terminator.

Figure 2:
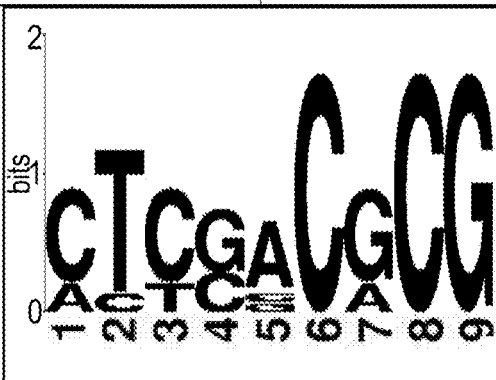
Figure 2:
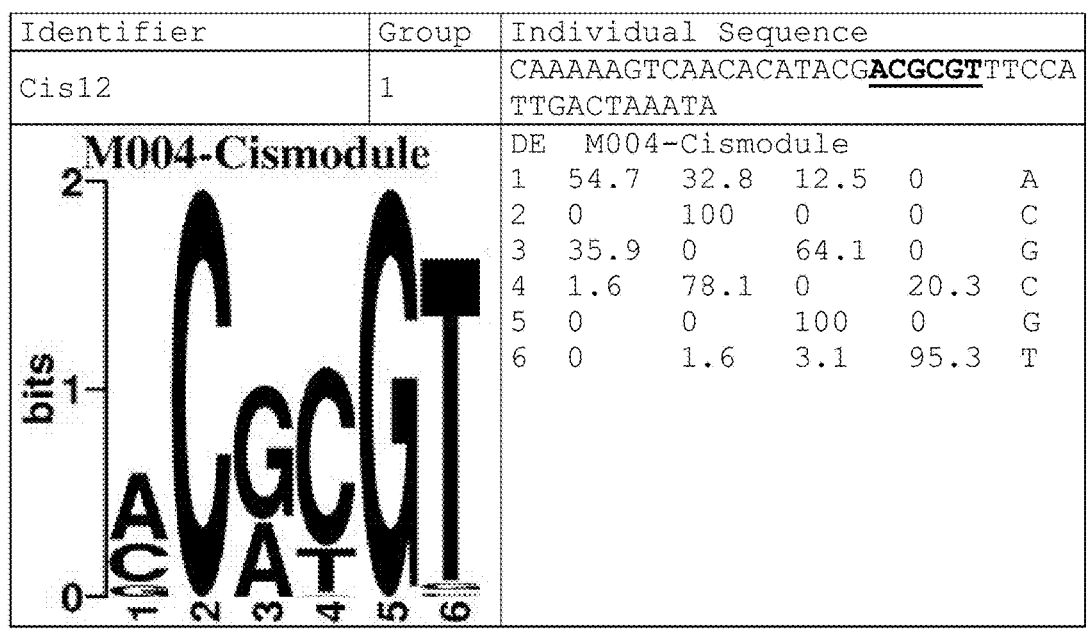
Figure 2:
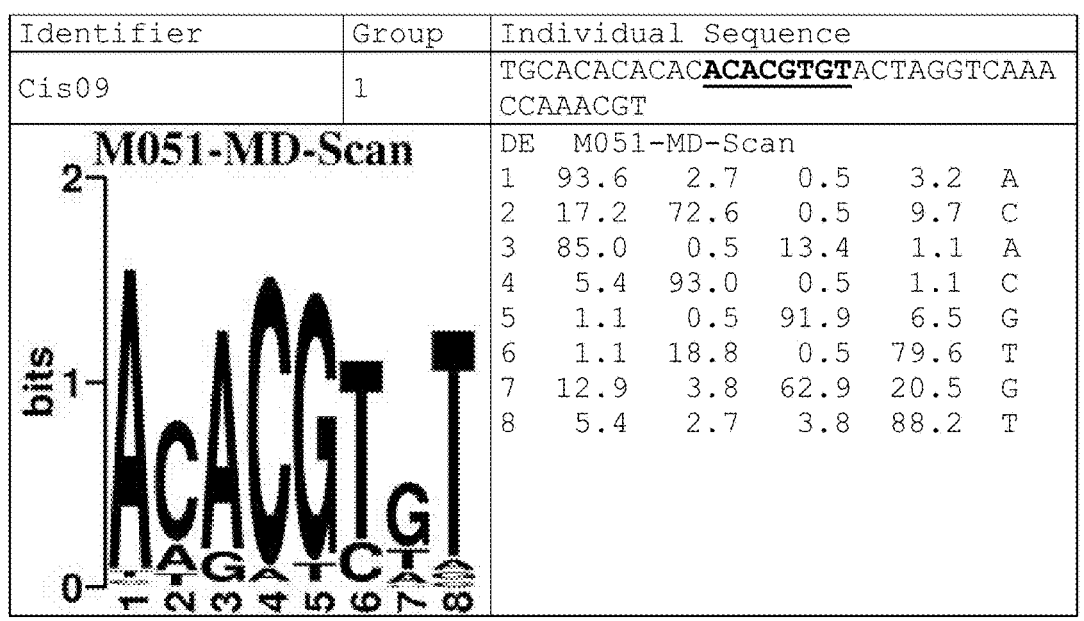
Figure 2:
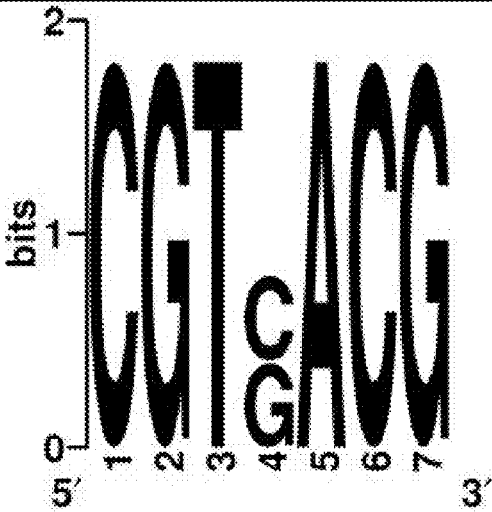
Figure 2:
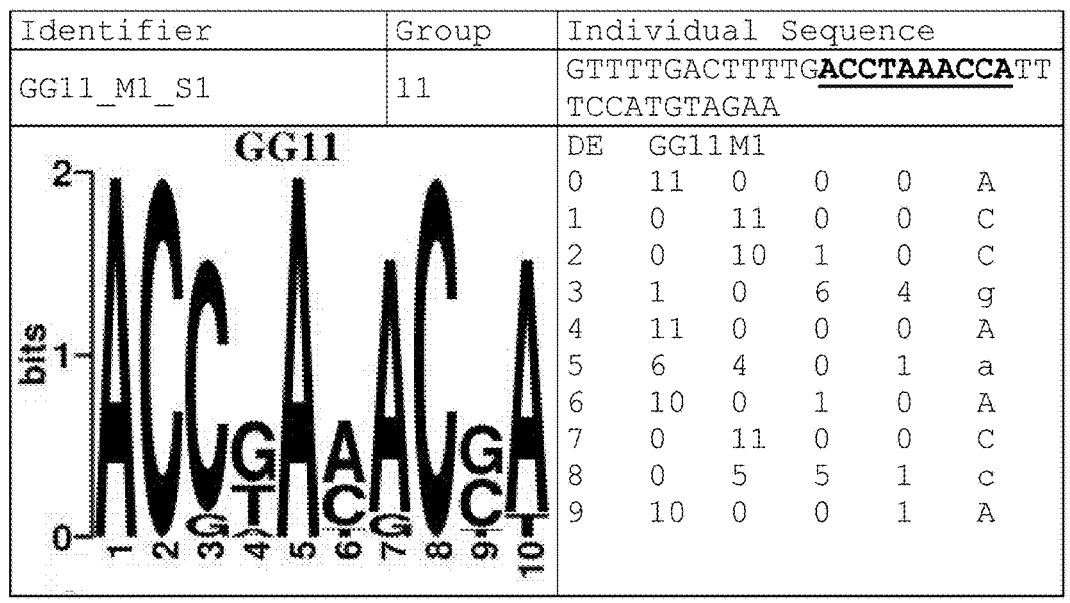
Figure 2:
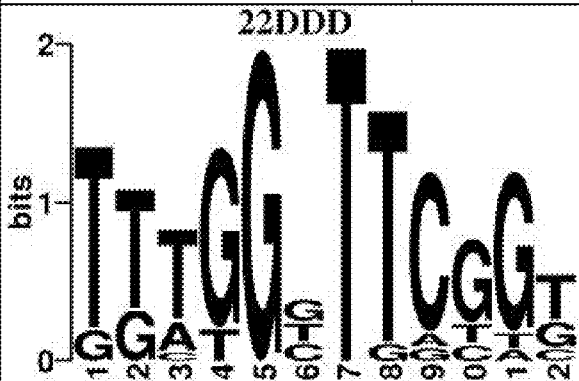
Figure 2:
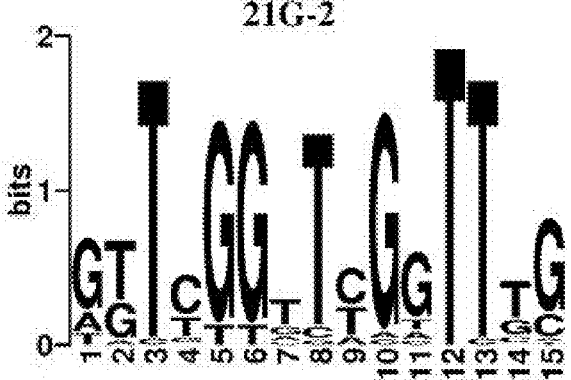
Figure 2:
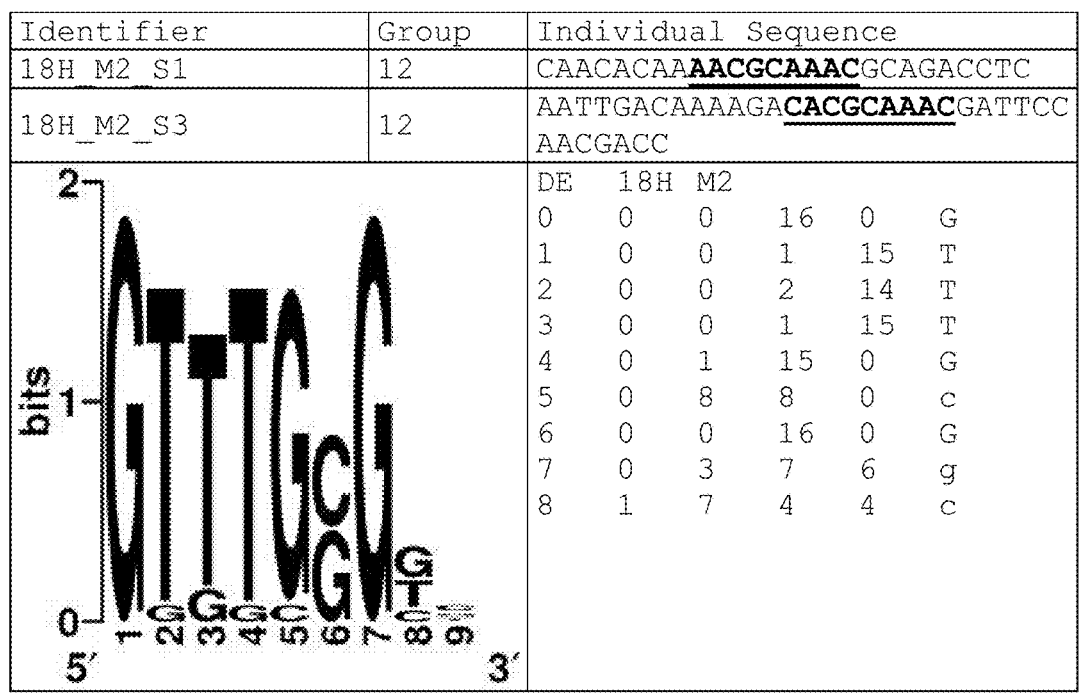
Figure 2:
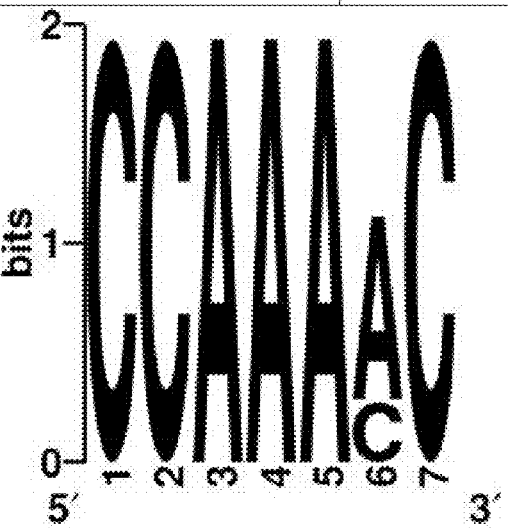
Figure 2:
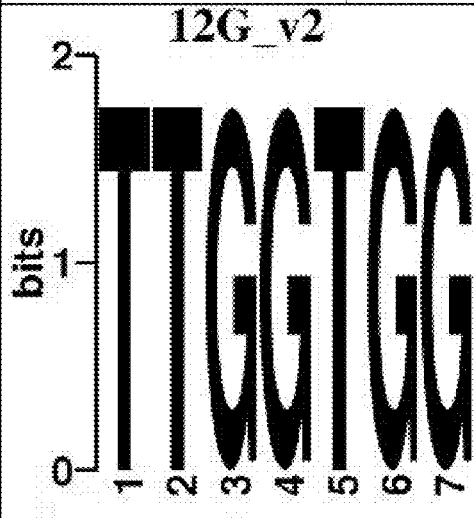
Figure 2:
Figure 2:
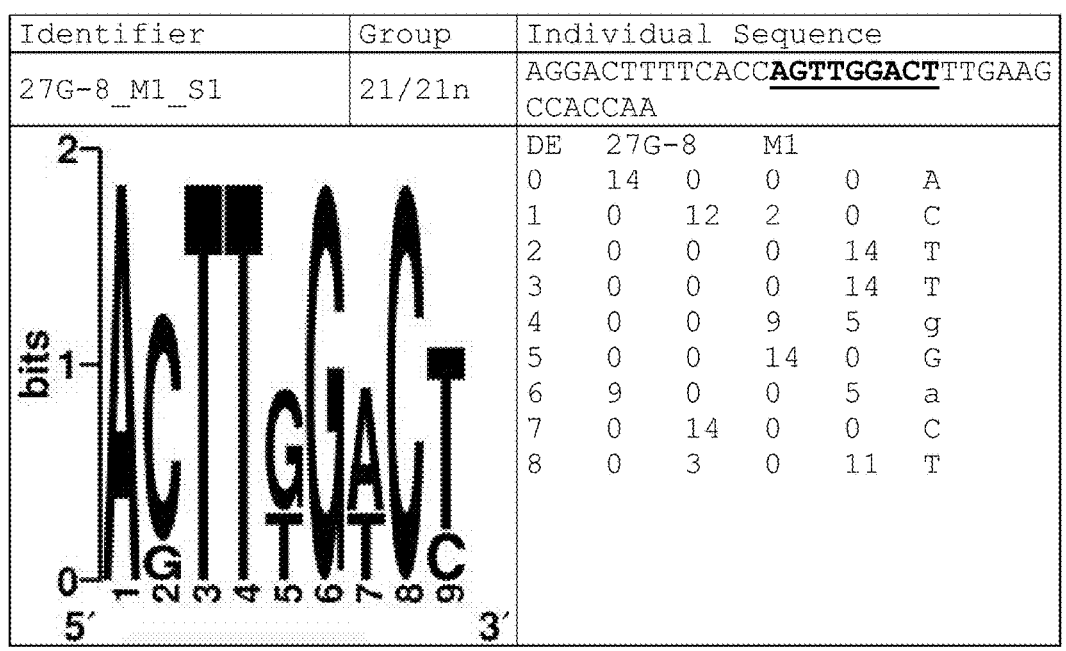
Figure 2:
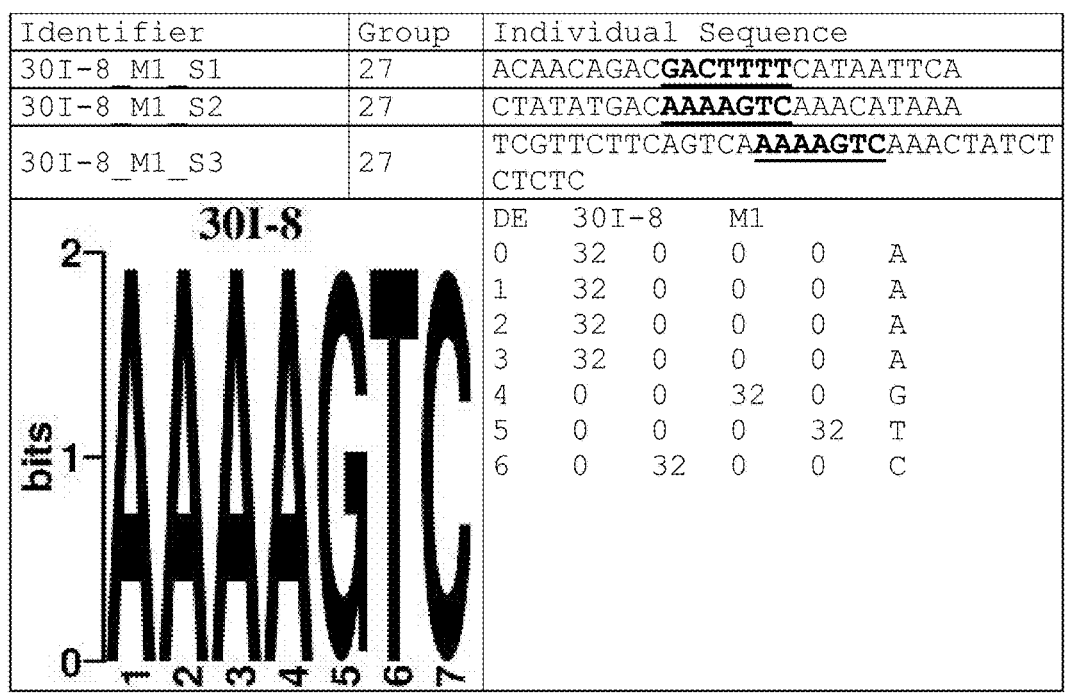
Figure 2:
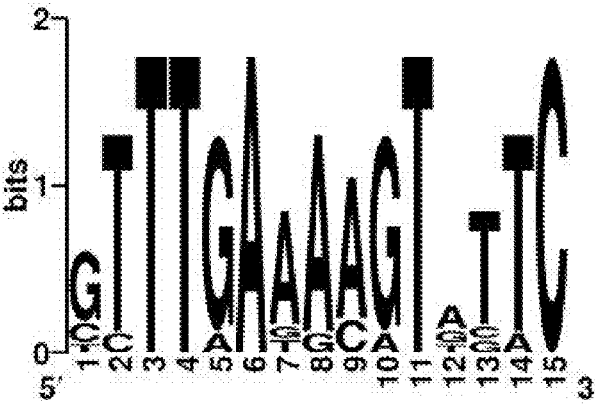
Figure 2:
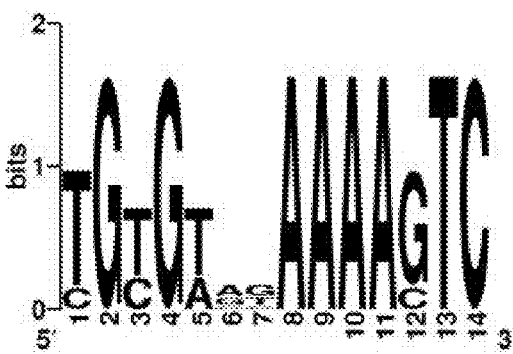
Figure 2:
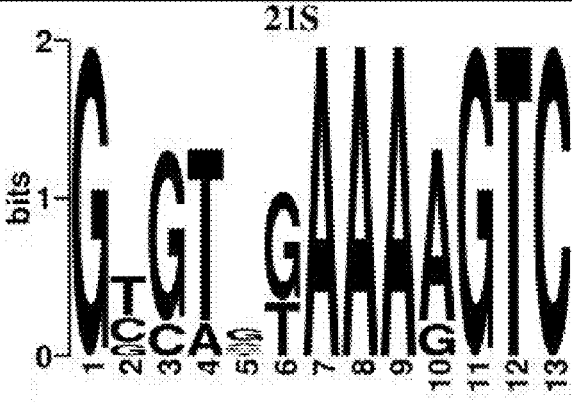
Figure 2:
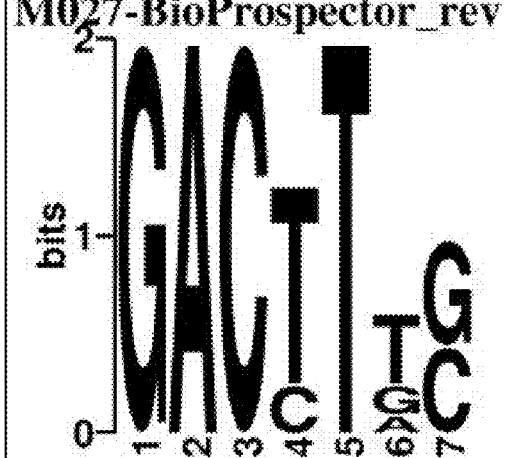
Figure 2:
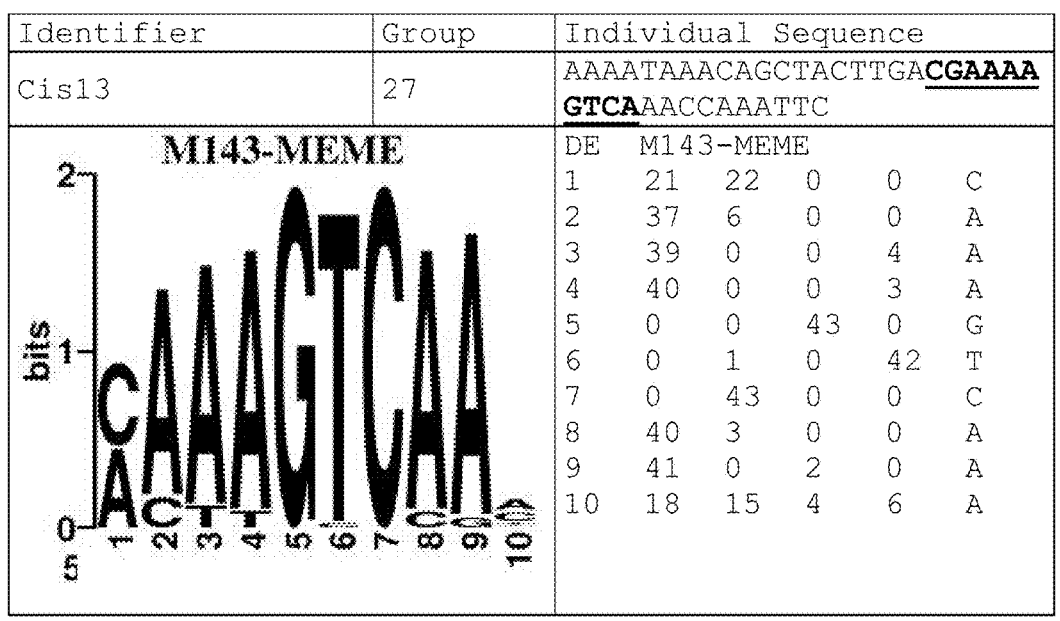
Figure 2:
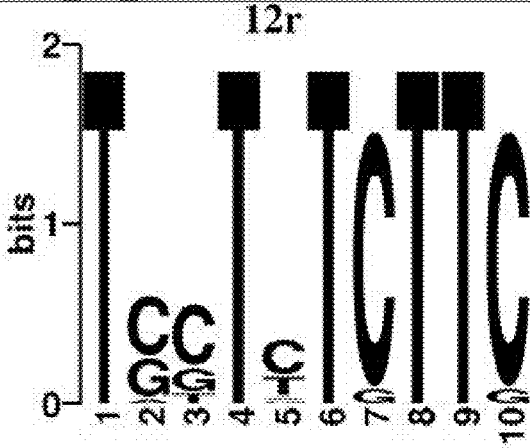
Figure 2:
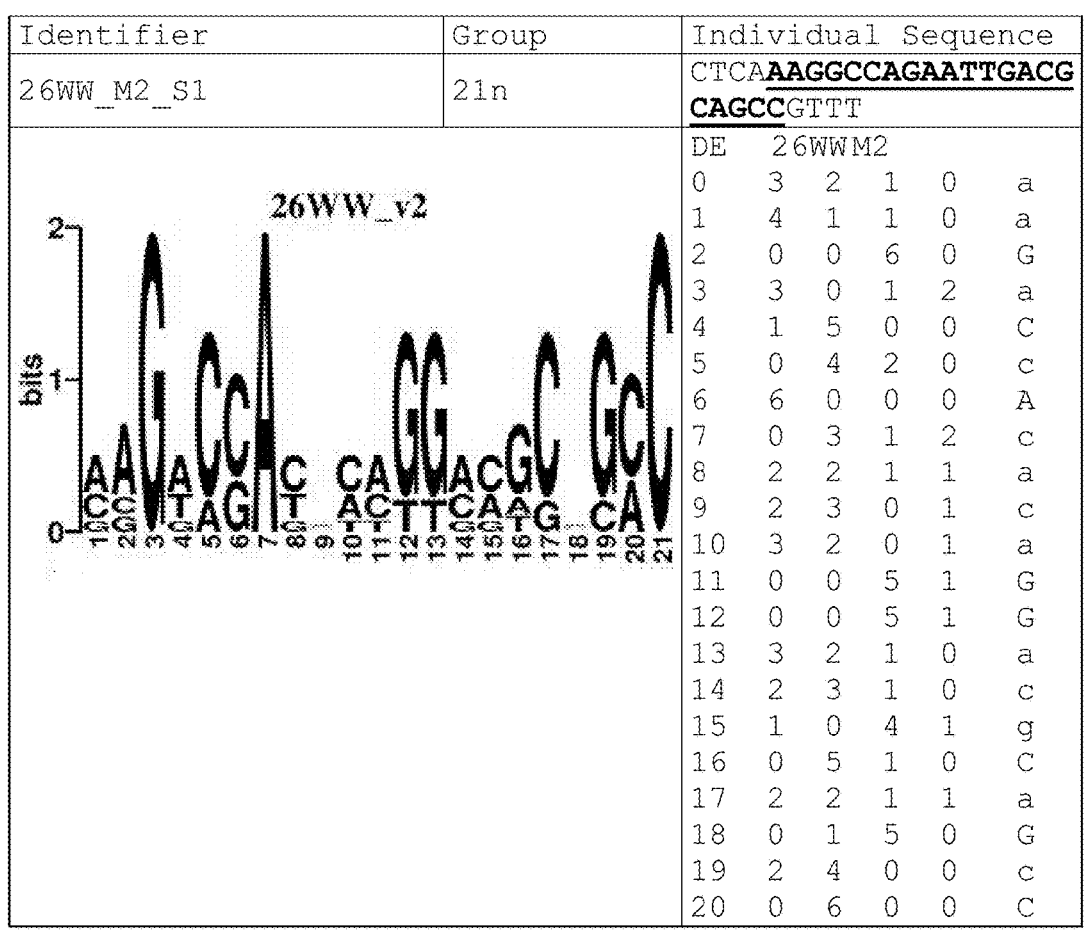
Figure 2:
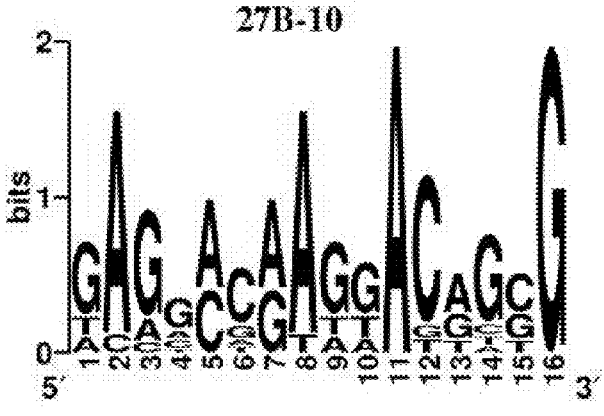

FIG. 2: Species-wide pathogen-inducible single sequences (A-X). The upper lines respectively reflect the identifier of the single sequence, the motif group, and the single sequences themselves. The core sequences of the motif that led to the selection of the single sequence is written in boldface type and underlined. Therebeneath are respectively reflected the motif logo of the underlying bioinformatically identified motif and its matrix. If more than one single sequence of a motif was tested, they are summarized. FIG. 2A discloses SEQ ID NO: 26; FIG. 2B discloses SEQ ID NO: 25; FIG. 2C discloses SEQ ID NO: 24; FIG. 2D discloses SEQ ID NOS 30-31; FIG. 2E discloses SEQ ID NO: 32; FIG. 2F discloses SEQ ID NO: 19; FIG. 2G discloses SEQ ID NO: 16; FIG. 2H discloses SEQ ID NO: 17; FIG. 2I discloses SEQ ID NO: 18; FIG. 2J discloses SEQ ID NOS 20-21; FIG. 2K discloses SEQ ID NO: 22; FIG. 2L discloses SEQ ID NO: 23; FIG. 2M discloses SEQ ID NO: 33; FIG. 2N discloses SEQ ID NO: 27; FIG. 2O discloses SEQ ID NO: 28; FIG. 2P discloses SEQ ID NOS 7-8 and 12; FIG. 2Q discloses SEQ ID NO: 9; FIG. 2R discloses SEQ ID NO: 10; FIG. 2S discloses SEQ ID NO: 11; FIG. 2T discloses SEQ ID NOS 13-14; FIG. 2U discloses SEQ ID NO: 15; FIG. 2V discloses SEQ ID NO: 34; FIG. 2W discloses SEQ ID NO: 42; and FIG. 2X discloses SEQ ID NO: 43.

Figure 3:
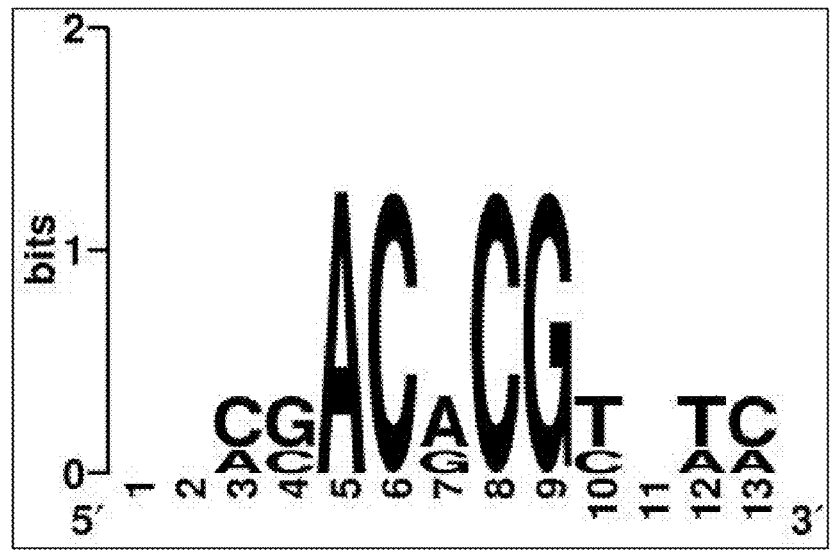
Figure 3:
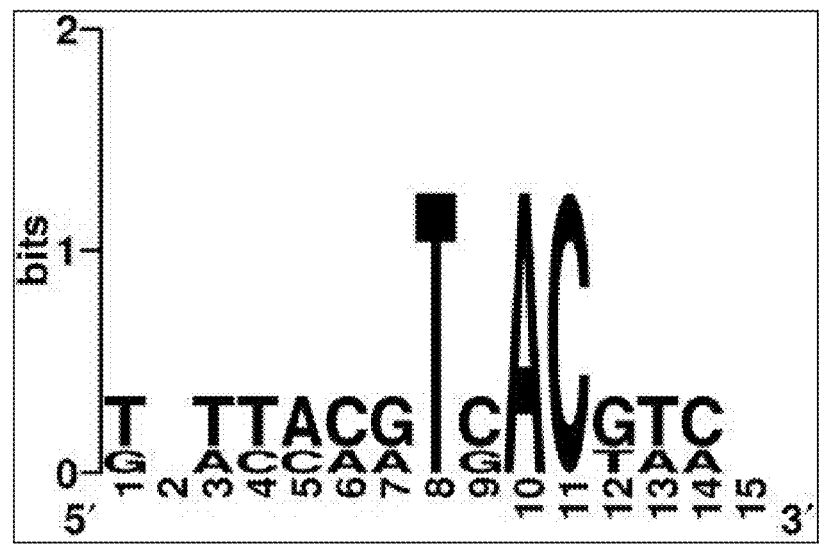
Figure 3:
Figure 3:
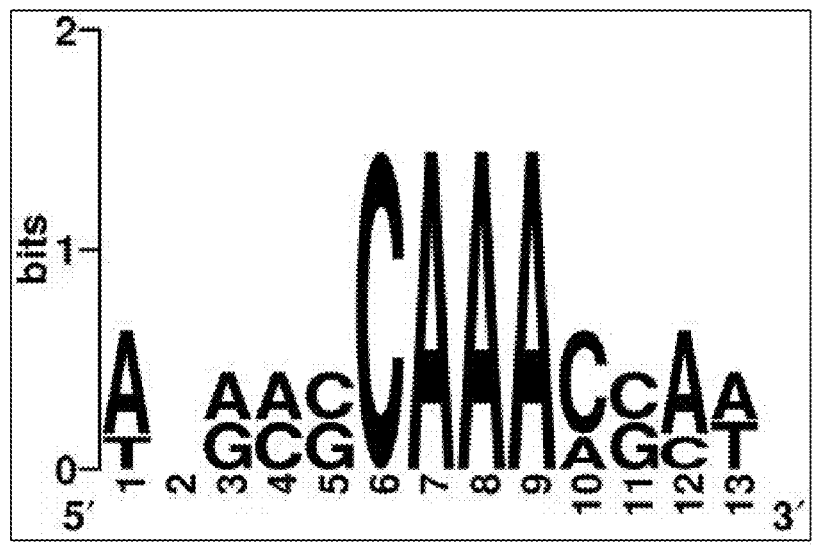
Figure 3:
Figure 3:
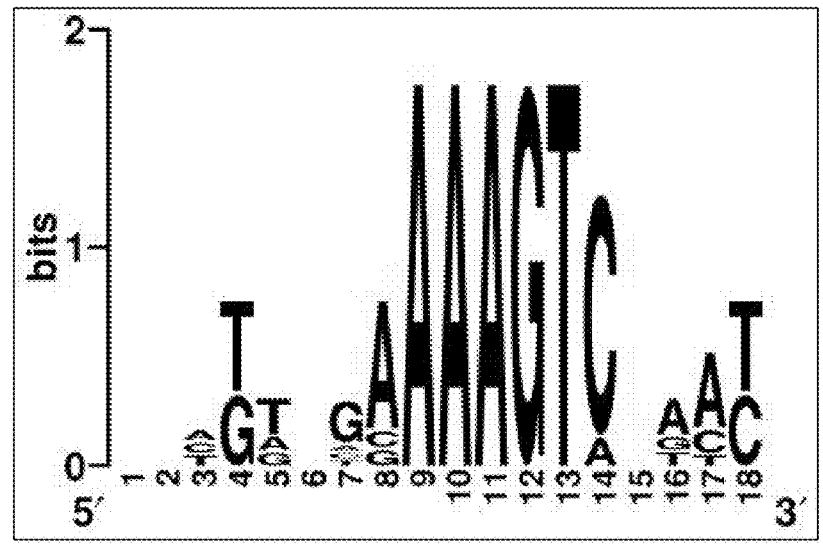
Figure 3:
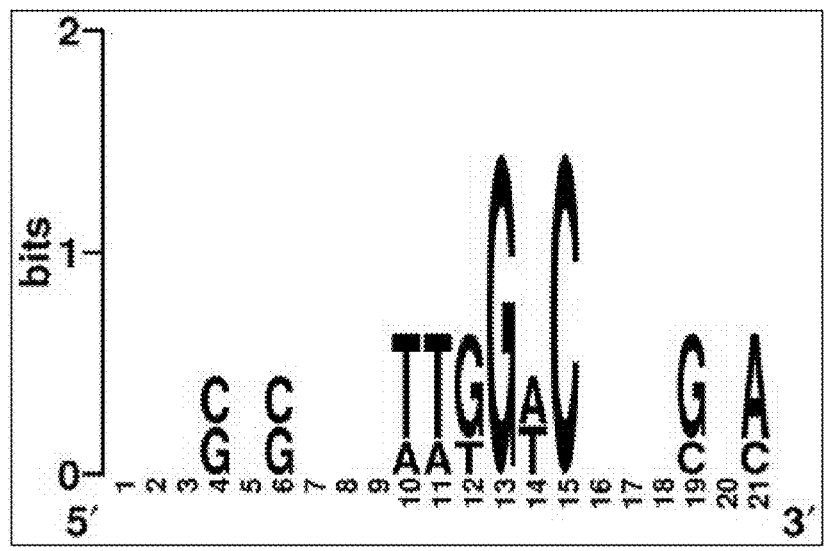

FIG. 3: Summary of all single sequences of a motif group, which sequences tested positive, and representation of the sequence- and family-motifs derived therefrom (FIG. 3 A-G). The respective motif group is specified in the top line. An alignment of all single sequences that tested positive is shown therebeneath, which alignment includes at least the core sequences and, if present, additional conserved bases. The bases, from which the core sequence motif is derived, are surrounded by a border. FIG. 3A discloses SEQ ID NOS 89-91; FIG. 3B discloses SEQ ID NOS 92-94; FIG. 3C discloses SEQ ID NOS 95 and 95-97; FIG. 3D discloses SEQ ID NOS 98-101; FIG. 3E discloses SEQ ID NOS 102-103; FIG. 3F discloses SEQ ID NOS 104-108, 106 and 109-111; and FIG. 3G discloses SEQ ID NOS 112-115.

Figure 4:
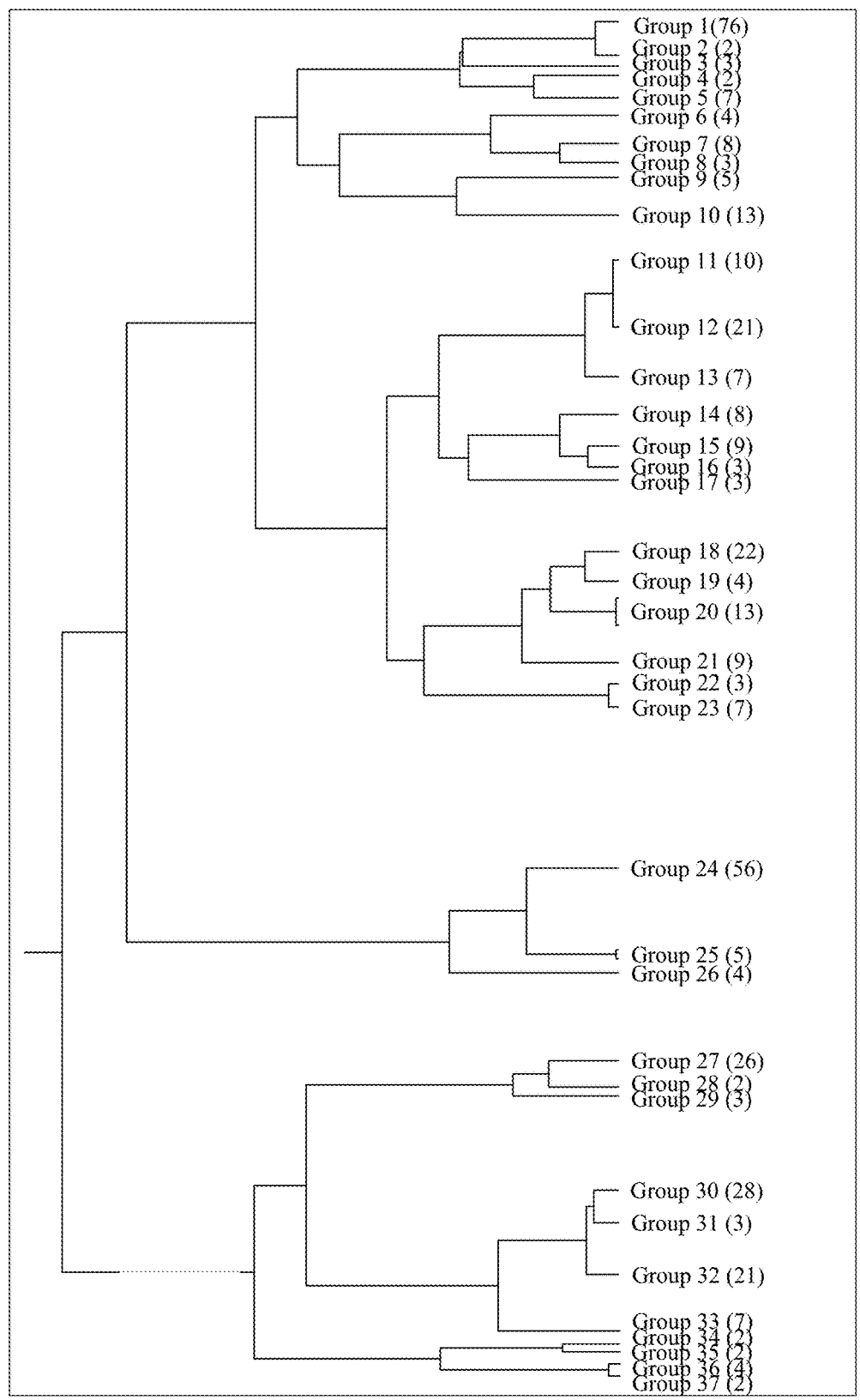

FIG. 4: Phylogenetic tree of the identified motif groups. The phylogenetic tree was generated via a cluster analysis using the STAMP web server. The number of the motifs contained in the motif group is surrounded by parentheses behind the number of the motif group.

Figure 5:
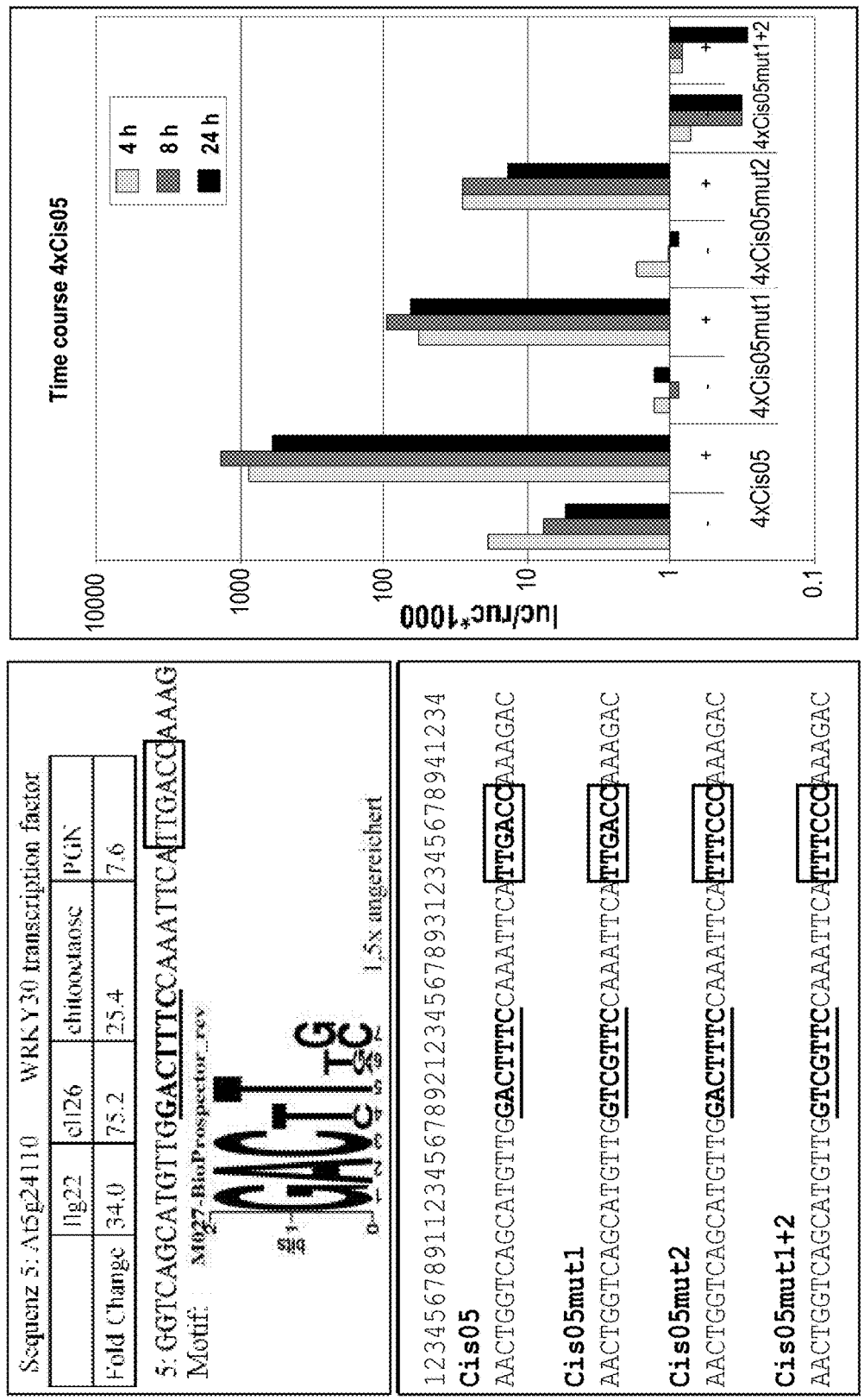
Figure 5:
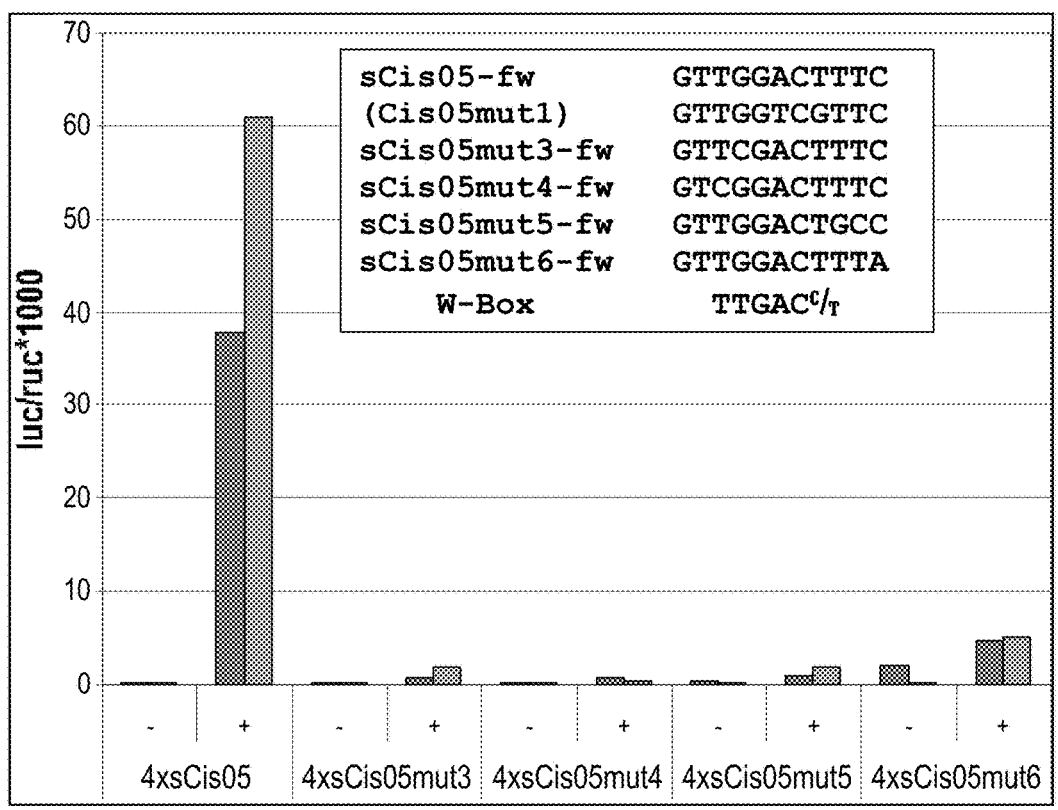

FIG. 5: A) Mutagenesis of the Cis05-single sequence. The sequence used contains both the Cis05 motif (bold-face, underlined) and a W-box (bold-face and surrounded by a border). Mutations were introduced in both motifs. As described, parsley assays were conducted on induction with the tetramerized mutated derivatives using the PAMP PEP25. The PAMP-induced activity of the chimeric promoters was measured after 4, 8, and 24 hours (right-hand side). Mutations in the Cis05-motif (Cis05mut1) and in the W-box (Cis05mut2) lead to a significant decline of the induced activity. Only when both motifs are mutated (Cis05mut1+2) is there a complete loss of inducibility. B) sCis05 is a shortened variant of Cis05 containing only the Cis05 motif and the W-box no longer. The PEP25 inducibility of sCis05 and mutated derivatives was tested as described in 5A. Both bars represent two biological replicates (independent transformations). For guidance, the W-box consensus is shown beneath the sCis05 derivatives. FIG. 5A discloses SEQ ID NOS 14 and 116-119, respectively, in order of appearance. FIG. 5B discloses SEQ ID NOS 44 and 120-124, respectively, in order of appearance.

FIG. 6 A: Elicitor-responsive reporter gene expression of the chimeric promoters 4×30l-8_M1_S2 and 4×18H_M2_S1 with mutations in the single sequences. The mutated bases are underlined. Elicitation was effected by PEP25 in parsley protoplasts. The nucleotide sequences of the mutated derivatives of the single sequences are shown beneath the diagrams as +, with elicitor PEP25; –, without elicitor. 2S2D: Positive control; MS23GUS: negative control (empty vector). FIG. 6A discloses SEQ ID NOS 8, 125-127, 20, and 128-130, respectively, in order of appearance. FIG. 6B discloses SEQ ID NOS 131-137, respectively, in order of appearance.

FIG. 6 B: Elicitor-responsive reporter-gene expression of the chimeric promoters 4×20u_M1_S1 and 4×27G-8_M1_S1 with mutations in the single sequences. The mutated bases are underlined. Elicitation was effected by PEP25 in parsley protoplasts. The nucleotide sequences of the mutated derivatives of the single sequences are shown beneath the diagrams.

Figure 7:
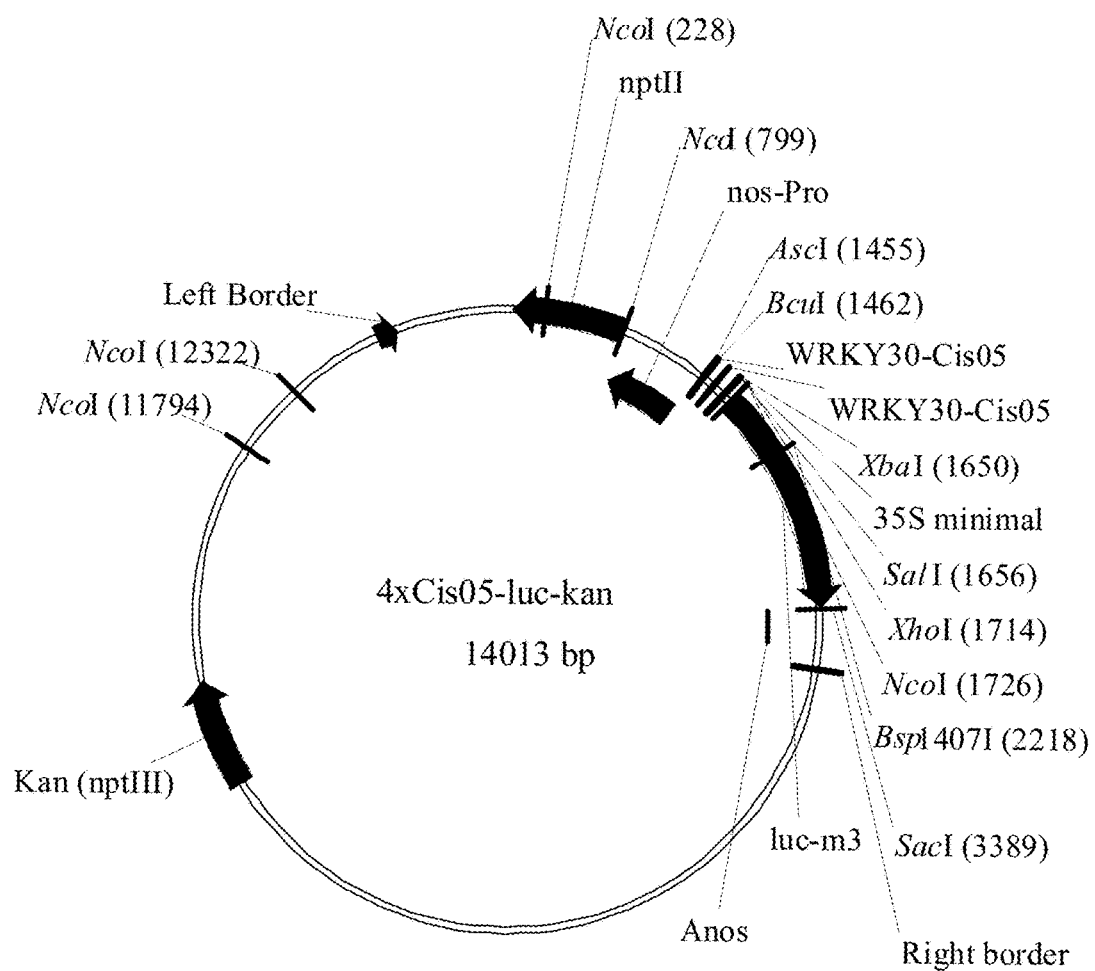

FIG. 7: Binary vector for the transformation of the luciferase reporter gene under the control of the chimeric promoters in sugar beet. The vector with the chimeric promoter 4×Cis05 is shown as an example. nptII: kanamycin resistance; WRKY30-Cis05: double single sequence Cis05. 35S minimal: 35S minimal promoter; luc-m3: luciferase reporter gene; Anos: Nos terminator.

Figure 8:
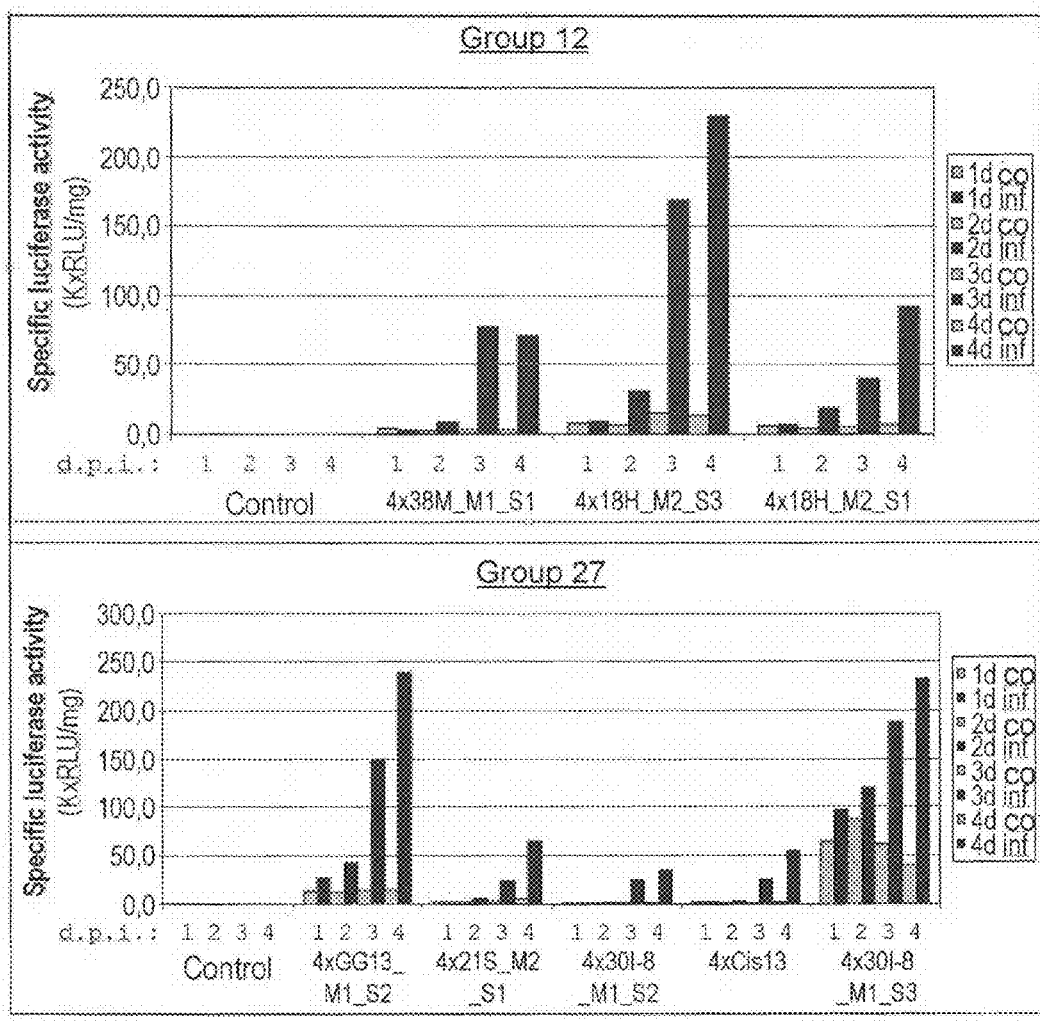
Figure 8:
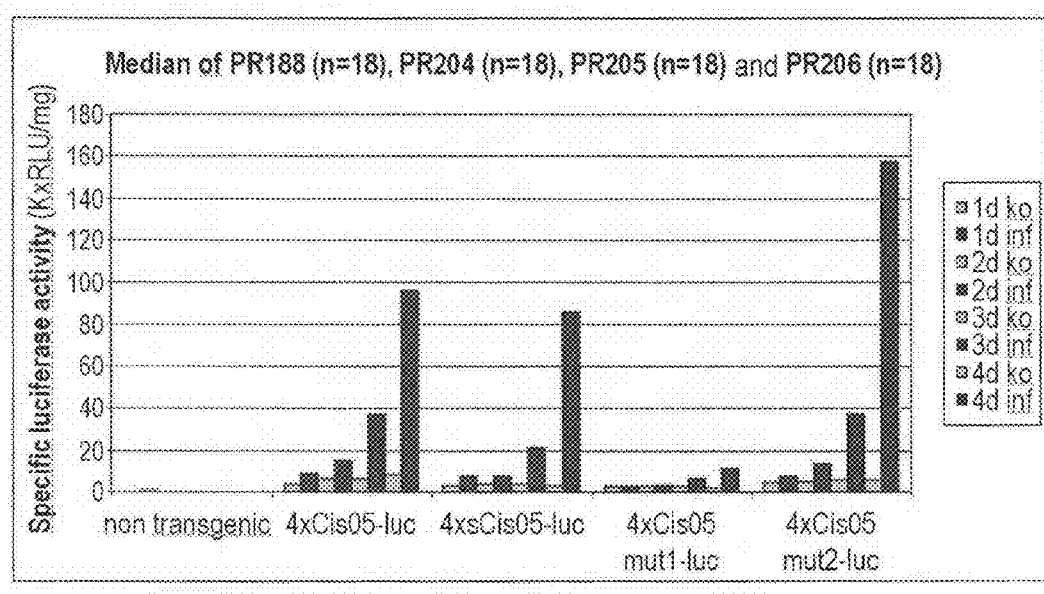

FIG. 8 A: *Cercospora beticola* induced promoter activity in stably transformed sugar beets. Of the constructs given, the luciferase activity subsequent to *C. beticola* infection of in-vitro plants was determined for a plurality of independent transformants (4 replicas per transformant and point in time). The median was calculated from the measured values obtained. The top diagram summarizes the results for single sequences from the motif group 12, while the bottom diagram summarizes the results for elements from the motif group 27. Co: Control (mock infection); inf; infection with *C. beticola;* 1d-4-d: days post inoculation (d.p.i.). Control: Non-transgenic plants.

FIG. 8 B: *Cercospora beticola*-induced promoter activity of 4×Cis05 and its derivatives in stably transformed sugar beets. For 4×Cis05 and its derivatives the luciferase activity after *C. beticola* infection was determined in a plurality of independent transformants (4 replicas per transformant and point in time). The median was calculated from the measured values obtained. The sequence of the different derivatives is given in FIGS. 5A and 5B. For each of the different derivatives, it is additionally indicated under the diagram whether the derivative contains the Cis05 motif or the W-box. Co: Control (mock infection); inf; infection with *C. beticola;* 1d-4-d: days post inoculation (d.p.i.) non transgenic: non-transgenic control.

Figure 9:
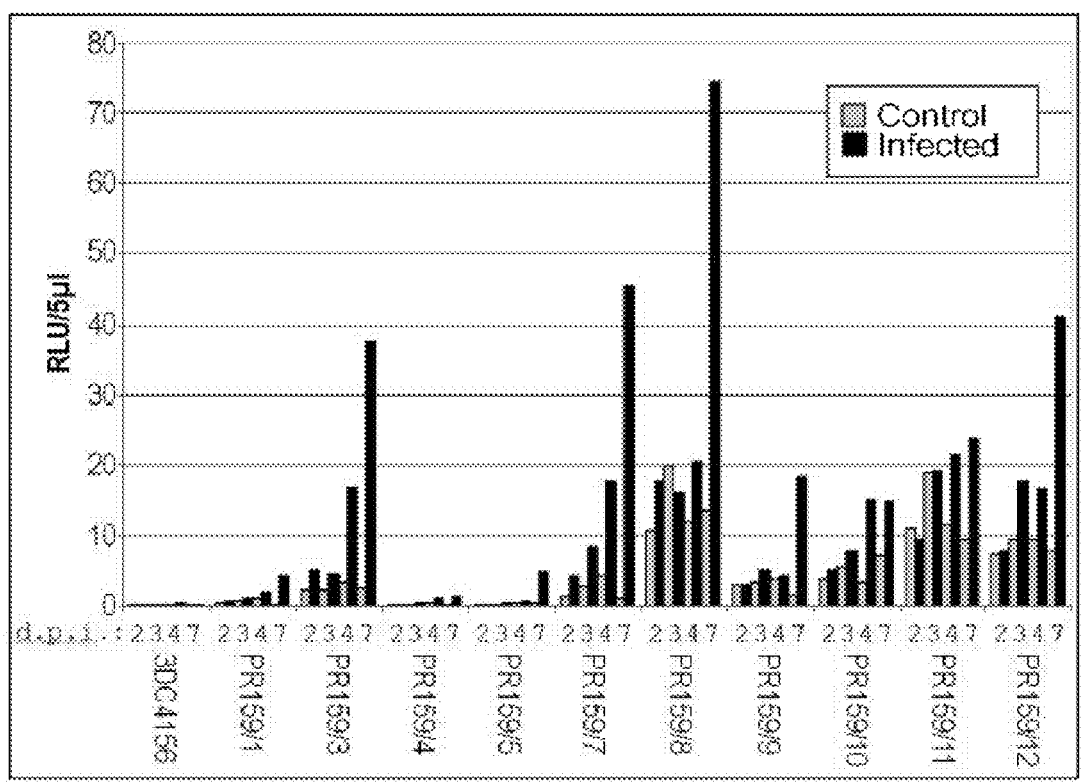

FIG. 9: *Cercospora beticola*-induced promoter activity of the chimeric promoter 4×GG6_M1_S1 in stably transformed sugar beets. The luciferase activity after *C. beticola* infection of in-vitro plants was determined for 10 independent transformants with the construct 4×GG6_M1_S1-luc (4 replicas per transformant and time period). Co: Control (mock infection); inf; infection with *C. beticola;* 2d, 3d, 4d and 7d: days post inoculation (d.p.i.).; 3DC4156: Non-transgenic control plants.

Figure 10:
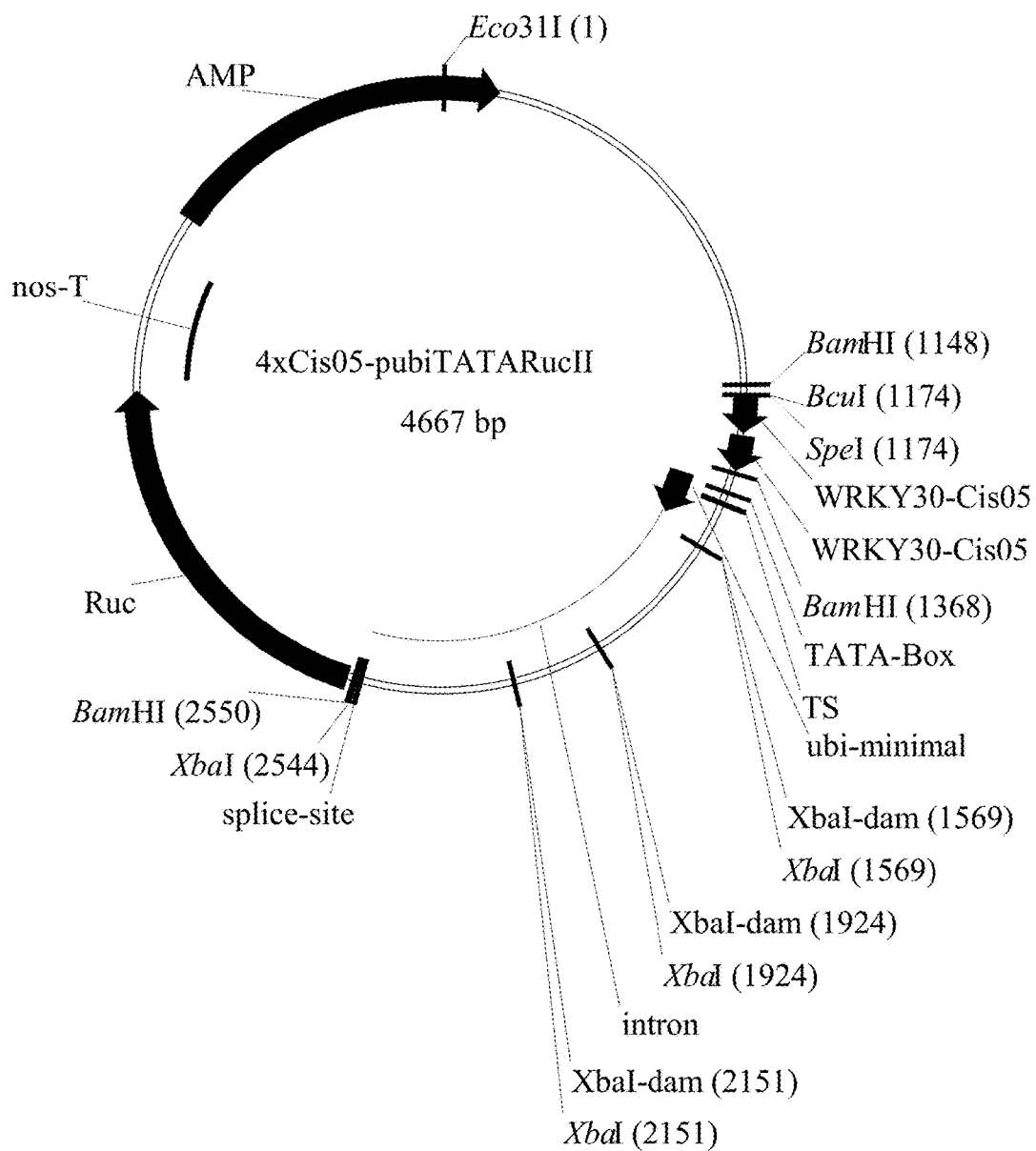

FIG. 10: Plasmid card of the plasmids used for the transient tests in wheat. The plasmid with the chimeric 4×Cis05 promoter is shown as an example. Ruc: *Renilla-luciferase* reporter gene. AMP: Ampicillin resistance. WRKY30-Cis05: Double single sequence Cis05.

Figure 11:
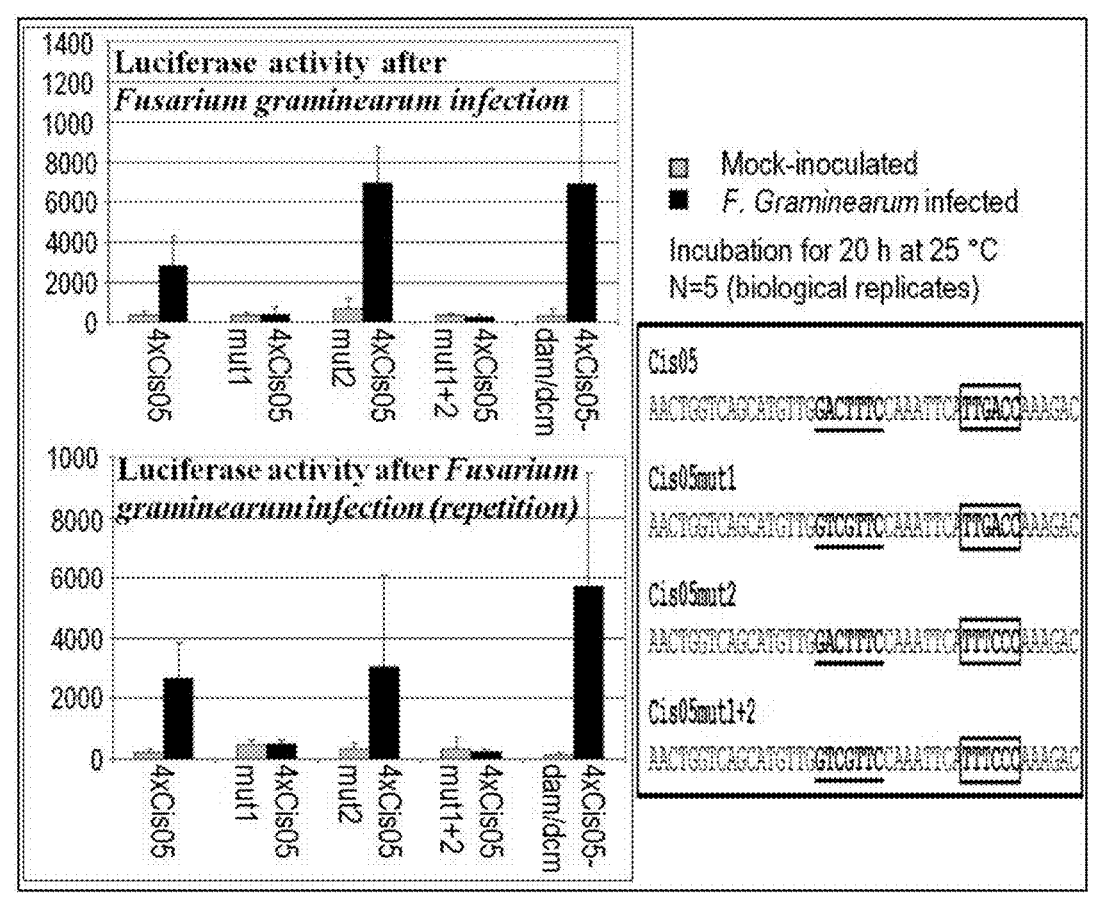

FIG. 11: Test of the induction by *Fusarium* of the chimeric promoter 4×Cis05 and its mutated derivatives with mutations in the Cis05 motif (Cis05mut1), the W-box (Cis05mut2) or in both motifs (Cis05mut1+2). The corresponding constructs were transiently transformed in wheat and the luciferase activity was measured 20 hours post incubation with *Fusarium*. 4×Cis05-dam/dcm identifies an experiment in which the plasmid DNA of a non-methylated *E. Coli* strain was used to exclude an induction by dam/dcm-methylated DNA (likewise a potential PAMP). If the core sequence of Cis05 mutated, the inducibility is entirely lost. In contrast, the mutation in the W-box has no effect. The sequences of Cis05 and its mutated derivatives are reproduced on the right-hand side. Mutated bases are highlighted in red. FIG. 11 discloses SEQ ID NOS 116-117, respectively, in order of appearance.

Figure 12:
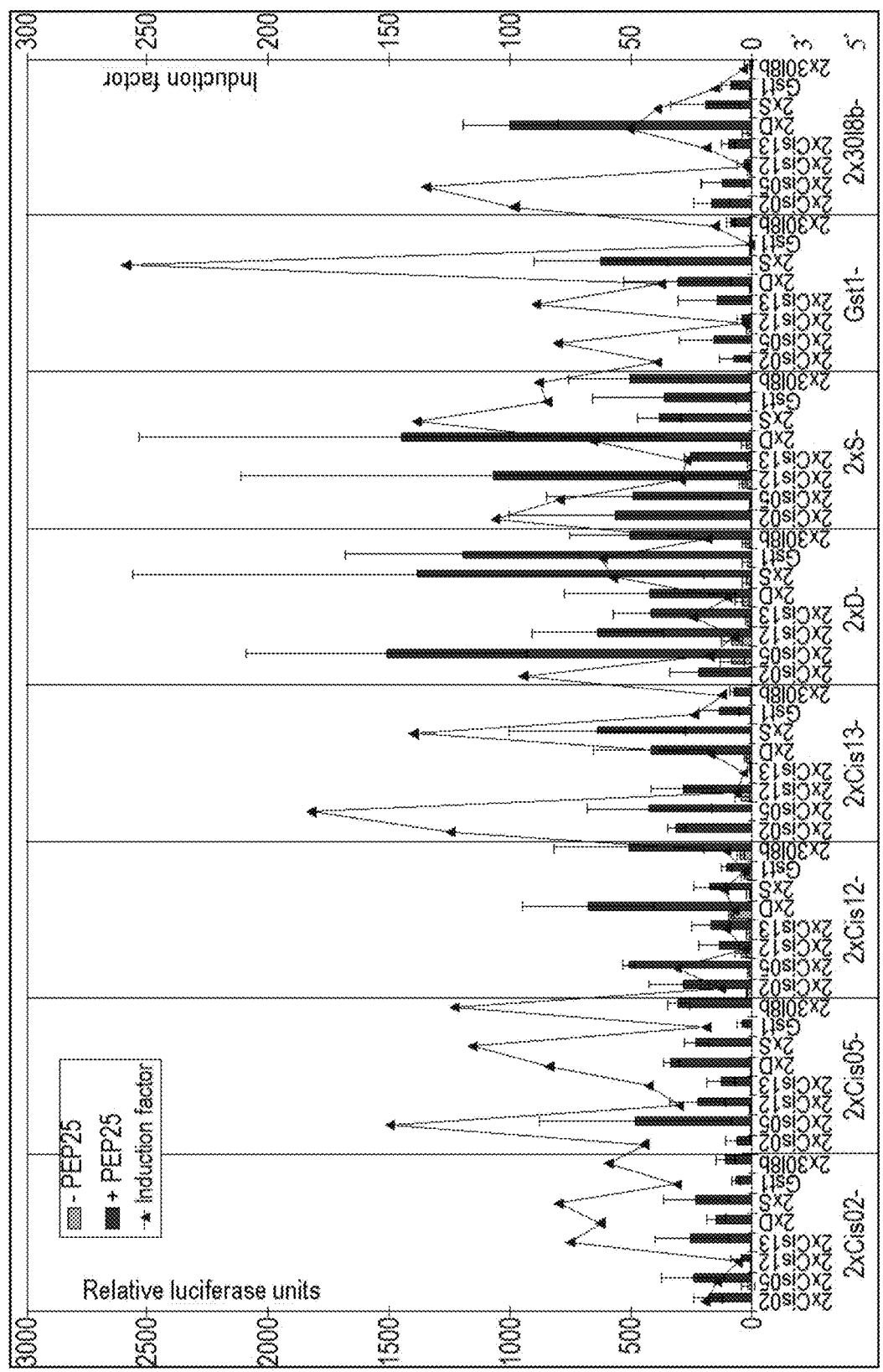

FIG. 12: Induced and non-induced activity of the chimeric combinatorial promoters after PEP25 induction in parsley. The tests were conducted in three biological replicates; the blue line reproduces the induction factor. In the bottom row beneath the diagram, the elements in 5' position are given, while in the top row the elements in 3' position are given. 3018b is a different identifier for the single sequence 30l-8_M1_S2.

Figure 13:
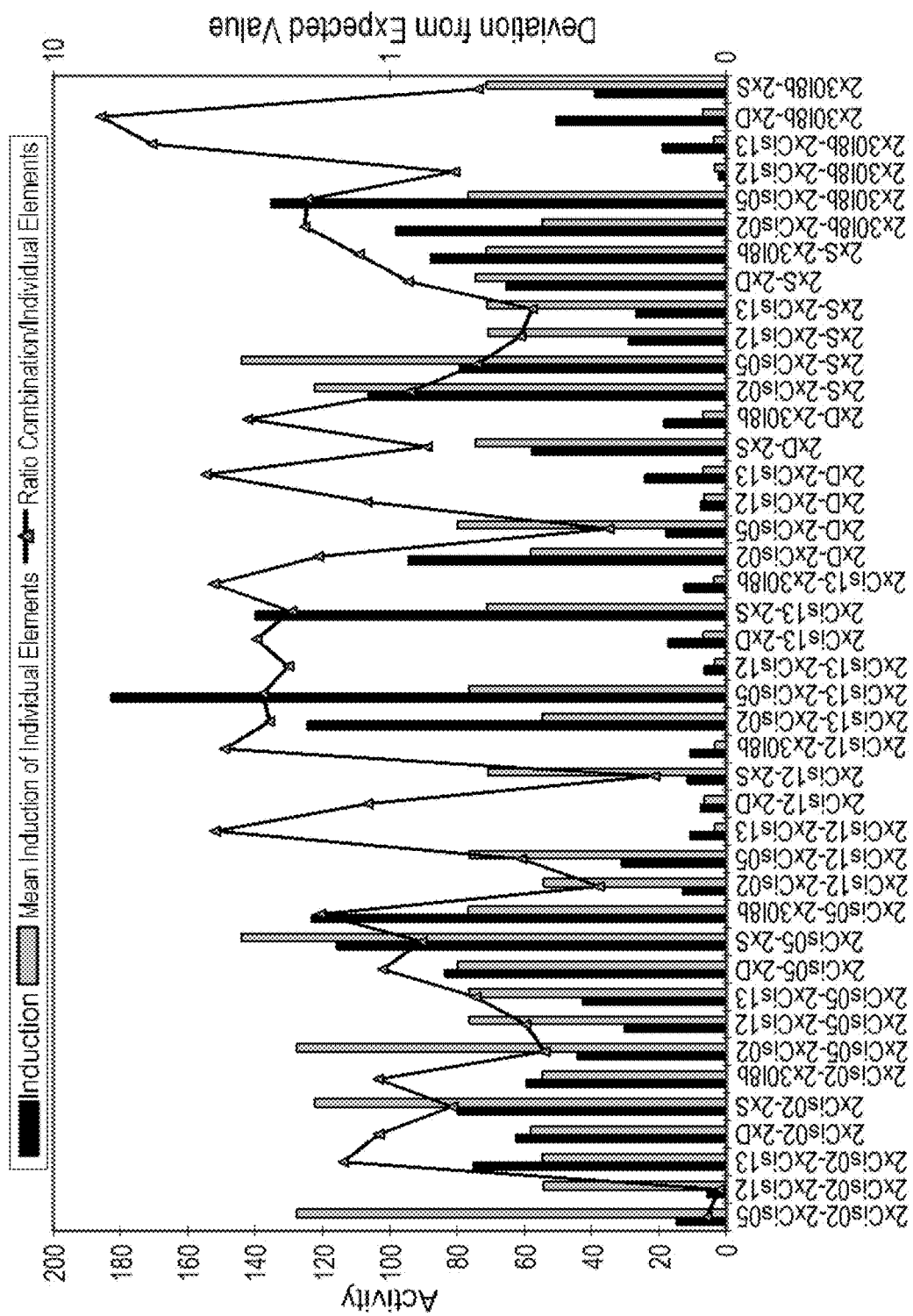

FIG. 13: Synergistic and antagonistic interactions of single sequences in the chimeric combinatorial promoters after PEP25 induction in parsley. The actual measured induction factor is reproduced in violet, while the expected induction factor based on the induction factors of the single elements is reproduced in blue. The ratios of both values are shown by the yellow line. If the dots of the yellow line are above the value 1, then the single elements show a synergistic interaction.

Figure 14:
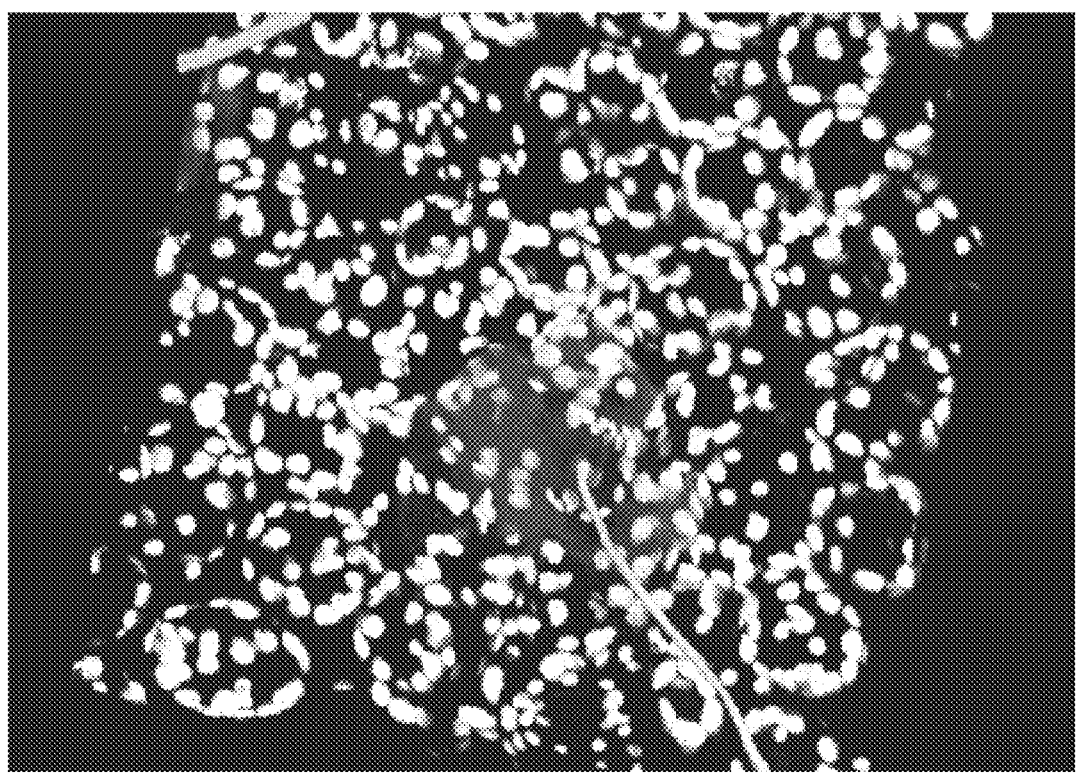

FIG. 14: Transgenic sugar beets with a 4×Cis05-RFP construct were infected with *Cercospora beticola*. The infection leads to activation of the chimeric 4×Cis05 promoter, which leads to the formation of the red fluorescing RFP protein. The protein is seen as red fluorescent under the microscope. As can be seen, the induction and thus the fluorescence are limited to the region around the penetration site or the infection location.

Figure 15:
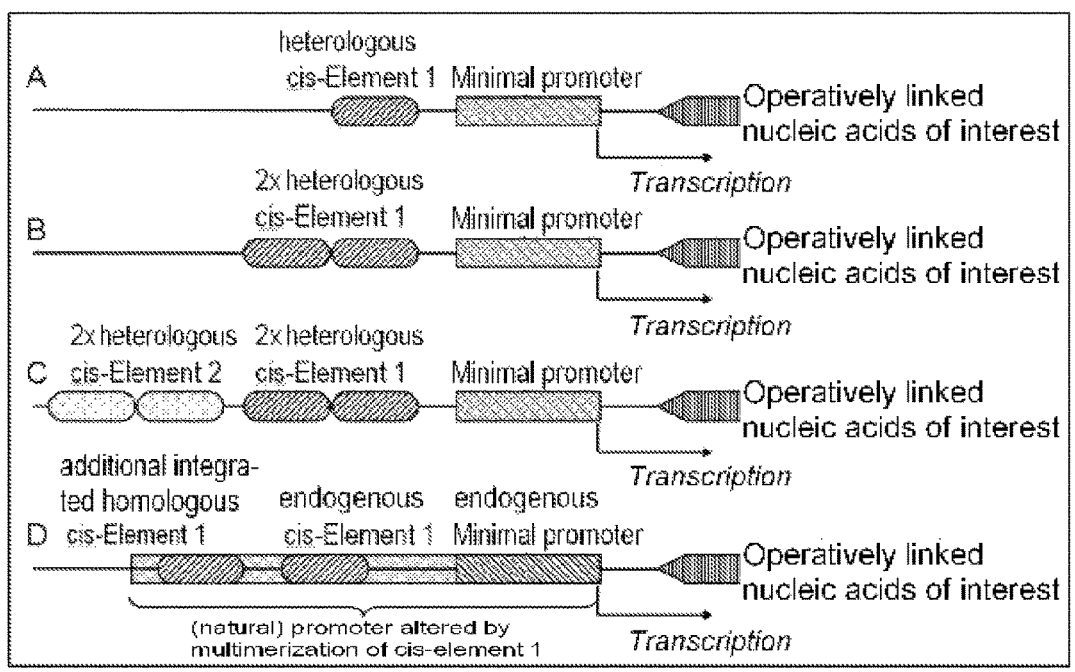

FIG. 15: Exemplary schematic representations of a chimeric promoter in the sense of the invention. The chimeric promoter is operatively linked with a nucleic acid molecule of interest and includes (A) a heterologous cis-regulatory element next to a minimal promoter, (B) a dimer/multimer of a heterologous cis-regulatory element next to a minimal promoter or (C) two dimers/multimers, each having different heterologous cis-regulatory elements, next to a minimal promoter. Furthermore, (D) shows as an exemplary chimeric promoter a natural promoter including an endogenous minimal promoter and an endogenous cis-regulatory element, wherein said promoter was modified through integration of an additional homologous cis-regulatory element.

Figure 16:
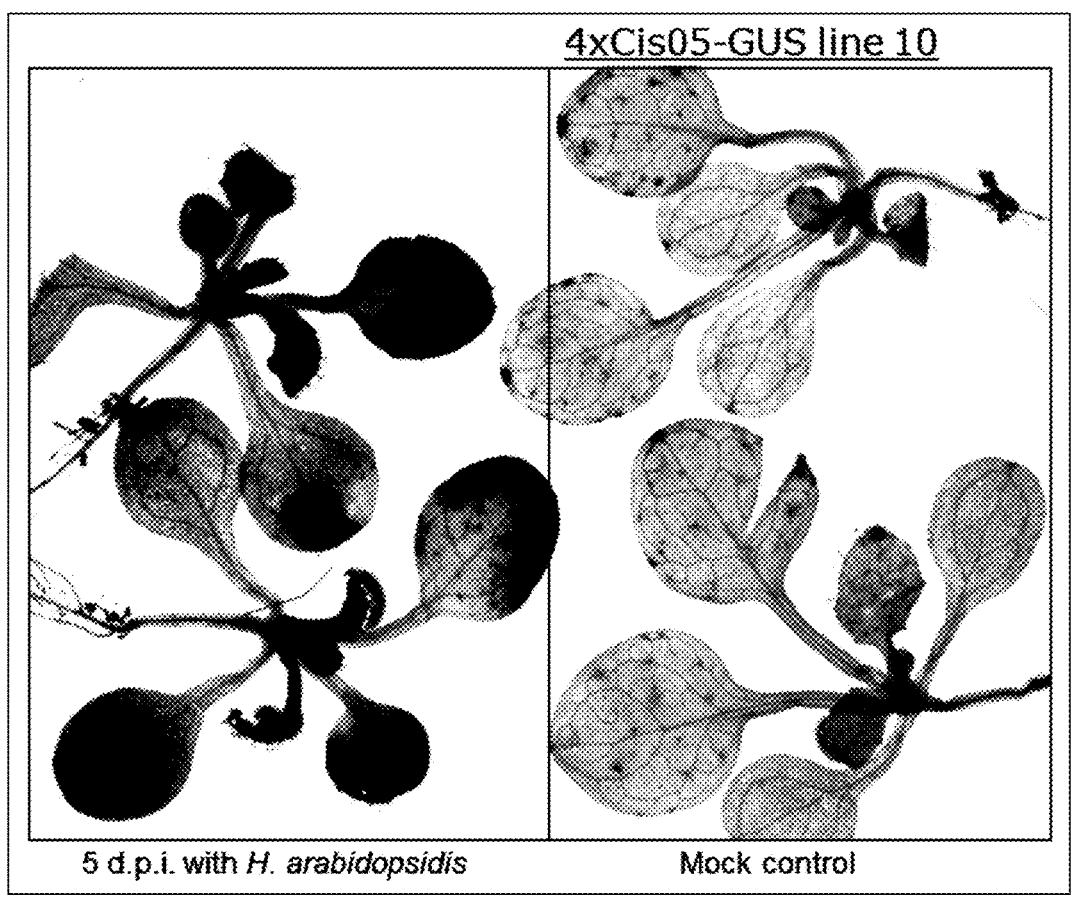

FIG. 16: Transgenic *Arabidopsis* plants with a tetramer of the cis-regulatory element Cis05 in a chimeric promoter that controls the expression of the GUS reporter gene to investigate the pathogen-induced, wound-induced, and tissue-specific activity of the element. Ten independent transformants were investigated for the promoter. One respectively representative line is shown. The image on the left-hand side (5 d.p.i. with *H. arabidopsidis*) shows the activity of the promoter subsequent to infection with the compatible pathogen *Hyaloperonospora arabidopsidis*, while the image on the right-hand side (Mock control) is the corresponding control. The promoter shows a clear induction through *Hyaloperonospora arabidopsidis* (dark coloration of the plant tissue).

On the right-hand image, a leaf is additionally cut into. A blue coloration at this cut surface would indicate a wound inducibility of the promoter with the tetramer of the cis-regulatory element Cis05.

Bioinformatic Identification of the Inventive Cis-Regulatory Elements:

Publicly available microarray-expression data are the basis for the bioinformatic identification of the novel cis-regulatory elements. Said expression data are deposited in databases such as TAIR, NASCArrays, Geo or ArrayExpress or can be obtained directly from corresponding publications of microarray experiments (e.g. Rhee et al., 2003; Craigon et al., 2004; Barret and Edgar, 2006; Brazma et al., 2006, Zipfel et al., 2004, 2006; Bülow et al., 2007; Wan et al., 2008). For the bioinformatic identification of novel cis-regulatory elements, initially the publicly available microarray-expression data were used to define groups of genes of the *Arabidopsis thaliana* plant, the expression of which is induced by pathogens such as *P. syringae* or *B. cinerea* or PAMPs like flg22 or chitin. Then the sequences of the promoters of these gene groups were extracted from the genome sequence of *Arabidopsis thaliana* (TAIR; http://www.arabidopsis.org). Using different known algorithms (MEME, Bioprospector, Alignace, BEST and the like the promoter sequences were examined for concentrated motifs.

Database Queries

A software tool was written for the database queries for identifying co-regulated genes, which tool permits identification of genes that are upregulated or induced together by up to six different stimuli. More than 700 database queries for identifying co-regulated genes were performed. This query process delivered more than 400 groups of genes induced together that are suitable for an identification of shared cis-regulatory motifs with the BEST software package (Che et al., 2005). By raising the necessary induction factor, the number of shared regulated genes in 77 groups was reduced to 120 genes. The total number of gene groups of co-regulated genes (2-120) was 510 thereafter.

Of these 510 gene groups, 500-bp or 1000-bp long promoter sequences upstream from the transcription start [SITE—what "TSS" stands for)] (TSS) of the co-regulated genes were extracted of which the TSS was known. The promoter sequences of the co-regulated gene groups were examined in accordance with conserved sequence motifs by the BEST, Cismodule, MD-Scan, BioProspector or MEME programs. Motif lengths of 5-10 nt, 10-15 nt and 15-20 nt were selected. Approximately 500×3 (motif lengths)=1500 queries were performed. In most cases, by lengthening the motif lengths, no further motifs were identified that did not already occur in the shorter motif lengths. In the BEST analyses, a motif was always classified when it was found by at least two of the four total BEST programs.

Given certain different stimuli, the same co-regulated genes, and therefore also the same motifs, were obtained. A summary of the identical motifs of redundant gene groups (GG) to novel motifs (gene groups table) followed, so that only unique motifs were compared in the comparative, systematizing analysis of all motifs among themselves.

A catalog was created that contains all identified motifs plus evaluation dataset and the sequence logos of the individual motifs. The sequence logos (Crooks et al., 2004), created under http://weblogo.berkeley.edu/, reflect the conservation of the nucleotide at the individual positions of the motif. The matrix was created from the sequences forming the motif, the sequences and the related genes thereof likewise being reflected.

The STAMP program (Mahony and Benos, 2007) that can be invoked from the Internet address http://www.benoslab.pitt.edu/stamp was used to compare the identified motifs to already known cis-regulatory elements (PLACE, Agris, Athamap). With the STAMP web server, similar motifs can furthermore be grouped into a motif group. The program issues a phylogenetic tree in which the similarities of the motif groups are shown as an overview (FIG. 4).

Proof of Pathogen Inducibility of the Identified Cis-Regulatory Elements

Since bioinformatic approaches are prone to identifying false-positive sequences, the pathogen inducibility must be experimentally confirmed. For said experimental confirmation, the bioinformatically-identified sequences were cloned as a tetramer in front of a luciferase reporter gene using standard DNA cloning procedures and tested for their inducibility in a transient expression system in parsley by the PAMP PEP25.

Elements were selected for the experimental test that are novel and show no similarity to known cis-regulatory elements of the pathogen-conveyed induction. The single sequences given in Table 2 were synthesized in vitro and cloned into the plasmid MS23 with SpeI and XbaI or with SpeI and SalI linkers. MS23 carries either a ß-glucuronidase (GUS)-reporter gene or a luciferase reporter gene with a 35S minimal promoter. All elements were tetramerized and sequenced for testing. The plasmids including 2×Cis05 element and the multimerized 4×Cis05 element are shown in FIG. 1 as an example of cloning the single sequences as chimeric promoters.

TABLE 2

Examined Single Sequences. The table lists the novel identifiers and sequences of the examined potentially cis-regulatory elements. The bioinformatically identified core sequences are emphasized (boldface type and underlined). The result of the PEP25/parsley test is reproduced in the last column (−: no induction; +: inducible).

| Single-sequence identifier | Motif group | AGI | Single sequence | Inducibility | SEQ ID NO: |
|---|---|---|---|---|---|
| 12i_M1_S1 | 1 | At5g04340 | TCTCATCTCTCGACACGCAACTTCC | + | 26 |
| Cis09 | 1 | At1g27730 | TGCACACACACACACGTGTACTAGGTCAAACCAAACGT | + | 24 |
| Cis12 | 1 | At2g33580 | CAAAAAGTCAACACATACGACGCGTTTCCATTGACTAAATA | + | 25 |
| 12c_M1_S1 | 4 | At1g21100 | TCTACTAGAGGCCCATTAGGACCGGCAT | − | 45 |
| 20u_M1_S1 | 5 | At1g13990 | TGTTGAGTCGTTTACGTCACGTCGAGAATTTCTC | + | 30 |
| 20u_M1_S2 | 5 | At4g05020 | TGTCATTATTAATACGTGACGAAACTGTAGCTCTG | + | 31 |
| 28M-1_M1_S1 | 5 | At1g09080 | TTACGTGTCAAGAAGTGATTGGAGAGGACACTCTAC | + | 32 |
| 28M-1_M1_S2 | 5 | At4g17500 | AAGACAAGTTGAGAGAGACGAGACCAATCACAACA | − | 46 |
| 28M-8_M1_S1 | 6 | At3g21520 | ATCCAACATCTCGGACCGGATCAATGATTTATCAT | − | 47 |
| 24F_M1_S1 | 7 | At2g40750 | TCATCAATGTGACATAAGCAAAGCT | − | 48 |
| 3C_M_S1 | 11 | At3g51440 | TTTGATACGGTTACGGTTAATTAACG | − | 49 |
| GG6_M1_S1 | 11 | At2g40140 | GACTTTTGACCTAAACCATTTCCAT | + | 19 |
| GG11_M1_S1 | 11 | At2g40140 | GTTTTGACTTTGACCTAAACCATTTCCATGTAGAA | + | 16 |
| GG6_M1_S2 | 11 | At5g59820 | AAGATTCTCATCCAACCGAAACGACTCTTTCGTTTT | − | 50 |
| GG11_M1_S2 | 11 | At5g59820 | AGATTCTCATCCAACCGAAACGACTCTTTCGTTTTT | − | 51 |
| GG11_M1_S3 | 11 | At1g27730 | TCTTCTTCATTTTACCAACACCACTTGCACACACAC | − | 52 |
| 22DDD_M1_S1 | 11 | At3g14990 | CCGTCTTAGTTTACCGAAACCAAAGTGGCTTTTTCT | + | 17 |
| 21G-2_M1_S1 | 11 | At1g01560 | AGTTGAATTAGTTCGGTTCGGTTCGGTTGATATTG | − | 53 |

TABLE 2-continued

Examined Single Sequences. The table lists the novel identifiers and sequences of the examined potentially cis-regulatory elements. The bioinformatically identified core sequences are emphasized (bold-face type and underlined). The result of the PEP25/parsley test is reproduced in the last column (−: no induction; +: inducible).

| Single-sequence identifier | Motif group | AGI | Single sequence | Inducibility | SEQ ID NO: |
|---|---|---|---|---|---|
| 21G-2_M1_S2 | 11 | At3g55470 | CGTAATAATG<u>GTTTGGTTTGGTTTG</u>ATCAAGTCTT | + | 18 |
| 37E_M1_S1 | 12 | At2g39200 | CGATA<u>AACTTGCGAAACCC</u>TAAAA | − | 54 |
| 18H_M2_S1 | 12 | At1g70170 | CAACACAA<u>AACGCAAAC</u>GCAGACCTC | + | 20 |
| 18H_M2_S2 | 12 | At2g35980 | TATTGGA<u>GTTTGGGGC</u>AACATCAC | − | 55 |
| 16MM_M1_S1 | 12 | At5g05340 | TTCAACCCTATAA<u>ACCAAAACA</u>AATAACAGAATGC | − | 56 |
| 38M_M1_S1 | 12 | At4g23810 | AAATAATTATTTA<u>TGGTTTGGT</u>CATTTGGTCAAAT | + | 22 |
| 31_M3_S1 | 12 | At1g26390 | CGCCTCAAT<u>CATGAAAACGAATCCTCT</u>GTAGTAGTG | − | 57 |
| 18H_M2_S3 | 12 | At1g70170 | AATTGACAAAGA<u>CACGCAAAC</u>GATTCCAACGACC | + | 21 |
| 26LLL_M1_S1 | 12 | At1g67920 | TTACCGACACGTAA<u>CCAAAACT</u>CACCGAACACCGT | − | 58 |
| 38M_M1_S2 | 12 | At2g29460 | GTTTCGAACGGGA<u>ACCAAACCA</u>TAATATGCGATGC | − | 59 |
| 38M_M1_S3 | 12 | At3g54960 | ACACTATTGGTCT<u>TGGTTTGGT</u>TTATATGCACGAC | − | 60 |
| 23LLL_M1_S1 | 12 | At2g30770 | GAAAACGATGGGTT<u>CCAAAACT</u>GTCGCTAATAAACT | − | 61 |
| 37D_M_S1 | 12 | At1g32940 | TCTCCACTCGTTGT<u>GATTTGGT</u>CTGCAAGAAAACTA | − | 62 |
| 23LLL_M1_S2 | 12 | At1g01480 | ACGTTTTGAAATAT<u>TGTTTTGG</u>ATGGAGATTTTTTC | − | 63 |
| 34G-4_M1_S1 | 12 | At3g28740 | ATTTTTCATTTCGCC<u>CCAAAACA</u>ATTATCCTAACGTT | − | 64 |
| 26LLL_M1_S2 | 12 | At4g01700 | AGTCAAAACGTAGA<u>CCAAAAC</u>AAAAACATGTAACT | + | 23 |
| 27H-8_M1_S1 | 12 | At4g18430 | TTTTATAACACTA<u>CCAAAACCAA</u>TAAGCCCTTTCGT | − | 65 |
| 26KKK_M1_S1 | 12 | At2g43510 | TCATCAAACCAATC<u>GGTTTGGT</u>CCTAAAGATAATT | − | 66 |
| 19Q_M1_S1 | 13 | At4g35180 | GTCAATATACAC<u>AGCCACCGAAC</u>AAATTACTCTAT | − | 67 |
| 21S_M1_S1 | 14 | At2g14610 | AAGCGATGT<u>TTACGAACCCC</u>AAAATC | − | 68 |
| 28H-9_M1_S1 | 14 | At1g19020 | AGATTT<u>GTTCGAGAACCTT</u>GAGAAA | − | 69 |
| 28H-9_M1_S2 | 14 | At4g37370 | TTGCTA<u>CTTCGAGAACATT</u>GGTCAA | − | 70 |
| 20a_M1_S1 | 15 | At5g04340 | TTAGAAGT<u>GGCTCGAGT</u>GTTCTACTT | − | 71 |
| 20a_M1_S2 | 15 | At5g20230 | AAGAAGA<u>CAATCGAGCC</u>TAGAAATT | − | 72 |
| 12G_M2_S1 | 18 | At1g61800 | CCATACAATATAAA<u>CCACCAA</u>ACCATAACCACAAA | + | 33 |
| 3D_M1_S1 | 18 | At4g39950 | AATAATGTTCAAC<u>GTTGGTGGTGG</u>TACTCAAGATGG | − | 73 |
| 41J_M1_S1 | 19 | At3g09940 | TCAAATACAGGCA<u>ACCAAGACTC</u>GAGATCCTCATCG | − | 74 |
| 37C_M1_S1 | 20 | At3g51440 | AGAAAATA<u>TTGGGCC</u>TACTGGGAA | − | 75 |
| 3M_M3_S1 | 20 | At3g02800 | AGATTCCTGAAGTGA<u>GGTCCA</u>CCCTAAAATCCATTT | − | 76 |
| GG8_M1_S1 | 21/21n | At1g27730 | CACACA<u>CGTGTACTAGGTC</u>AAACCA | + | 27 |
| 27G-8_M1_S1 | 21/21n | At2g38860 | AGGACTTTTCACC<u>AGTTGGACT</u>TTGAAGCCACCAA | + | 28 |
| 27G-8_M1_S2 | 21 | At1g72060 | GGTTT<u>AGTCAAAGT</u>AAACAAG<u>ACTTTGACT</u>GTTCA | − | 77 |
| 27B-10_M1_S1 | 21 | At1g22890 | TGAACTTAAT<u>CACTGTCATTGTTTT</u>CGTAACAATTT | − | 78 |
| 26WW_M2_S1 | 21n | At4g02380 | CTCA<u>AAGGCCAGAATTGACGCAGCC</u>GTTT | + | 42 |
| 27B-10_M1_S3 | 21n | At1g21120 | CCTTGG<u>CCCAGTCCTTGGTCGT</u>CGTATC | + | 43 |

TABLE 2-continued

Examined Single Sequences. The table lists the novel identifiers and sequences of the examined potentially cis-regulatory elements. The bioinformatically identified core sequences are emphasized (bold-face type and underlined). The result of the PEP25/parsley test is reproduced in the last column (-: no induction; +: inducible).

| Single-sequence identifier | Motif group | AGI | Single sequence | Induci-bility | SEQ ID NO: |
|---|---|---|---|---|---|
| GG4_M2_S1 | 22 | At3g14990 | GAAAAATGTGTGTGTTTGTGTTAATT | - | 79 |
| GG4_M2_S2 | 22 | At5g59820 | ATAGTTCCCAAACGGACACGAACACA | - | 80 |
| 30A-8_M1_S1 | 24 | At3g49620 | GCAAACTAACGCCGGCGGCCGTCTTG | - | 81 |
| 301-8_M1_S1 | 27 | At5g12930 | ACAACAGACGACTTTTCATAATTCA | + | 7 |
| 301-8_M1_S2 | 27 | At1g26390 | CTATATGACAAAAGTCAAACATAAA | + | 8 |
| GG13_M1_S2 | 27 | At3g26830 | TGTTCACTTTGAAAAGTATTCTTTGAG | + | 9 |
| 30H-8_M1_S1 | 27 | At1g35230 | TAGCTGTTGAAATTTCCAAGAAAAT | - | 82 |
| 14S_M1_S1 | 27 | At1g76960 | CGATCAGACTTTTCTACGCAAGAGAA | + | 10 |
| 21S_M3_S1 | 27 | At1g76960 | TAATTTCTCTTGCGTAGAAAAGTCTGATCGGGAAG | + | 11 |
| 301-8_M1_S3 | 27 | At5g24110 | TCGTTCTTCAGTCAAAAAGTCAAACTATCTCTC | + | 12 |
| Cis02 | 27 | At5g64905 | GAGCGTGAATTGACTTTGACCAAAACCAAA | + | 13 |
| Cis05 | 27 | At5g24110 | GGTCAGCATGTTGGACTTTCCAAATTCATTGACCAAAG | + | 14 |
| Cis13 | 27 | At1g26380 | AAAATAAACAGCTACTTGACGAAAAGTCAAACCAAATTC | + | 15 |
| 22AAA_M1_S1 | 31 | At2g40000 | TTTTTCTCGTCCCCATCCTCTATCC | - | 83 |
| 12r_M1_S1 | 32 | At1g73480 | CAATCTACTCGTCTCTTCTCTTACAT | + | 34 |
| GG3_M1_S1 | 32 | At5g44420 | TAGGTTCCTGCCCTCTCCGTTCCTCC | - | 84 |
| GG3_M1_S2 | 32 | At4g39980 | TCGAAACCAACCCTCTCCCTTATAAA | - | 85 |
| 20EE_M1_S1 | 32 | At4g39980 | GAAACCAACCCTCTCCCTTATAAATA | - | 86 |
| 24P_M1_S1 | 32 | At1g30135 | TGTTTTGTTTCCACCGTCTCTCCCGTGTCCTCTCTC | - | 87 |

The tetramerized single sequences in transiently transformed parsley cells from a cell culture were tested in the following for their inducibility by the PAMP PEP25. In addition to a general validation, it should be ensured that the elements in different plant species can be induced and by different elicitors. For the test in parsley, protoplasts were isolated from a five-day-old parsley cell culture. 35 ml cell culture were removed by centrifugation and resuspended in 90 ml of a sterile-filtered solution with 0.5% cellulase, 0.2% macerozyme R-10, and 0.24 M $CaCl_2$ and incubated with stirring overnight at 26° C. Thereafter, the released protoplasts were pelletized though centrifugation, washed with 40 ml 0.24 M $CaCl_2$ and subsequently resuspended in 50 ml P5 medium (1 bag prepared media Gamborgs B-5, 1 mg 2.4 D, 96.9 g saccharose, pH 5.7 with 1M KOH, sterile filtered). After centrifugation, the protoplasts float on the surface of the P5 medium and can be removed. The purification with P5 medium was repeated 2×.

For the transformation, 5 µg of the promoter construct to be tested, 2.5 µg of a constitutive renilla luciferase-expressing normalizing vector, and 200 µl PEG in 10 ml were put in screw-cap test tubes. 200 µl protoplasts were added, after which the mixture was carefully stirred and incubated for 20 min in the dark at room temperature. The reaction was subsequently stopped by the addition of 5 ml 0.275M $CaNO_3$-Lsg. The transformed protoplasts were removed by centrifugation, held in 6 ml P5 medium and divided into 2 aliquots. One aliquot was elicited with Pep25 (final concentration: 300 ng/ml; sequence: VTAGAEVWNQPVRGFK-VYEQTEMT) (SEQ ID NO: 88)) and the other served as control. After overnight incubation, the protoplasts were retrieved through centrifugation. The luciferase activity was determined with the Dual Luciferase Kit (Promega, Mannheim, Germany) in a Sirius Luminometer (Berthold Detection System GmbH, Pforzheim, Germany). The parsley cells were pelletized through cent trifugation and lysed for 20 minutes at 4° C. in150 µl PLB buffer (Passive Lysis Buffer; Promega, Mannheim, Germany). The cell residues were removed by centrifugation for 20 minutes at 13,000 rpm and 4° C. in a bench centrifuge.

Various procedures were applied with the lysate depending on whether the luciferase reporter gene or the GUS reporter gene were used. If the luciferase reporter gene was used, a 5 µl sample of the supernatant with the released luciferase is mixed with 50 µl LARII buffer (Promega, Mannheim, Germany) in 5 ml test tubes (Sarstedt, item no. 55.476). The buffer contains the substrate of the luciferase so that the activity of the enzyme and thus of the promoter can be measured with the Luminometer. The measurement occurs with 2 seconds pre-measurement time and 10 seconds luciferase-measurement time. Thereafter, 50 µl Stop & Glo buffer (Promega, Mannheim, Germany) is added and carefully mixed by drawing up. This buffer stops the luciferase activity and renders measurable the constitutive *renilla-luciferase* activity of the normalizing vector. This measured value is used for normalizing the different transformation efficiencies. The measurement occurs with 2 seconds pre-measurement time and 10 seconds luciferase-measurement time.

If the ß-glucuronidase (GUS) reporter gene from *E. coli* was used (Jefferson et al., 1987), the proof is effected by an enzyme reaction in which the Substrate MUG is hydrolized into 4-MU. Then 4-MU is proven and quantified by its fluorescence. Using these methods, the activity with and without the PAMP PEP25 was measured for all single sequences examined.

Table 2 lists all tested single sequences. It additionally lists whether they were inducible by the PAMP PEP25 in parsley. The cis-regulatory elements (single sequences) identified as pathogen-inducible and the motifs thereof are summarized in FIG. 2.

Mutation Analyses of the Identified Core Sequences

Mutation analyses were conducted for selected single sequences to prove that the respective identified core sequence is responsible for the PAMP- and pathogen-inducibility of the single sequences. Mutated derivatives of the single sequences were created therefor. The mutated single sequences were synthesized as oligonucleotides. The cloning of the plasmids was conducted corresponding to the constructs with chimeric promoters without mutations. Thereafter, the constructs were tested, as previously described above, for their PEP25 inducibility in parsley. The results of the mutation analyses are reproduced in FIG. 5A, FIG. 5B, FIG. 6A, and FIG. 6B. It could be shown for all five elements examined that the identified core sequence is responsible for the inducibility.

This is especially significant for single sequences Cis05 and 30l-8 M1 S2 of the group 27. The core sequence of 30l-8_M1_S2 partially overlaps with a sequence (GTCAA) complementary to the W-box (TTGAC; Rushton et al., 1996). An overlapping W-box sequence was also found in the single sequences 30l-8_M1_S3, Cis02, and Cis13.

However, it could be shown through the mutation analyses, in particular through the variants 30l-8_M1_S2_mut2, that bases outside the W-box are vital for the PAMP inducibility (FIG. 6A). Other members of the group 27 show no overlapping W-box sequence. Correspondingly, the mandatory core sequence TGAC for the W-box is not part of the sequence- or family motif of the group 27 (FIG. 3F). Thus the motifs or the single sequences of the group 27 do not involve variants of the W-box.

A W-box sequence is found outside the core sequence in the single sequence Cis05. The mutation analyses could show here that this W-box does indeed convey PAMP inducibility. However, the mutation leads only the Cis05 core sequence or only the W-box to a reduction in the inducibility and only mutation of both elements leads to a complete loss of the inducibility. Thus a single sequence with two functional, PAMP- and pathogen-inducible cis-regulatory elements, the known W-box, and the novel Cis05-Motiv (FIG. 2T) are concerned. The combination of both elements shows a considerably higher activity than the single elements alone.

To isolate the sequence region of the element Cis05 motif (FIG. 2T) that conveys the inducibility, said element was tetramerized separately from the W-box (sCis05) and four additional mutated derivatives of the Cis05 motif were created. The derivatives were tested for their inducibility through the PAMP PEP25 in parsley as described above (FIG. 5B). It could be shown that in addition to the critical importance of the core sequence for the inducibility, both bases in 5'-direction prior to the core sequence are also essential for the inducibility of Cis05, which further confirms that it is not a W-box variant.

The core sequences of the elements 20u_M1_S1 and 27G-8_M1_S1 could also be confirmed through additional mutation analyses. The tests were conducted as already described above. The results of these mutation analyses are reproduced in FIG. 6B (on top: 20u_M1_S1; on the bottom: 27G-8_M1_S1).

Derivation of Family Motifs

Because the cis-regulatory elements identified in *Arabidopsis* promoters were tested in parsley, a biological functionality, which spans all plant species, of the identified cis-regulatory elements was ensured. The experiments showed, as expected, that not all of the bioinformatically identified sequences are functional. Roughly one third of the tested DNA sequences were inducible by PEP25 in parsley. The other sequences were false-positive sequences from the bioinformatic analysis or did not exhibit the desired species-spanning biological functionality. These important results could be used to identify the family motifs of the motif groups 1, 5, 11, 12, 21, 21n and 27 as well as the corresponding strongly conserved, characteristic core sequences (FIG. 3) on the basis of the functionally effective single sequences. To this end, all functionally effective single sequences belonging to a motif group were summarized and a consensus and a motif were derived therefrom. First the region was that is part of the core sequence in all underlying single sequences was defined as a characteristic core sequence motif of the family motif.

The core sequence of motif group 27 is also in the sequence LS10 (Lebel et al., 1998). In said latter sequence, a mutation including ten bases was generated in the native PR-1 promoter in that sequence region, which mutation led to a sharp decline of a SA- or INA-inducibility of the native promoter. The results shown there, however, do not enable the derivation of a motif or of a core sequence. Furthermore, the usability of LS10 for chimeric promotes is not shown. Moreover, the family motif of the motif group 27 differentiates the motif group from the LS10 sequence. The family motif excludes a C on the position 5, while in LS10 a Cis present at said position. Furthermore, it excludes a G from position 17, while in LS10 a G is present as said position. Finally it necessitates a T or C at position 18, while an A is present in LS10 at this position.

Proof of the Inducibility by the Pathogenic Fungus *Cercospora beticola* in Stably Transformed Sugar Beets The novel cis-regulatory elements should distinguish themselves in that they can be induced in different plant species by different PAMPs and pathogens. To demonstrate the inducibility in an agronomically important plant by an agronomically important pathogen, the single sequences that tested positive in parsley were stably transformed in sugar beets. To this end, the chimeric promoters were recloned with the tetramerized single sequences including the luc gene at the ascl- and sacl-interfaces in the binary vector 1×W1-luc-kan, a plasmid based on the binary vector pGPTV. In FIG. 7, the vector 4×Cis05-luc-kan is shown as an example. Corresponding vectors were created for all tested elements. The plasmid DNA of the binary vectors was isolated from *E. Coli* and transformed into the *Agrobacterium tumefaciens* strain GV3101 by a Gene Pulser® II. Electroporation System at a setting of 25 mF and 2.5 kV. The selection of recombinant *A. tumefaciens*-{2} clones occurred by using the antibiotic kanamycin (50 mg/l). The transformation of the sugar beets was effected according to Lindsey et al. (1991) with the use of the antibiotic kanamycin.

The transgenesis of the plants was tested by PCR. The use of the primers GTGGAGAGGCTATTCGGTA (SEQ ID NO: 36) and CCACCATGATATTCGGCAAG (SEQ ID NO: 37) led to the amplification of a 553-bp-sized DNA fragment from the nptII-gene. The PCR was conducted using 10 ng genomic DNA, a primer concentration of 0.2 µM at an annealing temperature of 55° C. in a multicycler PTC-200 (MJ Research, Watertown, USA).

Ten to twenty independent transgenic lines were clonally increased in in vitro culture and infected with *Cercospora beticola* (Ahlburg isolate). After one, two, three, and four days, four plants/line were harvested and their luciferase activity was measured with the Promega Luciferase Assay System, 100 assays, cat.no. E1500 (LAR). The samples were housed in four volumes CCLR buffer (Cell Culture Lysis Reagent, 5×) and processed using a Heidolph (RZR 2020). The plant residue was removed by centrifugation for ten min at 4° C. and 14000 rpm and the supernatant was used for the luciferase measurement. A 10-µl sample was pipetted into a 5 ml test tube (Sarstedt, item no. 55.476) for measurement and 100 µl Luciferase Assay Reagent (LAR; Promega, Mannheim, Germany) was added. After careful mixing, the luciferase activity was determined in a Sirius Luminometer (Berthold Detection System GmbH, Pforzheim, Germany).

Novel elements from groups 12 and 27 (see FIGS. 3 D and F for group classification) were tested, among other things. The median was calculated of the measured luciferase activities of the approximately 10 to 20 independent transgenic lines with a chimeric promoter. The tests of the different promoters are summarized according to groups from which the elements originated. The results are shown in FIG. 8 A. The direct comparison shows that the single sequences of a motif group have significantly differing activities despite the high homology of the motifs they contain. The nucleotides of the family motifs that border the core sequence can thus heavily influence the promoter strength and the background α-tivity. The different sequences of a motif group are thus not identical in their function, but rather permit the development of chimeric promoters with quantitative differences in the regulation of the gene expression.

To test a further motif group, the element GG6_M1 (single sequence GG6_M1_S1) was stably transformed in sugar beet as specified above and tested for inducibility by *Cercospora*. Ten to twenty independent transgenic lines were clonally increased in vitro culture and infected with *Cercospora beticola* (Ahlburg isolate). After two, three, four, and seven days, four plants/line were harvested and their luciferase activity was measured with the Promega Luciferase Assay System, 100 assays, cat. no. E1500 (LAR). The results are shown in FIG. 9 and demonstrate a clear inducibility of the single sequence GG6_M1_S1 in sugar beet by *Cercospora beticola*. Furthermore, a histochemical analysis showed that the induction largely occurred in vascular tissue.

To investigate the influence of the W-box sequence in the single sequence Cis05 in stably transformed plants, the mutated derivatives Cis05mut1 and Cis05mut2 and the shortened single sequence sCis05 from the parsley tests were stably transformed in sugar beet. Construct creation and transformation were conducted as described above. Eighteen independent transgenic lines were clonally propagated in vitro and infected with *Cercospora beticola* (Ahlburg isolate). After one, two, three, and four days, four plants/line were harvested and their luciferase activity was measured as described above (FIG. 8 B).

The mutation analysis in stably transformed plants shows that this W-box alone, i.e. with mutated Cis05 motif, conveys only a weak pathogen inducibility by *Cercospora*. The Cis05 motif alone (mutated W-box or shortened element without W-box) is, on the other hand, significantly inducible. The complete Cis05 single sequence with W-box is likewise inducible, but demonstrates an increased background activity relative to the derivatives without W-box. Thus the Cis05 motif alone in stably transformed sugar beet is equivalent or even superior to the combination with the W-box.

Another important feature of the inventive chimeric promoters is that the pathogen-induced activity is limited to the region of the infection site. This is shown in FIG. 14 using the example of the inventive promoter 4×Cis05. Said promoter was merged with the red fluorescing reporter gene and the construct thereby obtained stably transformed in sugar beet. The activity can be observed as red fluorescence under the laser scanning microscope. In FIG. 14 shows the local induction of the 4×Cis05 promoter around the penetration site of a *Cercospora hyphae*.

Enlarged Species-Wide Pathogen Inducibility

As a further example for broad applicability of the cis-regulatory elements in different plant species, the inducibility was demonstrated for Cis05 in transient experiments in the monocotyledonous plant wheat through the fungus *Fusarium culmorum*. Since the 35S minimal promoter in wheat conveys insufficient activity, the Cis05 elements had to be recloned. To that end, they were excised from the plasmids used for the parsley tests with the enzymes Eco31I and XbaI and cloned in the vector pubiTATARucII opened with Eco31I and BcuI (FIG. 10). Corresponding constructs were generated for Cis05 as well as for the mutated Cis05 single sequences Cis05mut1 and Cis05mut2 in which either the Cis05 motif or the W-box is mutated. These constructs were biolistically transformed in the primary leaves of the wheat variety "taifun", which leaves were infected with *Fusarium graminearum*, as well as in non-infected control leaves.

For the infection, *Fusarium graminearum* mycel with a specimen slide covered in fungal plate was scraped off, briefly ground in 200 ml water with an Ultraturrax, and suspended. Thereafter, 200 µl 2% triton was added and the wheat primary leaves were stirred in the suspension for one minute. Subsequent thereto, the infected leaf pieces and non-infected control leaf pieces were placed on $H_2O$ agar plates and transiently transformed with a Bio-Rad particle gun according to manufacturer's instruction using 1100 psi rupture disks. A constitutive luciferase-expressing vector was used as a normalizing vector.

The wheat leaves were then incubated over night at 25° C. To determine the luciferase activities, each of the leaves was ground up in a mortar in 1 ml PLB buffer with sea sand. After 20 minutes of centrifugation at 4° C., the a 5 µl sample of the supernatant with the released luciferase is mixed in 5 ml test tubes (Sarstedt, item no. 55.476) with 50 µl LARII buffer (Promega, Mannheim, Germany). The buffer contains the substrate of the luciferase so that the activity of the normalizing vectors can be measured. This measured value is used for normalizing the different transformation efficiencies. The measurement is effected with two seconds pre-measurement time and ten seconds luciferase measurement time. Subsequent thereto, 50 µl Stop & Glo buffer (Promega, Mannheim, Germany) is added and carefully mixed by drawing up. This buffer stops the luciferase activity and renders measurable the *renilla-luciferase* activity that corresponds to the activity of the Cis05 promoters. The measurement likewise occurs with two seconds pre-measurement time and ten seconds luciferase-measurement time.

The induced or non-induced activities of the 4×Cis05 promoter and of its mutated derivatives were measured in five biological repetitions (FIG. 11). Thereafter, the complete experiment was repeated once again. Both repetitions demonstrate that in wheat, the pathogen-induced activity stems from the Cis05 motif, while the W-box motif does not convey any activity induced by *Fusarium graminearum*.

Analysis of the pathogen- or wound-induced and tissue-specific activity of the elements Cis02, Cis05, Cis09, Cis12 or Cis13 in *Arabidopsis*.

The novel cis-regulatory elements should thereby distinguish themselves in that they can be induced in different plant species by different PAMPs and pathogens. Six promoters with tetramerized single sequences were stably transformed in *Arabidopsis* as an additional control for the activity of the chimeric promoters. The tetramerized elements Cis02, Cis05, Cis09, Cis12 or Cis13 were additionally cloned with 35S minimal promoter prior to the GUS reporter gene in the transformation vector pBIN-GUS. The final construct was transformed in agrobacteria. A floral-dip transformation (Clough and Bent, 1998) of *Arabidopsis* plants was conducted in the following to stably integrate the promoter-GUS constructs in the plant genome. The selection of transgenic plants was made using the kanamycin antibiotic.

Ten independent transformants were investigated for each element.

The activity of the GUS reporter gene and of the promoters can be made visible with the use of a GUS dye (Jefferson et al., 1987). The activation of the respective chimeric promoters leads to the expression of an enzyme (GUS) that creates a blue dye. The coloration thus shows the activity of the respective chimeric promoters.

To test the pathogen inducibility of the promoters, the transgenic *Arabidopsis* plants were infected with the compatible pathogen *Hyaloperonospora arabidopsidis*. Five days after infection, the activity of the promoters was proven by a GUS dye. Individual leaves were additionally wounded by cutting with scissors to test the wound inducibility of the promoters (FIG. 16).

The element Cis02 demonstrated favorable pathogen inducibility and only a minimal wound inducibility. The element Cis05 demonstrated a generally strong activity and is likewise strongly induced by *H. Arabidopsidis*. The element Cis09 demonstrated a favorable induction of the promoter subsequent to infection and hardly any undesired activity after wounding. Like element Cis09, the element Cis12 demonstrated in all examined lines hardly any undesired activity after wounding, while an obvious induction through the pathogen *H. arabidopsidis* was observed. The elements Cis12 and Cis09 share a common family motif. The element Cis13 is also heavily induced through infection with *H. arabidopsidis*. An obvious wound inducibility is not, however, observed. FIG. 16 shows the exemplary GUS dyeing of transgenic *A. thaliana* plants that express the GUS reporter gene under the control of a chimeric promoter with 4×Cis05.

Combinatorials of the Cis-Regulatory Elements

Chimeric combinatorial promoters that are composed of different cis-regulatory elements can demonstrate a greater specificity and/or activity than the single elements present therein through a synergistic interaction or through integration of different signaling pathways (a promoter would be conceivable that would have to perceive and integrate signals "EF-Tu" AND "flg22" in order to be activated) (Rushton et al., 2002). To identify optimal combinations of the novel cis-regulatory elements for chimeric combinatorial promoters, chimeric combinatorial promoters, including all possible 2×2 combinations of the herein-described cis-regulatory elements Cis02, Cis05, Cis12, Cis13 and 30l-8_M1_S2 and the already published elements D-box (Rushton et al., 2002), S-box (Kirsch et al., 2000) and Gst1-box (Strittmatter et al., 1996), were generated using standard DNA cloning procedures. The approach taken followed that for the tetramerization of the single sequences described, only not the two identical dimers (e.g. 2×30l-8_M1_S2 and 2×30l-8_M1_S2), but rather two different dimers (e.g. 2×Cis05 and 2×30l-8_M1_S2) are cloned together. The thus-resulting chimeric combinatorial promoters were tested in the transient expression systems in parsley for their inducibility through the PAMP PEP25. The results (absolute non-induced and induced activity of the chimeric combinatorial promoters and the induction factor) are reproduced in FIG. 12. Chimeric combinatorial promoters with especially stronger and more specific inducibility could be identified, the induction factor of and activity of which are greater than in chimeric promoters that are constructed from only repetitions of the individual cis-regulatory elements (FIG. 13). The chimeric combinatorial promoters having the greatest induction factors and the strongest activities are summarized in Table 3.

TABLE 3

Combinations of pathogen-inducible single sequences having the greatest induction factors and induced activities.

| | | Average | Standard deviation | Coefficient of variation | Induction |
|---|---|---|---|---|---|
| Combinations with the greatest induction factor | | | | | |
| 2xCis05-2xCis05 | − | 3.23 | 2.06 | 0.64 | 149.58 |
| 2xCis05-2xCis05 | + | 482.53 | 398.05 | 0.82 | |
| 2xCis05-2xS | − | 2.00 | 1.51 | 0.76 | 115.63 |
| 2xCis05-2xS | + | 231.82 | 48.39 | 0.21 | |
| 2xCis05-2x30I8b | − | 2.47 | 1.42 | 0.58 | 123.16 |
| 2xCis05-2x30I8b | + | 304.21 | 45.38 | 0.15 | |
| 2xCis13-2xCis02 | − | 2.50 | 0.50 | 0.20 | 124.53 |
| 2xCis13-2xCis02 | + | 311.48 | 37.76 | 0.12 | |
| 2xCis13-2xCis05 | − | 2.33 | 0.41 | 0.18 | 182.59 |
| 2xCis13-2xCis05 | + | 425.23 | 258.29 | 0.61 | |
| 2xCis13-2xS | − | 4.55 | 0.65 | 0.14 | 139.85 |
| 2xCis13-2xS | + | 636.85 | 364.80 | 0.57 | |
| 2xS-2xCis02 | − | 5.28 | 3.36 | 0.64 | 106.32 |
| 2xS-2xCis02 | + | 561.76 | 440.81 | 0.78 | |
| 2xS-2xS | − | 2.76 | 0.49 | 0.18 | 138.80 |
| 2xS-2xS | + | 382.69 | 92.20 | 0.24 | |
| Gst1-2xS | − | 2.41 | 0.87 | 0.36 | 258.83 |
| Gst1-2xS | + | 624.18 | 274.19 | 0.44 | |
| 2x30I8b-2xCis05 | − | 0.90 | 0.30 | 0.34 | 135.12 |
| 2x30I8b-2xCis05 | + | 121.20 | 88.90 | 0.73 | |
| Combinations with the greatest induction factor (induced) | | | | | |
| 2xD-2xCis05 | − | 84.57 | 49.56 | 0.59 | 17.88 |
| 2xD-2xCis05 | + | 1511.90 | 580.33 | 0.38 | |
| 2xD-2xS | − | 23.96 | 17.66 | 0.74 | 57.72 |
| 2xD-2xS | + | 1382.94 | 1180.84 | 0.85 | |
| 2xD-Gst1 | − | 19.25 | 20.18 | 1.05 | 62.10 |
| 2xD-Gst1 | + | 1195.21 | 486.92 | 0.41 | |
| 2xS-2xCis12 | − | 36.84 | 19.34 | 0.53 | 29.05 |
| 2xS-2xCis12 | + | 1070.08 | 1043.46 | 0.98 | |
| 2xS-2xD | − | 22.13 | 23.38 | 1.06 | 65.56 |
| 2xS-2xD | + | 1450.50 | 1085.69 | 0.75 | |

REFERENCES

Bailey, T. L., C. Elkan (1994). "Fitting a mixture model by expectation maximization to discover motifs in biopolymers." *Proc Int Conf Intell Syst Mol Biol.* 2: 28-36.

Bulow, L., M. Schindler, et al. (2007). "PathoPlant: a platform for microarray expression data to analyze co-regulated genes involved in plant defense responses." *Nucleic Acids Res* 35 (Database issue): D841-845.

Che, D., S. Jensen, et al. (2005). "BEST: binding-site estimation suite of tools." *Bioinformatics* 21(12): 2909-2911.

Clough, S. J. and Bent, A. F. (1998). "Floral dip: a simplified method for *Agrobacterium*-mediated transformation of *Arabidopsis thaliana.*" *Plant J.* 16(6):735-43.

Eulgem, T., P. J. Rushton, et al. (2000). "The WRKY superfamily of plant transcription factors." *Trends Plant Sci* 5(5): 199-206.

Gorlich, D. and I. W. Mattaj (1996). "Nucleocytoplasmic transport." *Science* 271(5255): 1513-1518.

Gurr, S. J. and P. J. Rushton (2005). "Engineering plants with increased disease resistance: how are we going to express it?" *Trends Biotechnol* 23(6): 283-290.

Hahlbrock, K., D. Scheel, et al. (1995). "Oligopeptide elicitor-mediated defense gene activation in cultured parsley cells." *Proc Natl Acad Sci USA* 92(10): 4150-4157.

Hicks, G. R., H. M. Smith, et al. (1995). "Three classes of nuclear import signals bind to plant nuclei." *Plant Physiol* 107(4): 1055-1058.

Himmelbach, A., L. Liu et al. (2010). "Promoters of the Barley Germin-Like GER4 Gene Cluster Enable Strong Transgene Expression in Response to Pathogen Attack" *The Plant Cell* 22(3): 937-952.

Howles, P., G. Lawrence, et al. (2005). "Autoactive Alleles of the Flax L6 Rust Resistance Gene Induce Non-Race-Specific Rust Resistance Associated with the Hypersensitive Response." *Molecular Plant-Microbe Interactions* 18(6): 570-582.

Humphry, M., P. Bednarek, et al. (2010). "A regulon conserved in monocot and dicot plants defines a functional module in antifungal plant immunity." *Proc Natl Acad Sci USA* 107(50): 21896-21901.

Jefferson, R. A., Kavanagh, T. A & Bevan, M. W. (1987). "GUS fusions, 8-glucuronidase as a sensitive and versatile gene fusion marker in higher plants." *EMBO J.* 6(13): 3901-3907.

Kirsch, C., M. Takamiya-Wik, et al. (2000) "A novel regulatory element involved in rapid activation of parsley ELI7 gene family members by fungal elicitor or pathogen infection." Mol Plant Pathol. 1(4): 243-51.

Kirsch, C., E. Logemann, et al. (2001) "A highly specific pathogen-responsive promoter element from the immediate-early activated CMPG1 gene in *Petroselinum crispum*." Plant J. 26(2): 217-27.

Kovalchuk, N., M. Li, et al. (2010). "Defensin promoters as potential tools for engineering disease resistance in cereal grains." *Plant Biotechnol J* 8(1): 47-64.

Lebel, E., P. Heifetz, et al. (1998). "Functional analysis of regulatory sequences controlling PR-1 gene expression in *Arabidopsis."* Plant J 16(2): 223-233.

Liu, X., D. L. Brutlag, et al. (2001). "BioProspector: discovering conserved DNA motifs in upstream regulatory regions of co-expressed genes." *Pac Symp Biocomput:* 127-138.

Morris, K., S. A. MacKerness, et al. (2000). "Salicylic acid has a role in regulating gene expression during leaf senescence." *Plant J* 23(5): 677-685.

Rushton, P. J., A. Reinstadler, et al. (2002). "Synthetic plant promoters containing defined regulatory elements provide novel insights into pathogen- and wound-induced signaling." *Plant Cell* 14(4): 749-762.

Rushton, P. J., J. T. Torres, et al. (1996). "Interaction of elicitor-induced DNA-binding proteins with elicitor response elements in the promoters of parsley PR1 genes." *EMBO J.* 15(20): 5690-5700.

Schatz, G. and B. Dobberstein (1996). "Common principles of protein translocation across membranes." *Science* 271 (5255): 1519-1526.

Schumacher, S. B., O. Van den Hauwe, et al. (2003). "Development of a dual luciferase reporter screening assay for the detection of synthetic glucocorticoids in animal tissues." *Analyst* 128(12): 1406-1412.

Strittmatter, G., G. Gheysen, et al. (1996). "Infections with various types of organisms stimulate transcription from a short promoter fragment of the potato gst1 gene." *Mol Plant Microbe Interact* 9(1): 68-73.

Venter, M. (2007). "Synthetic promoters: genetic control through cis engineering." *Trends Plant Sci* 12(3): 118-124.

Verner, K. and G. Schatz (1988). "Protein translocation across membranes." *Science* 241(4871): 1307-1313.

Wan, J., X. C. Zhang, et al. (2008). "A LysM receptor-like kinase plays a critical role in chitin signaling and fungal resistance in *Arabidopsis."* Plant Cell 20(2):471-481.

Zipfel, C., G. Kunze, et al. (2006). "Perception of the bacterial PAMP EF-Tu by the receptor EFR restricts *Agrobacterium*-mediated transformation." *Cell* 125(4): 749-760.

Zipfel, C., S. Robatzek, et al. (2004). "Bacterial disease resistance in *Arabidopsis* through flagellin perception." *Nature* 428(6984): 764-767.

WO 00/29592 (Max-Planck-Gesellschaft zur Förderung der Wissenschaften e.V.). Chimeric promoters capable of mediating gene expression in plants upon pathogen infection and uses thereof.

WO 02/50293 (Max-Planck-Gesellschaft zur Förderung der Wissenschaften e.V.). Pflanzen mit verbesserter Widerstandskraft.

WO 03/00898 (Syngenta Participations AG). Plant genes involved in defense against pathogens.

WO 07/147,395 (KWS SAAT AG). Pathogen induzierbarer synthetischer Promotor

WO 10/079,430 (U. Bonas et al.). Modular DNA-binding domains and methods of use.

WO 11/072,246 (Regents of the University of Minnesota; Iowa State University Research Foundation Inc.). TAL effector-mediated DNA modification.

The invention claimed is:

1. A chimeric promoter comprising a minimal promoter and at least one multimer of cis-regulatory element, wherein said cis-regulatory element comprises a nucleotide sequence selected from the group consisting of
   a) SEQ ID NOS: 7-11, 13, and 15,
   b) SEQ ID NO: 2,
   c) SEQ ID NO: 140,
   d) SEQ ID NO: 141,
   e) SEQ ID NO: 142,
   f) SEQ ID NO: 143,
   g) SEQ ID NO: 144,
   h) SEQ ID NO: 35,
   i) SEQ ID NOS: 27, 28, 42, and 43; and
   wherein the cis-regulatory element is upstream from the minimal promoter and the distance from the minimal promoter sequence to the upstream cis-regulatory element is between 0 and 300 base pairs; wherein the cis-regulatory element imparts a pathogen inducible or an elicitor inducible expression to a nucleic acid molecule operably linked to the chimeric promoter in a plant cell.

2. The chimeric promoter according to claim 1, wherein the multimer is a dimer or tetramer.

3. A recombinant gene that comprises the chimeric promoter of claim 1.

4. A recombinant vector which comprises the chimeric promoter of claim 1.

5. A prokaryotic or eukaryotic host cell that comprises the chimeric promoter of claim 1.

6. A plant transformed with the chimeric promoter of claim 1.

7. Seeds, cells, tissues or part of a plant comprising the chimeric promoter of claim 1.

8. A method for producing a plant, comprising the steps of
   a) introducing the chimeric promoter of claim 1 into at least one cell of the plant and
   b) regenerating the plant.

9. The chimeric promoter of claim 1, wherein said cis-regulatory element comprises a nucleotide sequence selected from the group consisting of
   a) SEQ ID NO: 3,
   b) SEQ ID NO: 4,
   c) SEQ ID NO: 5,
   d) SEQ ID NO: 6,
   and
   e) a nucleotide sequence complementary to any one of the sequences a) to d).

10. The chimeric promoter of claim 1, wherein said cis-regulatory element comprises a nucleotide sequence selected from the group consisting of
   a) SEQ ID NO: 16,
   b) SEQ ID NO: 17,
   c) SEQ ID NO: 18,
   d) SEQ ID NO: 19,
   e) SEQ ID NO: 20,
   f) SEQ ID NO: 21,
   g) SEQ ID NO: 22,
   h) SEQ ID NO: 23,
   i) SEQ ID NO: 24,
   j) SEQ ID NO: 25,
   k) SEQ ID NO: 26,
   l) SEQ ID NO: 29,
   m) SEQ ID NO: 30,
   n) SEQ ID NO: 31,
   o) SEQ ID NO: 32,
   p) SEQ ID NO: 33,
   q) SEQ ID NO: 34,
   and
   r) a nucleotide sequence complementary to any one of the sequences from a) to q).

11. A recombinant vector which comprises the recombinant gene of claim 3.

12. A prokaryotic or eukaryotic host cell that comprises the recombinant gene of claim 3.

13. A plant transformed with the recombinant gene of claim 3.

14. Seeds, cells, tissues or part of a plant comprising a recombinant gene that comprises the chimeric promoter of claim 1.

15. A method for producing a plant, comprising the steps of
   a) introducing the recombinant gene of claim 3 into at least one cell of the plant and
   b) regenerating the plant.

16. A prokaryotic or eukaryotic host cell that comprises the recombinant vector of claim 4.

17. A plant transformed with the recombinant vector of claim 4.

18. Seeds, cells, tissues or part of a plant comprising a recombinant vector which comprises the chimeric promoter of claim 1.

19. A method for producing a plant, comprising the steps of
   a) introducing the recombinant vector of claim 4 into at least one cell of the plant and
   b) regenerating the plant.

20. The chimeric promoter according to claim 1, wherein said cis-regulatory element is derived from a different species to that of the minimal promoter.

21. The chimeric promoter according to claim 1, wherein said at least one multimer of cis-regulatory element is localized within the chimeric promoter in a genetic environment that is different from a natural promoter.

22. The chimeric promoter according to claim 1, wherein said at least one cis-regulatory element comprises at least 11 nucleotides.

23. The chimeric promoter according to claim 1, wherein the distance between two cis-regulatory elements in the multimer is 0 to 10 base pairs.

24. The chimeric promoter according to claim 1, wherein after the pathogen/elicitor contact the induction of the chimeric promoter is at least 2-fold greater than its induction without the pathogen/elicitor contact.

* * * * *

SEQUENCE LISTING

<160> NUMBER OF SEQ ID NOS: 145

<210> SEQ ID NO 1
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Family motif Group 27
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (6)..(7)
<223> OTHER INFORMATION: a, c, t or g
<220> FEATURE:
<221> NAME/KEY: misc_feature
<222> LOCATION: (9)..(14)
<223> OTHER INFORMATION: Core sequence motif
<220> FEATURE:
<221> NAME/KEY: modified_base
<222> LOCATION: (15)..(15)
<223> OTHER INFORMATION: a, c, t or g

<400> SEQUENCE: 1
nnhkdnnvaa agtmndhy                                                       18

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 11
<220> FEATURE:
<221> NAME/KEY: modified_base
<222> LOCATION: (2)..(2)
<223> OTHER INFORMATION: a, c, t or g
<220> FEATURE:
<221> NAME/KEY: modified_base
<222> LOCATION: (6)..(6)
<223> OTHER INFORMATION: a, c, t or g
<220> FEATURE:
<221> NAME/KEY: misc_feature
<222> LOCATION: (7)..(12)
<223> OTHER INFORMATION: Core sequence motif
<220> FEATURE:
<221> NAME/KEY: modified_base
<222> LOCATION: (15)..(15)
<223> OTHER INFORMATION: a, c, t or g

<400> SEQUENCE: 2
ynamcnaaac cawwny                                                         16

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 12
<220> FEATURE:
<221> NAME/KEY: modified_base
<222> LOCATION: (2)..(2)
<223> OTHER INFORMATION: a, c, t or g
<220> FEATURE:
<221> NAME/KEY: misc_feature
<222> LOCATION: (5)..(10)
<223> OTHER INFORMATION: Core sequence motif

<400> SEQUENCE: 3
wnrmscaaam smw                                                            13
```

```
<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 1
<220> FEATURE:
<221> NAME/KEY: modified_base
<222> LOCATION: (1)..(2)
<223> OTHER INFORMATION: a, c, t or g
<220> FEATURE:
<221> NAME/KEY: misc_feature
<222> LOCATION: (5)..(9)
<223> OTHER INFORMATION: Core sequence motif
<220> FEATURE:
<221> NAME/KEY: modified_base
<222> LOCATION: (11)..(11)
<223> OTHER INFORMATION: a, c, t or g

<400> SEQUENCE: 4
nnmsacrcgy nwm                                                        13

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 21
<220> FEATURE:
<221> NAME/KEY: misc_feature
<222> LOCATION: (2)..(9)
<223> OTHER INFORMATION: Core sequence motif

<400> SEQUENCE: 5
asktgkactw kgwm                                                       14

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 5
<220> FEATURE:
<221> NAME/KEY: modified_base
<222> LOCATION: (2)..(2)
<223> OTHER INFORMATION: a, c, t or g
<220> FEATURE:
<221> NAME/KEY: misc_feature
<222> LOCATION: (6)..(12)
<223> OTHER INFORMATION: Core sequence motif
<220> FEATURE:
<221> NAME/KEY: modified_base
<222> LOCATION: (15)..(15)
<223> OTHER INFORMATION: a, c, t or g

<400> SEQUENCE: 6
knwymmrtsa ckwmn                                                      15

<210> SEQ ID NO 7
<211> LENGTH: 25
<212> TYPE: DNA
<213> ORGANISM: Arabidopsis thaliana
```

```
<220> FEATURE:
<221> NAME/KEY: misc_feature
<222> LOCATION: (10)..(16)
<223> OTHER INFORMATION: Core sequence

<400> SEQUENCE: 7
acaacagacg actttcata attca                                          25

<210> SEQ ID NO 8
<211> LENGTH: 25
<212> TYPE: DNA
<213> ORGANISM: Arabidopsis thaliana
<220> FEATURE:
<221> NAME/KEY: misc_feature
<222> LOCATION: (10)..(16)
<223> OTHER INFORMATION: Core sequence

<400> SEQUENCE: 8
ctatatgaca aaagtcaaac ataaa                                         25

<210> SEQ ID NO 9
<211> LENGTH: 27
<212> TYPE: DNA
<213> ORGANISM: Arabidopsis thaliana
<220> FEATURE:
<221> NAME/KEY: misc_feature
<222> LOCATION: (7)..(21)
<223> OTHER INFORMATION: Core sequence

<400> SEQUENCE: 9
tgttcacttt gaaaagtatt ctttgag                                       27

<210> SEQ ID NO 10
<211> LENGTH: 26
<212> TYPE: DNA
<213> ORGANISM: Arabidopsis thaliana
<220> FEATURE:
<221> NAME/KEY: misc_feature
<222> LOCATION: (7)..(20)
<223> OTHER INFORMATION: Core sequence

<400> SEQUENCE: 10
cgatcagact tttctacgca agagaa                                        26

<210> SEQ ID NO 11
<211> LENGTH: 35
<212> TYPE: DNA
<213> ORGANISM: Arabidopsis thaliana
<220> FEATURE:
<221> NAME/KEY: misc_feature
<222> LOCATION: (12)..(24)
<223> OTHER INFORMATION: Core sequence

<400> SEQUENCE: 11
taatttctct tgcgtagaaa agtctgatcg ggaag                              35

<210> SEQ ID NO 12
<211> LENGTH: 35
<212> TYPE: DNA
<213> ORGANISM: Arabidopsis thaliana
<220> FEATURE:
<221> NAME/KEY: misc_feature
<222> LOCATION: (15)..(21)
<223> OTHER INFORMATION: Core sequence

<400> SEQUENCE: 12
tcgttcttca gtcaaaaagt caaactatct ctctc                              35
```

```
<210> SEQ ID NO 13
<211> LENGTH: 30
<212> TYPE: DNA
<213> ORGANISM: Arabidopsis thaliana
<220> FEATURE:
<221> NAME/KEY: misc_feature
<222> LOCATION: (12)..(18)
<223> OTHER INFORMATION: Core sequence

<400> SEQUENCE: 13
gagcgtgaat tgactttgac caaaaccaaa                                      30

<210> SEQ ID NO 14
<211> LENGTH: 38
<212> TYPE: DNA
<213> ORGANISM: Arabidopsis thaliana
<220> FEATURE:
<221> NAME/KEY: misc_feature
<222> LOCATION: (14)..(20)
<223> OTHER INFORMATION: Core sequence

<400> SEQUENCE: 14
ggtcagcatg ttggactttc caaattcatt gaccaaag                             38

<210> SEQ ID NO 15
<211> LENGTH: 39
<212> TYPE: DNA
<213> ORGANISM: Arabidopsis thaliana
<220> FEATURE:
<221> NAME/KEY: misc_feature
<222> LOCATION: (20)..(29)
<223> OTHER INFORMATION: Core sequence

<400> SEQUENCE: 15
aaaataaaca gctacttgac gaaaagtcaa accaaattc                            39

<210> SEQ ID NO 16
<211> LENGTH: 36
<212> TYPE: DNA
<213> ORGANISM: Arabidopsis thaliana
<220> FEATURE:
<221> NAME/KEY: misc_feature
<222> LOCATION: (14)..(23)
<223> OTHER INFORMATION: Core sequence

<400> SEQUENCE: 16
gttttgactt ttgacctaaa ccatttccat gtagaa                               36

<210> SEQ ID NO 17
<211> LENGTH: 36
<212> TYPE: DNA
<213> ORGANISM: Arabidopsis thaliana
<220> FEATURE:
<221> NAME/KEY: misc_feature
<222> LOCATION: (13)..(24)
<223> OTHER INFORMATION: Core sequence

<400> SEQUENCE: 17
ccgtcttagt ttaccgaaac caaagtggct ttttct                               36

<210> SEQ ID NO 18
<211> LENGTH: 35
<212> TYPE: DNA
<213> ORGANISM: Arabidopsis thaliana
<220> FEATURE:
<221> NAME/KEY: misc_feature
<222> LOCATION: (11)..(25)
<223> OTHER INFORMATION: Core sequence
```

```
<400> SEQUENCE: 18
cgtaataatg gtttggtttg gtttgatcaa gtctt                              35

<210> SEQ ID NO 19
<211> LENGTH: 25
<212> TYPE: DNA
<213> ORGANISM: Arabidopsis thaliana
<220> FEATURE:
<221> NAME/KEY: misc_feature
<222> LOCATION: (8)..(18)
<223> OTHER INFORMATION: Core sequence

<400> SEQUENCE: 19
gacttttgac ctaaaccatt tccat                                         25

<210> SEQ ID NO 20
<211> LENGTH: 26
<212> TYPE: DNA
<213> ORGANISM: Arabidopsis thaliana
<220> FEATURE:
<221> NAME/KEY: misc_feature
<222> LOCATION: (9)..(17)
<223> OTHER INFORMATION: Core sequence

<400> SEQUENCE: 20
caacacaaaa cgcaaacgca gacctc                                        26

<210> SEQ ID NO 21
<211> LENGTH: 35
<212> TYPE: DNA
<213> ORGANISM: Arabidopsis thaliana
<220> FEATURE:
<221> NAME/KEY: misc_feature
<222> LOCATION: (14)..(22)
<223> OTHER INFORMATION: Core sequence

<400> SEQUENCE: 21
aattgacaaa agacacgcaa acgattccaa cgacc                              35

<210> SEQ ID NO 22
<211> LENGTH: 35
<212> TYPE: DNA
<213> ORGANISM: Arabidopsis thaliana
<220> FEATURE:
<221> NAME/KEY: misc_feature
<222> LOCATION: (14)..(22)
<223> OTHER INFORMATION: Core sequence

<400> SEQUENCE: 22
aaataattat ttatggtttg gtcatttggt caaat                              35

<210> SEQ ID NO 23
<211> LENGTH: 35
<212> TYPE: DNA
<213> ORGANISM: Arabidopsis thaliana
<220> FEATURE:
<221> NAME/KEY: misc_feature
<222> LOCATION: (15)..(21)
<223> OTHER INFORMATION: Core sequence

<400> SEQUENCE: 23
agtcaaaacg tagaccaaaa caaaaacatg taact                              35

<210> SEQ ID NO 24
<211> LENGTH: 38
<212> TYPE: DNA
<213> ORGANISM: Arabidopsis thaliana
```

```
<220> FEATURE:
<221> NAME/KEY: misc_feature
<222> LOCATION: (12)..(19)
<223> OTHER INFORMATION: Core sequence

<400> SEQUENCE: 24
tgcacacaca cacacgtgta ctaggtcaaa ccaaacgt                              38

<210> SEQ ID NO 25
<211> LENGTH: 41
<212> TYPE: DNA
<213> ORGANISM: Arabidopsis thaliana
<220> FEATURE:
<221> NAME/KEY: misc_feature
<222> LOCATION: (20)..(25)
<223> OTHER INFORMATION: Core sequence

<400> SEQUENCE: 25
caaaaagtca acacatacga cgcgtttcca ttgactaaat a                          41

<210> SEQ ID NO 26
<211> LENGTH: 25
<212> TYPE: DNA
<213> ORGANISM: Arabidopsis thaliana
<220> FEATURE:
<221> NAME/KEY: misc_feature
<222> LOCATION: (9)..(17)
<223> OTHER INFORMATION: Core sequence

<400> SEQUENCE: 26
tctcatctct cgacacgcaa cttcc                                            25

<210> SEQ ID NO 27
<211> LENGTH: 25
<212> TYPE: DNA
<213> ORGANISM: Arabidopsis thaliana
<220> FEATURE:
<221> NAME/KEY: misc_feature
<222> LOCATION: (7)..(19)
<223> OTHER INFORMATION: Core sequence

<400> SEQUENCE: 27
cacacacgtg tactaggtca aacca                                            25

<210> SEQ ID NO 28
<211> LENGTH: 35
<212> TYPE: DNA
<213> ORGANISM: Arabidopsis thaliana
<220> FEATURE:
<221> NAME/KEY: misc_feature
<222> LOCATION: (14)..(22)
<223> OTHER INFORMATION: Core sequence

<400> SEQUENCE: 28 aggactttc accagttgga ctttgaagcc accaa                                 35

<210> SEQ ID NO 29
<211> LENGTH: 34
<212> TYPE: DNA
<213> ORGANISM: Arabidopsis thaliana
<220> FEATURE:
<221> NAME/KEY: misc_feature
<222> LOCATION: (11)..(19)
<223> OTHER INFORMATION: Core sequence

<400> SEQUENCE: 29
aagtctaaat ctttgacccc aaaaaagaga gcaa                                 34
```

<210> SEQ ID NO 30
<211> LENGTH: 35
<212> TYPE: DNA
<213> ORGANISM: Arabidopsis thaliana
<220> FEATURE:
<221> NAME/KEY: misc_feature
<222> LOCATION: (15)..(21)
<223> OTHER INFORMATION: Core sequence

<400> SEQUENCE: 30
tgttgagtcg tttacgtcac gtcgagaatt ttctc        35

<210> SEQ ID NO 31
<211> LENGTH: 35
<212> TYPE: DNA
<213> ORGANISM: Arabidopsis thaliana
<220> FEATURE:
<221> NAME/KEY: misc_feature
<222> LOCATION: (15)..(21)
<223> OTHER INFORMATION: Core sequence

<400> SEQUENCE: 31
tgtcattatt aatacgtgac gaaactgtag ctctg        35

<210> SEQ ID NO 32
<211> LENGTH: 36
<212> TYPE: DNA
<213> ORGANISM: Arabidopsis thaliana
<220> FEATURE:
<221> NAME/KEY: misc_feature
<222> LOCATION: (11)..(25)
<223> OTHER INFORMATION: Core sequence

<400> SEQUENCE: 32
ttacgtgtca agaagtgatt ggagaggaca ctctac        36

<210> SEQ ID NO 33
<211> LENGTH: 35
<212> TYPE: DNA
<213> ORGANISM: Arabidopsis thaliana
<220> FEATURE:
<221> NAME/KEY: misc_feature
<222> LOCATION: (15)..(21)
<223> OTHER INFORMATION: Core sequence

<400> SEQUENCE: 33
ccatacaata taaaccacca aaccataacc acaaa        35

<210> SEQ ID NO 34
<211> LENGTH: 26
<212> TYPE: DNA
<213> ORGANISM: Arabidopsis thaliana
<220> FEATURE:
<221> NAME/KEY: misc_feature
<222> LOCATION: (9)..(18)
<223> OTHER INFORMATION: Core sequence

<400> SEQUENCE: 34
caatctactc gtctcttctc ttacat        26

<210> SEQ ID NO 35
<211> LENGTH: 10
<212> TYPE: DNA
<213> ORGANISM: Arabidopsis thaliana

<400> SEQUENCE: 35
tcgtctcttc        10

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 36

```
gtggagaggc tattcggta                                              19
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37

```
ccaccatgat attcggcaag                                             20
```

<210> SEQ ID NO 38
<211> LENGTH: 182
<212> TYPE: DNA
<213> ORGANISM: Oryza sativa

<400> SEQUENCE: 38

```
tcctctctac tcctcagcat ctatataagg gccttgcagg cagtggctct cacaccaacg    60
aaacaaggag agactcagag aggaggcgtg ttggttagct cattggcagc agcacacaca   120
aaccacatct cctatatata gctcattttt agcttttgga attgagagag gttttgagag   180
aa                                                                  182
```

<210> SEQ ID NO 39
<211> LENGTH: 149
<212> TYPE: DNA
<213> ORGANISM: Triticum aestivum

<400> SEQUENCE: 39

```
atctgcaggc gctgcctatt taatcccttc cctccctcc attccctcc aagaagagcc     60
acagcttcat ctgcagctac agctcctctt cgtcttcgac acacaagtat tttttcagga  120
caaagatcaa tccagataca catacacct                                    149
```

<210> SEQ ID NO 40
<211> LENGTH: 1133
<212> TYPE: DNA
<213> ORGANISM: Zea mays
<220> FEATURE:
<221> NAME/KEY: Intron
<222> LOCATION: (129)..(1133)

<400> SEQUENCE: 40

```
cttcctcgcc cgccgtaata aatagacacc ccctccacac cctctttccc caacctcgtg    60
ttgttcggag cgcacacaca cacaaccaga tctcccccaa atccacccgt cggcacctcc   120
gcttcaaggt acgccgctcg tcctccccc cctctctac cttctctaga tcggcgttcc     180
ggtccatggt tagggcccgg tagttctact tctgttcatg tttgtgttag atccgtgttt   240
gtgttagatc cgtgctgcta gcgttcgtac acggatgcga cctgtacgtc agacacgttc   300
tgattgctaa cttgccagtg tttctctttg gggaatcctg ggatggctct agccgttccg   360
cagacgggat cgatttcatg atttttttg tttcgttgca tagggtttgg tttgcccttt   420
```

```
tcctttattt caatatatgc cgtgcacttg tttgtcgggt catctttttca tgctttttt     480 tgtcttggtt gtgatgatgt ggtctggttg ggcggtcgtt ctagatcgga gtagaattct     540
gtttcaaact acctggtgga tttattaatt ttggatctgt atgtgtgtgc catacatatt    600
catagttacg aattgaagat gatggatgga aatatcgatc taggataggt atacatgttg    660
atgcgggttt tactgatgca tatacagaga tgcttttgtt cgcttggttg tgatgatgtg    720
gtgtggttgg gcggtcgttc attcgttcta gatcggagta gaatactgtt tcaaactacc    780
tggtgtattt attaattttg gaactgtatg tgtgtgtcat acatcttcat agttacgagt    840
ttaagatgga tggaaatatc gatctaggat aggtatacat gttgatgtgg gtttactga    900 tgcatataca tgatggcata tgcagcatct attcatatgc tctaaccttg agtacctatc    960
tattataata aacaagtatg tttataatt attttgatct tgatatactt ggatgatggc   1020
atatgcagca gctatatgtg gattttttta gccctgcctt catacgctat ttatttgctt   1080
ggtactgttt cttttgtcga tgctcaccct gttgtttggt gttacttctg cag           1133
```

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Family motif Group 21n
<220> FEATURE:
<221> NAME/KEY: modified_base
<222> LOCATION: (2)..(2)
<223> OTHER INFORMATION: a, c, t or g
<220> FEATURE:
<221> NAME/KEY: modified_base
<222> LOCATION: (4)..(6)
<223> OTHER INFORMATION: a, c, t or g
<220> FEATURE:
<221> NAME/KEY: misc_feature
<222> LOCATION: (7)..(12)
<223> OTHER INFORMATION: Core sequence motif
<220> FEATURE:
<221> NAME/KEY: modified_base
<222> LOCATION: (13)..(15)
<223> OTHER INFORMATION: a, c, t or g
<220> FEATURE:
<221> NAME/KEY: modified_base
<222> LOCATION: (17)..(17)
<223> OTHER INFORMATION: a, c, t or g

<400> SEQUENCE: 41
snsnnnwwkg wcnnnsnm                                                    18

<210> SEQ ID NO 42
<211> LENGTH: 29
<212> TYPE: DNA
<213> ORGANISM: Arabidopsis thaliana
<220> FEATURE:
<221> NAME/KEY: misc_feature
<222> LOCATION: (5)..(25)
<223> OTHER INFORMATION: Core sequence motif

<400> SEQUENCE: 42
ctcaaaggcc agaattgacg cagccgttt                                        29

<210> SEQ ID NO 43
<211> LENGTH: 28
<212> TYPE: DNA
<213> ORGANISM: Arabidopsis thaliana

```
<220> FEATURE:
<221> NAME/KEY: misc_feature
<222> LOCATION: (7)..(22)
<223> OTHER INFORMATION: Core sequence motif

<400> SEQUENCE: 43
ccttggccca gtccttggtc gtcgtatc                                             28

<210> SEQ ID NO 44
<211> LENGTH: 11
<212> TYPE: DNA
<213> ORGANISM: Arabidopsis thaliana
<220> FEATURE:
<221> NAME/KEY: misc_feature
<222> LOCATION: (5)..(11)
<223> OTHER INFORMATION: Core sequence motif

<400> SEQUENCE: 44
gttggacttt c                                                              11

<210> SEQ ID NO 45
<211> LENGTH: 28
<212> TYPE: DNA
<213> ORGANISM: Arabidopsis thaliana

<400> SEQUENCE: 45
tctactagag gcccattagg accggcat                                            28

<210> SEQ ID NO 46
<211> LENGTH: 35
<212> TYPE: DNA
<213> ORGANISM: Arabidopsis thaliana

<400> SEQUENCE: 46
aagacaagtt gagagagacg agaccaatca caaca                                    35

<210> SEQ ID NO 47
<211> LENGTH: 35
<212> TYPE: DNA
<213> ORGANISM: Arabidopsis thaliana

<400> SEQUENCE: 47
atccaacatc tcggaccgga tcaatgattt atcat                                    35

<210> SEQ ID NO 48
<211> LENGTH: 25
<212> TYPE: DNA
<213> ORGANISM: Arabidopsis thaliana

<400> SEQUENCE: 48
tcatcaatgt gacataagca aagct                                               25

<210> SEQ ID NO 49
<211> LENGTH: 26
<212> TYPE: DNA
<213> ORGANISM: Arabidopsis thaliana

<400> SEQUENCE: 49
tttgatacgg ttacggttaa ttaacg                                              26

<210> SEQ ID NO 50
<211> LENGTH: 36
<212> TYPE: DNA
<213> ORGANISM: Arabidopsis thaliana
```

<400> SEQUENCE: 50
aagattctca tccaaccgaa acgactcttt cgtttt          36

<210> SEQ ID NO 51
<211> LENGTH: 36
<212> TYPE: DNA
<213> ORGANISM: Arabidopsis thaliana

<400> SEQUENCE: 51
agattctcat ccaaccgaaa cgactctttc gttttt          36

<210> SEQ ID NO 52
<211> LENGTH: 36
<212> TYPE: DNA
<213> ORGANISM: Arabidopsis thaliana

<400> SEQUENCE: 52
tcttcttcat tttaccaaca ccacttgcac acacac          36

<210> SEQ ID NO 53
<211> LENGTH: 35
<212> TYPE: DNA
<213> ORGANISM: Arabidopsis thaliana

<400> SEQUENCE: 53
agttgaatta gttcggttcg gttcggttga tattg           35

<210> SEQ ID NO 54
<211> LENGTH: 24
<212> TYPE: DNA
<213> ORGANISM: Arabidopsis thaliana

<400> SEQUENCE: 54
cgataaactt gcgaaaccct aaaa                       24

<210> SEQ ID NO 55
<211> LENGTH: 25
<212> TYPE: DNA
<213> ORGANISM: Arabidopsis thaliana

<400> SEQUENCE: 55
tattggaagt ttggggcaac atcac                      25

<210> SEQ ID NO 56
<211> LENGTH: 35
<212> TYPE: DNA
<213> ORGANISM: Arabidopsis thaliana

<400> SEQUENCE: 56
ttcaacccta taaaccaaaa caaataacag aatgc           35

<210> SEQ ID NO 57
<211> LENGTH: 36
<212> TYPE: DNA
<213> ORGANISM: Arabidopsis thaliana

<400> SEQUENCE: 57
cgcctcaatc atgaaaacga atcctctgta gtagtg          36

<210> SEQ ID NO 58
<211> LENGTH: 35
<212> TYPE: DNA
<213> ORGANISM: Arabidopsis thaliana

<400> SEQUENCE: 58
ttaccgacac gtaaccaaaa ctcaccgaac accgt    35

<210> SEQ ID NO 59
<211> LENGTH: 35
<212> TYPE: DNA
<213> ORGANISM: Arabidopsis thaliana

<400> SEQUENCE: 59
gtttcgaacg ggaaccaaac cataatatgc gatgc    35

<210> SEQ ID NO 60
<211> LENGTH: 35
<212> TYPE: DNA
<213> ORGANISM: Arabidopsis thaliana

<400> SEQUENCE: 60
acactattgg tcttggtttg gtttatatgc acgac    35

<210> SEQ ID NO 61
<211> LENGTH: 36
<212> TYPE: DNA
<213> ORGANISM: Arabidopsis thaliana

<400> SEQUENCE: 61
gaaaacgatg ggttccaaaa ctgtcgctaa taaact    36

<210> SEQ ID NO 62
<211> LENGTH: 36
<212> TYPE: DNA
<213> ORGANISM: Arabidopsis thaliana

<400> SEQUENCE: 62
tctccactcg ttgtgatttg gtctgcaaga aaacta    36

<210> SEQ ID NO 63
<211> LENGTH: 36
<212> TYPE: DNA
<213> ORGANISM: Arabidopsis thaliana

<400> SEQUENCE: 63
acgttttgaa atattgtttt ggatggagat tttttc    36

<210> SEQ ID NO 64
<211> LENGTH: 36
<212> TYPE: DNA
<213> ORGANISM: Arabidopsis thaliana

<400> SEQUENCE: 64 attttcatt tcgcccaaaa caattatcct aacgtt    36

<210> SEQ ID NO 65
<211> LENGTH: 36
<212> TYPE: DNA
<213> ORGANISM: Arabidopsis thaliana

<400> SEQUENCE: 65
ttttataaca ctaccaaaac caataagccc tttcgt    36

<210> SEQ ID NO 66
<211> LENGTH: 35
<212> TYPE: DNA
<213> ORGANISM: Arabidopsis thaliana

<400> SEQUENCE: 66
tcatcaaacc aatcggtttg gtcctaaaga taatt                              35

<210> SEQ ID NO 67
<211> LENGTH: 35
<212> TYPE: DNA
<213> ORGANISM: Arabidopsis thaliana

<400> SEQUENCE: 67
gtcaatatac acagccaccg aacaaattac tctat                              35

<210> SEQ ID NO 68
<211> LENGTH: 26
<212> TYPE: DNA
<213> ORGANISM: Arabidopsis thaliana

<400> SEQUENCE: 68
aagcgatgtt tacgaacccc aaaatc                                        26

<210> SEQ ID NO 69
<211> LENGTH: 25
<212> TYPE: DNA
<213> ORGANISM: Arabidopsis thaliana

<400> SEQUENCE: 69
agatttgttc gagaaccttg agaaa                                         25

<210> SEQ ID NO 70
<211> LENGTH: 25
<212> TYPE: DNA
<213> ORGANISM: Arabidopsis thaliana

<400> SEQUENCE: 70
ttgctacttc gagaacattg gtcaa                                         25

<210> SEQ ID NO 71
<211> LENGTH: 26
<212> TYPE: DNA
<213> ORGANISM: Arabidopsis thaliana

<400> SEQUENCE: 71
ttagaagtgg ctcgagtgtt ctactt                                        26

<210> SEQ ID NO 72
<211> LENGTH: 26
<212> TYPE: DNA
<213> ORGANISM: Arabidopsis thaliana

<400> SEQUENCE: 72
aagaaagaca atcgagccta gaaatt                                        26

<210> SEQ ID NO 73
<211> LENGTH: 36
<212> TYPE: DNA
<213> ORGANISM: Arabidopsis thaliana

<400> SEQUENCE: 73
aataatgttc aacgttggtg gtggtactca agatgg                             36

<210> SEQ ID NO 74
<211> LENGTH: 36
<212> TYPE: DNA
<213> ORGANISM: Arabidopsis thaliana

<400> SEQUENCE: 74
tcaaatacag gcaaccaaga ctcgagatcc tcatcg    36

<210> SEQ ID NO 75
<211> LENGTH: 25
<212> TYPE: DNA
<213> ORGANISM: Arabidopsis thaliana

<400> SEQUENCE: 75
agaaaaatat tgggcctact gggaa    25

<210> SEQ ID NO 76
<211> LENGTH: 36
<212> TYPE: DNA
<213> ORGANISM: Arabidopsis thaliana

<400> SEQUENCE: 76
agattcctga agtgaggtcc accctaaaat ccattt    36

<210> SEQ ID NO 77
<211> LENGTH: 35
<212> TYPE: DNA
<213> ORGANISM: Arabidopsis thaliana

<400> SEQUENCE: 77
ggtttagtca aagtaaacaa gactttgact gttca    35

<210> SEQ ID NO 78
<211> LENGTH: 36
<212> TYPE: DNA
<213> ORGANISM: Arabidopsis thaliana

<400> SEQUENCE: 78
tgaacttaat cactgtcatt gttttcgtaa caattt    36

<210> SEQ ID NO 79
<211> LENGTH: 26
<212> TYPE: DNA
<213> ORGANISM: Arabidopsis thaliana

<400> SEQUENCE: 79
gaaaaatgtg tgtgtttgtg ttaatt    26

<210> SEQ ID NO 80
<211> LENGTH: 26
<212> TYPE: DNA
<213> ORGANISM: Arabidopsis thaliana

<400> SEQUENCE: 80
atagttccca aacggacacg aacaca    26

<210> SEQ ID NO 81
<211> LENGTH: 26
<212> TYPE: DNA
<213> ORGANISM: Arabidopsis thaliana

<400> SEQUENCE: 81
gcaaactaac gccggcggcc gtcttg    26

<210> SEQ ID NO 82
<211> LENGTH: 25
<212> TYPE: DNA
<213> ORGANISM: Arabidopsis thaliana

<400> SEQUENCE: 82
tagctgttga aatttccaag aaaat                                    25

<210> SEQ ID NO 83
<211> LENGTH: 25
<212> TYPE: DNA
<213> ORGANISM: Arabidopsis thaliana

<400> SEQUENCE: 83
tttttctcgt ccccatcctc tatcc                                    25

<210> SEQ ID NO 84
<211> LENGTH: 26
<212> TYPE: DNA
<213> ORGANISM: Arabidopsis thaliana

<400> SEQUENCE: 84
taggttcctg ccctctccgt tcctcc                                   26

<210> SEQ ID NO 85
<211> LENGTH: 26
<212> TYPE: DNA
<213> ORGANISM: Arabidopsis thaliana

<400> SEQUENCE: 85
tcgaaaccaa ccctctccct tataaa                                   26

<210> SEQ ID NO 86
<211> LENGTH: 26
<212> TYPE: DNA
<213> ORGANISM: Arabidopsis thaliana

<400> SEQUENCE: 86
gaaaccaacc ctctccctta taaata                                   26

<210> SEQ ID NO 87
<211> LENGTH: 36
<212> TYPE: DNA
<213> ORGANISM: Arabidopsis thaliana

<400> SEQUENCE: 87
tgttttgttt ccaccgtctc tcccgtgtcc tctctc                        36

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Thr Ala Gly Ala Glu Val Trp Asn Gln Pro Val Arg Gly Phe Lys
1               5                   10                  15

Val Tyr Glu Gln Thr Glu Met Thr
            20

<210> SEQ ID NO 89
<211> LENGTH: 13
<212> TYPE: DNA
<213> ORGANISM: Arabidopsis thaliana

<400> SEQUENCE: 89
ctcgacacgc aac                                                          13

<210> SEQ ID NO 90
<211> LENGTH: 13
<212> TYPE: DNA
<213> ORGANISM: Arabidopsis thaliana

<400> SEQUENCE: 90
acacacacgt gta                                                          13

<210> SEQ ID NO 91
<211> LENGTH: 13
<212> TYPE: DNA
<213> ORGANISM: Arabidopsis thaliana

<400> SEQUENCE: 91
tacgacgcgt ttc                                                          13

<210> SEQ ID NO 92
<211> LENGTH: 15
<212> TYPE: DNA
<213> ORGANISM: Arabidopsis thaliana

<400> SEQUENCE: 92
gtttacgtca cgtcg                                                        15

<210> SEQ ID NO 93
<211> LENGTH: 15
<212> TYPE: DNA
<213> ORGANISM: Arabidopsis thaliana

<400> SEQUENCE: 93
taatacgtga cgaaa                                                        15

<210> SEQ ID NO 94
<211> LENGTH: 15
<212> TYPE: DNA
<213> ORGANISM: Arabidopsis thaliana

<400> SEQUENCE: 94
tctccaatca cttct                                                        15

<210> SEQ ID NO 95
<211> LENGTH: 16
<212> TYPE: DNA
<213> ORGANISM: Arabidopsis thaliana

<400> SEQUENCE: 95
tgacctaaac catttc                                                       16

<210> SEQ ID NO 96
<211> LENGTH: 16
<212> TYPE: DNA
<213> ORGANISM: Arabidopsis thaliana

<400> SEQUENCE: 96
ttaccgaaac caaagt                                                       16

<210> SEQ ID NO 97
<211> LENGTH: 16
<212> TYPE: DNA
<213> ORGANISM: Arabidopsis thaliana

```
<400> SEQUENCE: 97
caaaccaaac caaacc                                                    16

<210> SEQ ID NO 98
<211> LENGTH: 13
<212> TYPE: DNA
<213> ORGANISM: Arabidopsis thaliana

<400> SEQUENCE: 98
aaacgcaaac gca                                                       13

<210> SEQ ID NO 99
<211> LENGTH: 13
<212> TYPE: DNA
<213> ORGANISM: Arabidopsis thaliana

<400> SEQUENCE: 99
acacgcaaac gat                                                       13

<210> SEQ ID NO 100
<211> LENGTH: 13
<212> TYPE: DNA
<213> ORGANISM: Arabidopsis thaliana

<400> SEQUENCE: 100
tagaccaaaa caa                                                       13

<210> SEQ ID NO 101
<211> LENGTH: 13
<212> TYPE: DNA
<213> ORGANISM: Arabidopsis thaliana

<400> SEQUENCE: 101
atgaccaaac cat                                                       13

<210> SEQ ID NO 102
<211> LENGTH: 14
<212> TYPE: DNA
<213> ORGANISM: Arabidopsis thaliana

<400> SEQUENCE: 102
acgtgtacta ggtc                                                      14

<210> SEQ ID NO 103
<211> LENGTH: 14
<212> TYPE: DNA
<213> ORGANISM: Arabidopsis thaliana

<400> SEQUENCE: 103
agttggactt tgaa                                                      14

<210> SEQ ID NO 104
<211> LENGTH: 18
<212> TYPE: DNA
<213> ORGANISM: Arabidopsis thaliana

<400> SEQUENCE: 104
aattatgaaa agtcgtct                                                  18

<210> SEQ ID NO 105
<211> LENGTH: 18
<212> TYPE: DNA
<213> ORGANISM: Arabidopsis thaliana
```

<400> SEQUENCE: 105
atatgacaaa agtcaaac                                         18

<210> SEQ ID NO 106
<211> LENGTH: 18
<212> TYPE: DNA
<213> ORGANISM: Arabidopsis thaliana

<400> SEQUENCE: 106
tgcgtagaaa agtctgat                                         18

<210> SEQ ID NO 107
<211> LENGTH: 18
<212> TYPE: DNA
<213> ORGANISM: Arabidopsis thaliana

<400> SEQUENCE: 107
cactttgaaa agtattct                                         18

<210> SEQ ID NO 108
<211> LENGTH: 18
<212> TYPE: DNA
<213> ORGANISM: Arabidopsis thaliana

<400> SEQUENCE: 108
tcagtcaaaa agtcaaac                                         18

<210> SEQ ID NO 109
<211> LENGTH: 18
<212> TYPE: DNA
<213> ORGANISM: Arabidopsis thaliana

<400> SEQUENCE: 109
cttgacgaaa agtcaaac                                         18

<210> SEQ ID NO 110
<211> LENGTH: 18
<212> TYPE: DNA
<213> ORGANISM: Arabidopsis thaliana

<400> SEQUENCE: 110
ttttggtcaa agtcaatt                                         18

<210> SEQ ID NO 111
<211> LENGTH: 18
<212> TYPE: DNA
<213> ORGANISM: Arabidopsis thaliana

<400> SEQUENCE: 111
gaatttggaa agtccaac                                         18

<210> SEQ ID NO 112
<211> LENGTH: 21
<212> TYPE: DNA
<213> ORGANISM: Arabidopsis thaliana

<400> SEQUENCE: 112
cacgtgtact aggtcaaacc a                                     21

<210> SEQ ID NO 113
<211> LENGTH: 21
<212> TYPE: DNA
<213> ORGANISM: Arabidopsis thaliana

<400> SEQUENCE: 113
tttcaccagt ggactttga a                                              21

<210> SEQ ID NO 114
<211> LENGTH: 21
<212> TYPE: DNA
<213> ORGANISM: Arabidopsis thaliana

<400> SEQUENCE: 114
aaggccagaa ttgacgcagc c                                              21

<210> SEQ ID NO 115
<211> LENGTH: 21
<212> TYPE: DNA
<213> ORGANISM: Arabidopsis thaliana

<400> SEQUENCE: 115
gcccagtcct tggtcgtcgt a                                              21

<210> SEQ ID NO 116
<211> LENGTH: 44
<212> TYPE: DNA
<213> ORGANISM: Arabidopsis thaliana

<400> SEQUENCE: 116
aactggtcag catgttggac tttccaaatt cattgaccaa agac                     44

<210> SEQ ID NO 117
<211> LENGTH: 44
<212> TYPE: DNA
<213> ORGANISM: Arabidopsis thaliana

<400> SEQUENCE: 117
aactggtcag catgttggtc gttccaaatt cattgaccaa agac                     44

<210> SEQ ID NO 118
<211> LENGTH: 44
<212> TYPE: DNA
<213> ORGANISM: Arabidopsis thaliana

<400> SEQUENCE: 118
aactggtcag catgttggac tttccaaatt catttcccaa agac                     44

<210> SEQ ID NO 119
<211> LENGTH: 44
<212> TYPE: DNA
<213> ORGANISM: Arabidopsis thaliana

<400> SEQUENCE: 119
aactggtcag catgttggtc gttccaaatt catttcccaa agac                     44

<210> SEQ ID NO 120
<211> LENGTH: 11
<212> TYPE: DNA
<213> ORGANISM: Arabidopsis thaliana

<400> SEQUENCE: 120
gttggtcgtt c                                                         11

<210> SEQ ID NO 121
<211> LENGTH: 11
<212> TYPE: DNA
<213> ORGANISM: Arabidopsis thaliana

```
<400> SEQUENCE: 121
gttcgacttt c                                                           11

<210> SEQ ID NO 122
<211> LENGTH: 11
<212> TYPE: DNA
<213> ORGANISM: Arabidopsis thaliana

<400> SEQUENCE: 122
gtcggacttt c                                                           11

<210> SEQ ID NO 123
<211> LENGTH: 11
<212> TYPE: DNA
<213> ORGANISM: Arabidopsis thaliana

<400> SEQUENCE: 123
gttggactgc c                                                           11

<210> SEQ ID NO 124
<211> LENGTH: 11
<212> TYPE: DNA
<213> ORGANISM: Arabidopsis thaliana

<400> SEQUENCE: 124
gttggacttt a                                                           11

<210> SEQ ID NO 125
<211> LENGTH: 25
<212> TYPE: DNA
<213> ORGANISM: Arabidopsis thaliana

<400> SEQUENCE: 125
ctatatgaca aagagaaac ataaa                                             25

<210> SEQ ID NO 126
<211> LENGTH: 25
<212> TYPE: DNA
<213> ORGANISM: Arabidopsis thaliana

<400> SEQUENCE: 126
ctatatgaca ttagtcaaac ataaa                                            25

<210> SEQ ID NO 127
<211> LENGTH: 25
<212> TYPE: DNA
<213> ORGANISM: Arabidopsis thaliana

<400> SEQUENCE: 127
ctatatctca aaagtcaaac ataaa                                            25

<210> SEQ ID NO 128
<211> LENGTH: 26
<212> TYPE: DNA
<213> ORGANISM: Arabidopsis thaliana

<400> SEQUENCE: 128
caacacaaaa cgctttcgca gacctc                                           26

<210> SEQ ID NO 129
<211> LENGTH: 26
<212> TYPE: DNA
<213> ORGANISM: Arabidopsis thaliana
```

<400> SEQUENCE: 129
caacacaaat gccaaacgca gacctc                                    26

<210> SEQ ID NO 130
<211> LENGTH: 26
<212> TYPE: DNA
<213> ORGANISM: Arabidopsis thaliana

<400> SEQUENCE: 130
caacacaaaa cgcaaaccgt gacctc                                    26

<210> SEQ ID NO 131
<211> LENGTH: 29
<212> TYPE: DNA
<213> ORGANISM: Arabidopsis thaliana

<400> SEQUENCE: 131
tgagtcgttt acgtcacgtc gagaatttt                                 29

<210> SEQ ID NO 132
<211> LENGTH: 29
<212> TYPE: DNA
<213> ORGANISM: Arabidopsis thaliana

<400> SEQUENCE: 132
tgagtcgttt acgctgtgtc gagaatttt                                 29

<210> SEQ ID NO 133
<211> LENGTH: 29
<212> TYPE: DNA
<213> ORGANISM: Arabidopsis thaliana

<400> SEQUENCE: 133
tgagtcgttg ccgtcacgtc gagaatttt                                 29

<210> SEQ ID NO 134
<211> LENGTH: 29
<212> TYPE: DNA
<213> ORGANISM: Arabidopsis thaliana

<400> SEQUENCE: 134
tgagtcgttt acgtcacggt gagaatttt                                 29

<210> SEQ ID NO 135
<211> LENGTH: 29
<212> TYPE: DNA
<213> ORGANISM: Arabidopsis thaliana

<400> SEQUENCE: 135
actttccacc agttggactt tgaagccac                                 29

<210> SEQ ID NO 136
<211> LENGTH: 29
<212> TYPE: DNA
<213> ORGANISM: Arabidopsis thaliana

<400> SEQUENCE: 136
actttccacc agtcaggtct tgaagccac                                 29

<210> SEQ ID NO 137
<211> LENGTH: 29
<212> TYPE: DNA
<213> ORGANISM: Arabidopsis thaliana

<400> SEQUENCE: 137
acttttcacc ggttggactt taaagccac                               29

<210> SEQ ID NO 138
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138 vaaagtm                                                        7

<210> SEQ ID NO 139
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139 aaacca                                                         6

<210> SEQ ID NO 140
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140 scaaam                                                         6

<210> SEQ ID NO 141
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 acrcg                                                          5

<210> SEQ ID NO 142
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142 sktgkact                                                       8

<210> SEQ ID NO 143
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 143 mrtsack                                                                  7

<210> SEQ ID NO 144
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144 ccaccaa                                                                  7

<210> SEQ ID NO 145
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145 wwkgwc                                                                   6
```